United States Patent [19]

Dininno et al.

[11] Patent Number: 5,132,420

[45] Date of Patent: * Jul. 21, 1992

[54] INTERMEDIATES FOR PREPARING 2-(SUBSTITUTED-DIBENZO-FURANYL AND DIBENZOTHIENYL) CARBAPENEM ANTIBACTERIAL AGENTS

[75] Inventors: Frank P. Dininno, Old Bridge; Mark L. Greenlee, Rahway; Thomas N. Salzmann, North Plainfield, all of N.J.

[73] Assignee: Merck & Co., Inc., Rahway, N.J.

[ * ] Notice: The portion of the term of this patent subsequent to Jun. 18, 2008 has been disclaimed.

[21] Appl. No.: 596,145

[22] Filed: Oct. 11, 1990

[51] Int. Cl.$^5$ .................... C07D 487/04; C07F 7/10
[52] U.S. Cl. .................................................. 540/302
[58] Field of Search ........................................ 540/302

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 540/302 |

FOREIGN PATENT DOCUMENTS 0277743  8/1988  European Pat. Off. .

OTHER PUBLICATIONS

L. D. Cama et al., Total Synthesis of Thienamycin Analogs-III, Tetrahedron, 39, 2531 (1983).
R. N. Guthikonda, et al., Structure Activity Relationships in the 2-Arylcarbapenem Series, *J. Med. Chem.*, 30, 871 (1987).

*Primary Examiner*—Mukund J. Shah
*Assistant Examiner*—Jyothsna Venkat
*Attorney, Agent, or Firm*—Gabriel Lopez; Joseph F. DiPrima

[57] ABSTRACT

Carbapenem intermediates having the formula:

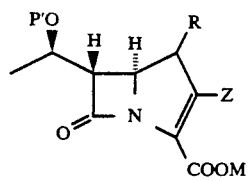

(I.')

where Z is

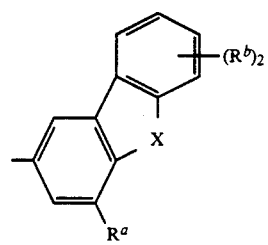

(A.)

or

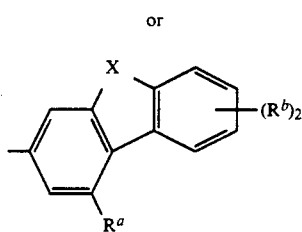

(B.)

M is a removable protecting group for carboxy and P' is a removable protecting group for hydroxy, are useful intermediates for preparing antibacterial agents, especially with respect to activity against methicillin resistant *Staphylococcus aureus* (MRSA).

3 Claims, No Drawings

INTERMEDIATES FOR PREPARING 2-(SUBSTITUTED-DIBENZO-FURANYL AND DIBENZOTHIENYL) CARBAPENEM ANTIBACTERIAL AGENTS

BACKGROUND OF THE INVENTION

The present invention relates to antibacterial agents of the carbapenem class, in which the 2-position side chain is characterized by a dibenzofuranyl or dibenzothienyl moiety, optionally substituted as described in more detail further below.

Thienamycin was an early carbapenem antibacterial agent having a broad spectrum; it has the following formula:

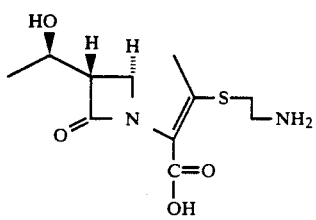

Later, N-formimidoyl thienamycin was discovered; it has the formula:

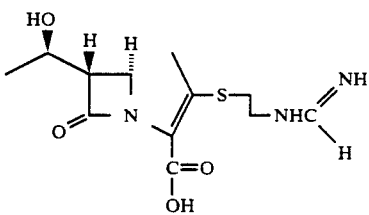

The 2-(substituted-dibenzofuranyl and dibenzothienyl) carbapenems of the present invention are not characterized by a broad antibacterial spectrum such as that of thienamycin or N-formimidoyl thienamycin; but rather, their spectrum of activity is largely limited to gram positive microorganisms, especially methicillin resistant *Staphylococcus aureus* (MRSA) and *Staphylococcus epidermidis* (MRSE); and methicillin resistant coagulase negative *Staphylococci* (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No $\beta$-lactam antibacterial has yet been found which meets these requirements. And, the current agent of choice, vancomycin, a glycopeptide antibacterial, is experiencing an ever increasing amount of resistance by the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

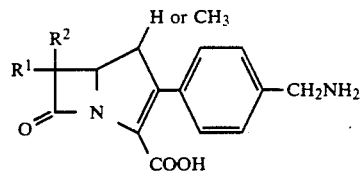

However, there is no description or suggestion of a dibenzofuranyl or dibenzothienyl 2-substituent such as characterizes the compounds of the present invention; nor is there any suggestion of the surprisingly better anti-MRSA activity of the compounds of the present invention.

EP-A-0 277 743 describes a particular class of compounds of the formula:

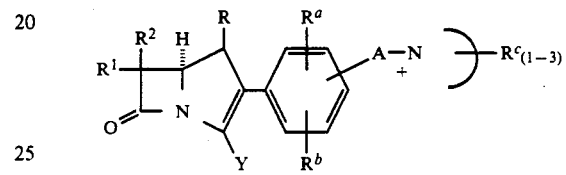

but this limited teaching in no way suggests the totally different compounds of the present invention, nor their surprisingly better anti-MRSA activity.

SUMMARY OF THE INVENTION

The present invention provides novel carbapenem compounds of the formula:

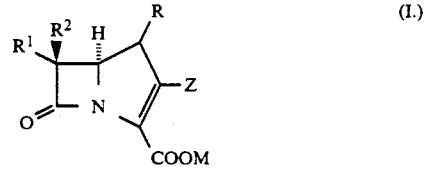

where Z is:

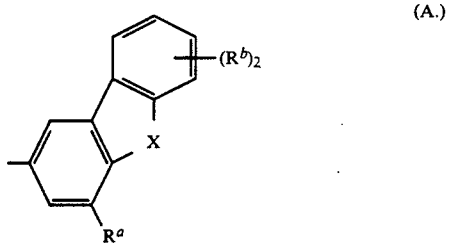

or

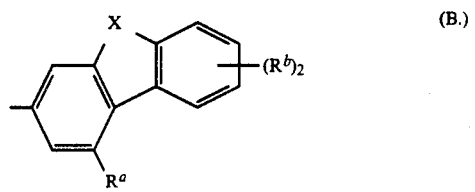

wherein:
X is O or $S(O)_{0-2}$;
R is H or $CH_3$;

$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$ and $R^b$ are independently selected from the group consisting of hydrogen and the radicals set out below:

a) a trifluoromethyl group: $-CF_3$;

b) a halogen atom: $-Br$, $-Cl$, $-F$, or $-I$;

c) $C_1-C_4$ alkoxy radical: $-OC_{1-4}$ alkyl, wherein the alkyl is optionally mono-substituted by $R^q$, where $R^q$ is a member selected from the group consisting of $-OH$; $-OCH_3$; $-CN$; $-C(O)NH_2$; $-OC(O)NH_2$; $CHO$; $-OC(O)N(CH_3)_2$; $-SO_2NH_2$; $-SO_2N(CH_3)_2$; $-SOCH_3$; $SO_2CH_3$; $-F$; $-CF_3$; $-COOM^a$ (where $M^a$ is hydrogen, alkali metal, methyl or phenyl); tetrazolyl (where the point of attachment is the carbon atom of the tetrazole ring and one of the nitrogen atoms is mono-substituted by $M^a$ as defined above); and $-SO_3M^b$ (where $M^b$ is hydrogen or an alkali metal);

d) a hydroxy group: $-OH$;

e) a carbonyloxy radical:

where $R^s$ is $C_{1-4}$ alkyl, phenyl, or heteroaryl, each of which is optionally mono-substituted by $R^q$ as defined above, and where heteroaryl is a monocyclic aromatic hydrocarbon group having 5 or 6 ring atoms in which one of the carbon atoms has been replaced by a nitrogen atom, one additional carbon atom is optionally replaced by a heteroatom selected from O and S, and from 1 to 3 additional carbon atoms are optionally replaced by a nitrogen heteroatom;

f) a carbamoyloxy radical:

where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above), or together a 2- to 5-membered alkylidene radical, interrupted by $-O-$, $-S-$, $-S(O)-$, or $-S(O)_2-$, to form a ring (optionally mono-substituted with $R^q$ as defined above);

g) a sulfur radical:

where $n=0-2$, and $R^s$ is as defined above;

h) a sulfamoyl group: $-SO_2N(R^y)R^z$ where $R^y$ and $R^z$ are as defined above;

i) azido: $N_3$ j) a formylamino group:

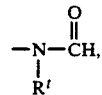

where $R^t$ is H or $C_{1-4}$ alkyl, and the alkyl thereof is optionally mono-substituted by $R^q$ as defined above;

k) $(C_1-C_4$ alkyl)carbonylamino radical:

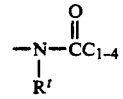

alkyl, where $R^t$ is as defined above, and the alkyl group is also optionally mono-substituted by $R^q$ as defined above;

l) a $(C_1-C_4$ alkoxy) carbonylamino radical:

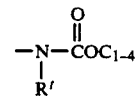

alkyl, where $R^t$ is as defined above, and the alkyl group is also optionally mono-substituted by $R^q$ as defined above;

m) a ureido group:

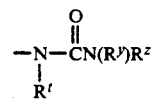

where $R^t$, $R^y$ and $R^z$ are as defined above;

n) a sulfonamido group:

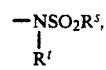

where $R^s$ and $R^t$ are as defined above;

o) a cyano group: $-CN$;

p) a formyl or acetalized formyl radical:

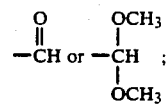

q) $(C_1-C_4$ alkyl)carbonyl radical wherein the carbonyl is acetalized:

alkyl, where the alkyl is optionally mono-substituted by $R^q$ as defined above;

r) carbonyl radical:

where $R^s$ is as defined above;
s) a hydroximinomethyl radical in which the oxygen or carbon atom is optionally substituted by a $C_1$–$C_4$ alkyl group:

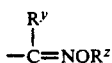

where $R^y$ and $R^z$ are as defined above, except they may not be joined together to form a ring;
t) a ($C_1$–$C_4$ alkoxy)carbonyl radical:

alkyl, where the alkyl is optionally mono-substituted by $R^q$ as defined above;
u) a carbamoyl radical:

where $R^y$ and $R^z$ are as defined above;
v) an N-hydroxycarbamoyl or N($C_1$–$C_4$ alkoxy)-carbamoyl radical in which the nitrogen atom may be additionally substituted by a $C_1$–$C_4$ alkyl group:

where $R^y$ and $R^z$ are as defined above, except that they may not be joined together to form a ring;
w) a thiocarbamoyl group:

where Ry and Rz are as defined above;
x) carboxyl: —COO$M^b$, where $M^b$ is as defined above;
y) thiocyanate: —SCN;
z) trifluoromethylthio: —$SCF_3$;
aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;
ab) an anionic function selected from the group consisting of: phosphono [P=O(O$M^b$)$_2$]; alkylphosphono {P=O(O$M^b$)—[O($C_1$–$C_4$ alkyl)]}; alkylphosphinyl [P=O(O$M^b$)—($C_1$–$C_4$alkyl)]; phosphoramido [P=O(O$M^b$)N(R$^y$)R$^z$ and P=O(O$M^b$)NHR$^x$]; sulfino (SO$_2$$M^b$); sulfo (SO$_3$$M^b$); acylsulfonamides selected from the structures CON$M^b$SO$_2$R$^x$, CON$M^b$SO$_2$N(R$^y$)R$^z$, SO$_2$N$M^b$CON(R$^y$)R$^z$; and SO$_2$N$M^b$CN, where $R^x$ is phenyl or heteroaryl, where heteroaryl is as defined above under $R^s$, and the phenyl and heteroaryl are optionally mono-substituted by $R^q$, as defined above; $M^b$, $R^y$ and $R^z$ are as defined above;
ac) $C_5$–$C_7$ cycloalkyl group in which one of the carbon atoms in the ring is replaced by a heteroatom selected from O, S, NH, or N($C_1$–$C_4$ alkyl) and in which one additional carbon atom may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are at most two carbonyl moieties present in the ring;
ad) $C_2$–$C_4$ alkenyl radical, optionally mono-substituted by one of (1) the substituents a) to ac) above; or (2) phenyl, pyridyl, quinoline, or isoquinoline, each of which is optionally monosubstituted by $R^q$ as defined above;
ae) $C_2$–$C_4$ alkynyl radical, optionally mono-substituted by one of the substituents a) to ac) above;
af) $C_1$–$C_4$ alkyl radical;
ag) $C_1$–$C_4$ alkyl mono-substituted by one of the substituents a)–ac) above;
ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above;
M is selected from:
  i) hydrogen;
  ii) a pharmaceutically acceptable esterifying group or removable carboxyl protecting group; or
  iii) an alkali metal or other pharmaceutically acceptable cation.

The present invention also provides novel carbapenem intermediates of the formula:

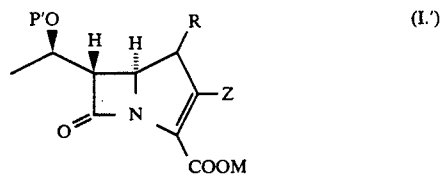

(I.')

wherein:
R is H or CH$_3$;
Z is as defined above except that:
  (1) R$^q$ additionally includes —OP',
  (2) M$^a$ additionally includes M,
  (3) M$^b$ additionally includes M, and
  (4) R$^a$ d) additionally includes —OP';
P' is a removable protecting group for hydroxyl; and
M is a removable carboxyl protecting group.
Preferred intermediates are of the formula:

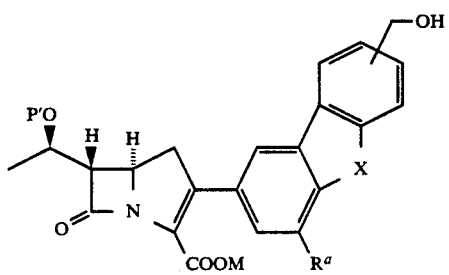

wherein:

$R^a$ is selected from the group consisting of H, Cl, Br, I, $SCH_3$, CN, $CONH_2$, CHO, $SOCH_3$, $SO_2CH_3$, $CO_2M$, $CH_2OP'$, and $OP'$;

$P'$ is a removable protecting group for hydroxy; and

M is a removable carboxy protecting group; and

X is O or $S(O)_{0-2}$.

Suitable hydroxy protecting groups, $P'$, are triorganosilyl groups such as trialkylsilyl, aryl(alkyl)alkoxysilyl, alkoxy(diaryl)silyl, aryl(dialkyl)silyl, and diaryalkylsilyl and carbonate groups such as alkyloxycarbonyl, substituted alkyloxycarbonyl, benzyloxycarbonyl, substituted benzyloxycarbonyl, allyloxycarbonyl, and substituted allyloxycarbonyl. The preferred protecting groups are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

Suitable protecting groups, M, are alkyl, substituted alkyl, benzyl, substituted benzyl, aryl, substituted aryl, allyl, substituted allyl, and triorganosilyl.

M is preferably selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

DETAILED DESCRIPTION OF THE INVENTION

The compounds of the present invention have as the basis for the 2-position substituent a dibenzofuranyl or dibenzothienyl moiety. Different isomeric structures result depending upon point of attachment, and thus for convenience FormulaI bears the 2-position substituent Z, which is then defined (without substituents) as:

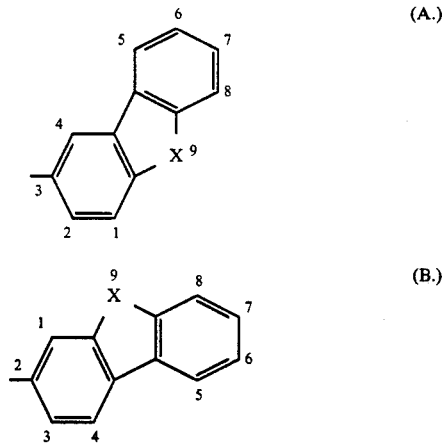

where (A.) and (B.) represent the two isomeric forms, and where X can be oxygen (O), in which case a dibenzofuran nucleus results, or X can be sulfur, in which case a dibenzothiophene nucleus results. Where X is sulfur, the sulfur atom can also be oxygenated with one or two atoms of oxygen. These three possibilities are conveniently summarized in the definition of X as $S(O)_{0-2}$. These two types of nuclei, oxygen- and sulfur-containing, have been found to posses roughly comparable antibacterial, especially anti-MRSA activity, when substituted by the same substituent, even though significant individual substituent/activity variation may exist, and thus both types of nuclei are considered to be part of the same invention, as further described herein. It has also been found that oxygenation of the sulfur atom produces significant changes in biological activity from that of the unoxygenated sulfur species. For example, certain S compounds experience an in vivo efficacy deficit compared to in vitro antibacterial values. The identical $S(O)_1$ compound does not show this deficit, probably as result of reduced plasma protein binding. The $S(O)_1$ compounds are also, usually, more water soluble. Consequently, the oxygenated sulfur atoms of the dibenzothienyl nucleus are also considered a preferred aspect of the present invention.

Of the two possible isomeric forms, designated (A.) and (B.), for both the dibenzofuran nucleus and dibenzothiophene nucleus, the isomeric form (A.) is clearly preferred in most cases, since it has been found that for nearly any given substituent, the (A.) isomer will possess greater antibacterial, especially anti-MSRA activity, than the (B.) isomer as the 2-sidechain of the overall carbapenem compound.

For the various subclasses of compounds of the present invention dictated by the definitions of X and isomeric forms as discussed above, it has been further found that generally for the dibenzofurans there is a preference, within the framework of resultant overall antibacterial, especially anti-MSRA activity, for the $R^a$ substituent, i.e., a 1- or 4-position substituent, although for the dibenzothiophenes no such preference has been found. In the frst ring it has been found that the 2- and 4- and 1- and 3-positions of the (A.) and (B.) isomers, respectively, are relatively inaccessible synthetically, thus leaving only the 1- and 4-positions, respectively, for substitution, i.e., the $R^a$ substituent. In the second ring, by contrast, it is within the scope of the present invention to permit substitution at the 5-, 6-, 7- and 8-positions, although at most two such at a time is theorized that the fused ring system represented by the dibenzofuran and dibenzothiophene nuclei enforces coplanarity of the two phenyl rings involved in the system, thus contributing significantly to the biological activities of the compounds. Nevertheless, a wide range of substitution is possible and often particular substituents significantly enhance overall biological activity.

The $R^a$ and $R^b$ substituents are either neutral or anionic in nature, and are distinguishable chemically and with respect to the biological properties which they confer on the dibenzofuran- and dibenzothiophene-substituted compounds of the present invention, from cationic substitutents. For example, it has been found that the neutral or anionic substituted compounds of the present invention afford greater water solubility and reduced potential for CNS side effects, than comparable solely cationic substituted dibenzofuran and dibenzothiophene containing compounds.

Although a substantial number and range of such neutral and anionic substitutents have been described herein, all of these are contemplated to be a part of the present invention based on the biological performance of substituents related in terms of their medicinal chemistry.

It has been found beneficial to employ an electron withdrawing group at the 1- or 4-position ($R^a$), although other types of substituents may also be employed. Substituents which tend to confer improved water solubility on the overall compound have been found useful, since they are contemplated to thereby improve the transport of the compound involved. A significant number of substituents of this type have been set forth. As a general matter, however, it is conjectured that the improved anti-MSRA activity results from conformation of the overall molecule uniquely conferred by the dibenzofuran and dibenzothiophene nuclei themselves.

With reference to the above definitions, "alkyl" means a straight or branched chain aliphatic hydrocarbon radical.

The term "heteroatom" means N, S, or O, selected on an independent basis.

The term "heteroaryl" has been defined herein to mean a monocyclic aromatic hydrocarbon group having 5 or 6 ring atoms in which one of the carbon atoms has been replaced by a nitrogen atom, and in which one additional carbon atoms is optionally replaced by a heteroatom selected from O and S, and from 1 to 3 additional carbon atoms are optionally replaced by a nitrogen heteroatom. This definition sets forth a limited class of heterocyclic compounds expected to be suitable as substituents for the 2-dibenzofuranyl and dibenzothioenyl carbapenem compounds of the present invention. It will be noted that only a tetrazolyl heteroaryl may be directly attached to the phenyl rings of the nuclei. All of the other defined heteroaryls are attached by way of other substituents, as set forth above. It is required that the heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1O or 1S). While additional nitrogen atoms may be present together with the first nitrogen and oxygen or sulfur, giving, e.g., a thiadiazole (2N+1S), the preferred heteroaryls are those where only nitrogen heteroatoms are present when there is more than one. Typical of these are pyrazole, imidazole, pyrimidine and pyrazine (2N); triazine (3N); and tetrazole (4N).

The heteroaryl group is always optionally mono-substituted by $R^q$, defined above, and substitution can be on one of the carbon atoms or one of the heteroatoms, although in the latter case certain substituent choices may not be appropriate.

The term "tetrazolyl" as used herein refers to only the tetrazole radical wherein the point of attachment is the carbon atom of the tetrazole ring.

Under the definition of "M", the terms "pharmaceutically acceptable esterifying group" and "pharmaceutically acceptable cation" refer to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

It is preferred that either $R^1$ or $R^2$ is H and the other is (R)—CH$_3$CH(OH)— or (R)—CH$_3$CH(F)—. More preferably, $R^1$ is (R)—CH$_3$CH(OH)— or (R)—CH$_3$CH(F)—; and R and $R^2$ are both H. It is most preferred that $R^1$ is (R)—CH$_3$CH(OH)— and $R^2$ is H.

Representative $R^a$ and $R^b$ groups are H, —CH$_3$, —CH$_2$CH$_3$, —(CH$_2$)$_3$CH$_3$, —OCH$_3$, —SCH$_3$, tetrazoly, —COOH, —CH$_2$CONH$_2$, —CH$_2$CH$_2$SO$_3$H, —CONH$_2$, —SO$_2$NH$_2$, —SO$_3$H, —CON(CH$_3$)$_2$, —CN, —CH$_2$CN, —CH$_2$SCH$_3$, —CH$_2$SO$_3$H, —CH$_2$SOCH$_3$, —CH$_2$SO$_2$CH$_3$, —SO$_2$CH$_3$, —SOCH$_3$, —CH$_2$OCH$_3$, —N$_3$, —OCONH$_2$, —OH, —CHO, —CH$_2$P(O)(OCH$_3$)OH, —CF$_3$, —CH$_2$OC(O)NH$_2$, —CH$_2$SO$_2$NH$_2$, —SCH$_2$CH$_2$CN, Br, Cl, F, —SCF$_3$, —CH$_2$SCF$_3$, —SCH$_2$CF$_3$, —COCH$_3$, —CH=NOH, —CONHOH, —C(S)NH$_2$, —OCOCH$_3$, —NHCOCH$_3$, —NHCO$_2$CH$_3$, —NHCONH$_2$, —NHSO$_2$CH$_3$, —SCN, —CH=CHCHO, —SCH$_2$CH$_2$OHM —CH$_2$OH, —CH=NOCH$_2$CO$_2$H, —CO$_2$CH$_2$CH$_2$OH, and —SO$_2$NHCH$_2$CONH$_2$.

While R=H is usually preferred, there are instances in which R=CH$_3$ may provide improved chemical stability, water solubility, or pharmacokinetic behavior. The substituent R=CH$_3$ may be of either configuration, i.e., the α or β-stereoisomer.

For most of the compounds exemplified herein, the R substituent is hydrogen. This is the result not only of a more facile synthesis for such compounds, but also of a preference for R=hydrogen based on the superior antibacterial activity of such compounds.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable esters of the novel carbapenem compounds of the present invention are such as would be readily apparent to a medicinal chemist, and include, for example, those described in detail in U.S. Pat. No. 4,309,438, Columnm 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described below. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents unde mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl, phenacyl, p-methoxybenzyl, acetonyl, o-nitrobenzyl, 4-pyridylmethyl, and $C_1$-$C_6$ alkyl such as methyl, ethyl or t-butyl.

The compounds of the present invention are in general valuable antibacterial agents active against various Gram-positive and to a lesser extent, for the most part, Gram-negative bacteria and accordingly, find utility in human and veterinary medicine. Representative pathogens which are sensitive to the antibacterial agents of the present invention include various species or strains of the following: Staphylococcus, Enterococcus, *Escherichia coli*, Kleibsiella, Enterobacter, Bacillus, Salmonella, Serratia, Proteus, and Bacterium. The antibacterials of the invention are not limited to utility as medicaments; they may be used in all manner of industry, for example: additives to animal feed, preservation of food, disinfectants, and in other industrial system where control oof bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments creams, lotions, paints, or powders.

The dosage to be administered depends to a large extent upon the condition and size of the subject being treted as well as the route and frequency of administration, the parenteral route by injection being preferred for generalized infections. Such matters, however, are left to the routine discretion of the therapist according to principles of treatment well known in the anti-bacteriaal art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The composition for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 2-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attach by a renal enzyme known as dehydropeptidase (DHP). This attack or degradation may reduce the efficacyy of the carbapenem antibacterial agent. The compounds of the present invention, on the other hand, are significantly less subject to such attack, and therefore may not require use of a DHP inhibitor. However, such use is optional and contemplated to be a part of the present invention. Inhibitors of DHP and their use with carbapenem antibacterial agents are disclosed in the prior art [see European Patent Applications No. 79102616.4 filed Jul. 24, 1979 (Patent No. 0 010 573); 79102615.6, filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited Europeant patent applications 1.) define the procedure for determining DHP susceptibility of the present carbapenems and 1.) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

METHODS OF PREPARATION

The 2-(substituted-dibenzofuranyl and dibenzothienyl) carbapenem compounds of the present invention may be prepared in accordance with well known procedures in the art. Particularly useful are the synthetic schemes set out further below in which the symbols R, X, $R^a$ and $R^b$ are as defined above.

SCHEME I

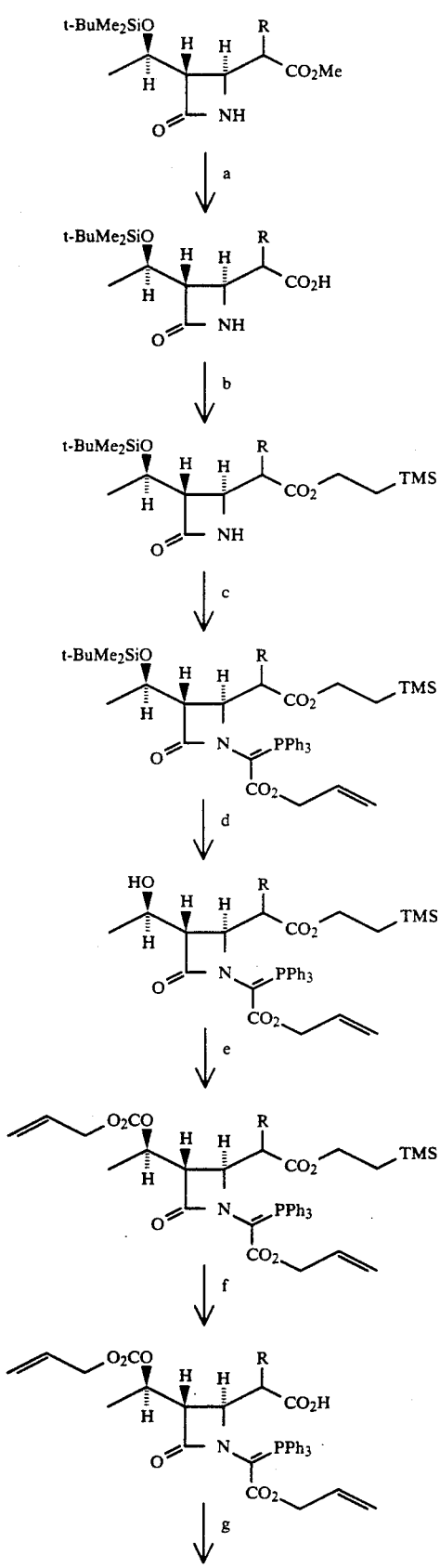

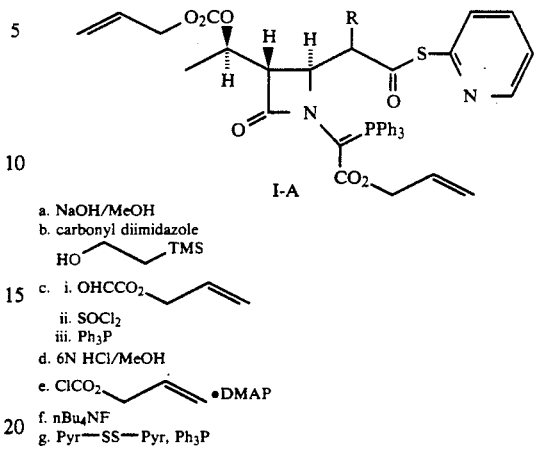

a. NaOH/MeOH
b. carbonyl diimidazole
HO⁀⁀TMS
c.  i. OHCCO₂⁀⁀
    ii. SOCl₂
    iii. Ph₃P
d. 6N HCl/MeOH
e. ClCO₂⁀⁀ •DMAP
f. nBu₄NF
g. Pyr—SS—Pyr, Ph₃P Scheme I shows the synthesis of the pyridyl-thioester intermediate I-A. The steps for preparing intermediate I-A are well known in the art and are analogous to the procedures described, for example, in U.S. Pat. Nos. 4,260,627 and 4,543,257; L. D. Cama et al. *Tetrahedron* 39, 2531 (1983); R. N. Guthikond et al. *J. Med. Chem.* 30, 871 (1987).

Scheme II illustrates the coupling of I-A with the desired aromatic side-chain via a Grignard reaction followed by formation of the carbapenem ring system by an intramolecular Wittig reaction. Thus, reaction of I-A with a dibenzofuranyl- or dibenzothienyl-bromomagnesium reagent III in tetrahydrofuran (THF) at from −70° C. to about 20° C. gives an aryl ketone IV. The Grignard reagent III is prepared by conventional means from the corresponding aryl bromide II. Thus, reaction of II with magnesium metal in THF at from about 20° C. to 60° C. provides III. Alternatively, II may be reacted with t-butyllithium in THF followed by the addition of magnesium bromide to produce III.

The substituted-dibenzofuranyl and -dibenzothienyl bromides II are obtained by standard literature methods. The synthesis, substitution, and elaboration of dibensofurans and dibensothiophenes has been well reviewed in the literature: M. V. Sargent and P. O. Stransky, Adv. Heterocycl. Chem. 35, 1–81 (1984); W. E. Parham, Heterocycl. Comp. 2, 123 (1951); R. Livingstone in Rodd's Chemistry of Carbon Compounds, 2nd Ed., Vol. IV Part A, Heterocyclic Compounds, pp. 194–202 (1973); F. M. Dean and M. V. Sargent in Comprehensive Heterocyclic Chemistry, Vol. 4, Part 3, p. 599 (1979): D. M. X. Donnelly and M. J. Meegan, ibid., p. 657 (1979); J. Ashby and C. C. Cook, Adv. Heterocycl. Chem. 16, pp. 181–288 (1974); D. K. Fukushima, Heterocycl. Comp. 2, 164 (1951); R. Livingstone in Rodd's Chemistry of Carbon Compounds, 2nd Ed., Vol. IV Part A, Heterocyclic Compounds, pp. 300–305 (1973); S. Rajappa in Comprehensive Heterocyclic Chemistry. Vol. 4, Part 3, p. 741 (1979; and E. Campaigne, ibid., p. 863 (1979).

Cyclization of phosphorane IV is accomplished by heating at reflux in p-xylene (138° C.) in the presence of hydroquinone as a radical scavenger for about 1 hour to provide the carbapenem ester V.

In Scheme II, the C-3 carboxyl group and the C-8 hydroxyl group are both blocked with allyl based protecting groups. This conveniently allows for removal of both blocking groups in a single step via a conventional palladium catalyzed de-allylation reaction to provide the carbapenem carboxylate VI. Other suitable protecting groups are known in the art and may also be employed.

The above reaction Scheme illustrates a particular isomeric attachment of the dibenzofuran or dibenzothiophene nucleus to the carbapenem (defined previously as A). The alternative isomeric attachment (defined previously as B) may be obtained by changing the position of the bromine atom in the side-chain precursor II.

It is often advantageous for the $R^a$ and/or $R^b$ substituent of the side-chain precursor II to be introduced initially in a protected or precursory form. This is due to the incompatibility of certain substituents $R^a$ or $R^b$ with the highly basic and nucleophilic conditions of the Grignard reaction and/or the high temperature employed in the internal Wittig cyclization. Depending on the specific substituent, elaboration to the desired $R^a$ and/or $R^b$ may be best accomplished at the phosphorane intermediate IV (e.g., Examples 31, 32, and 285) or after cyclization to the protected carbapenem V (e.g., Examples 28-30, 37, 293, 295-299, and 303).

In the case of the dibenzothiophene nucleus X=S), oxidation to the S-oxide (X=SO) is best accomplished after cyclization to the carbapenem V (e.g., Examples 3, 27, 292, 298, and 301). The dibenzothienyldioxide compounds (X=SO$_{22}$) may be obtained by further oxidation of the corresponding S-oxide compound or, alternatively, by using a dibenzothienyl-dioxide starting material (II; X=SO$_2$) in the Grignard coupling reaction.

SCHEME II

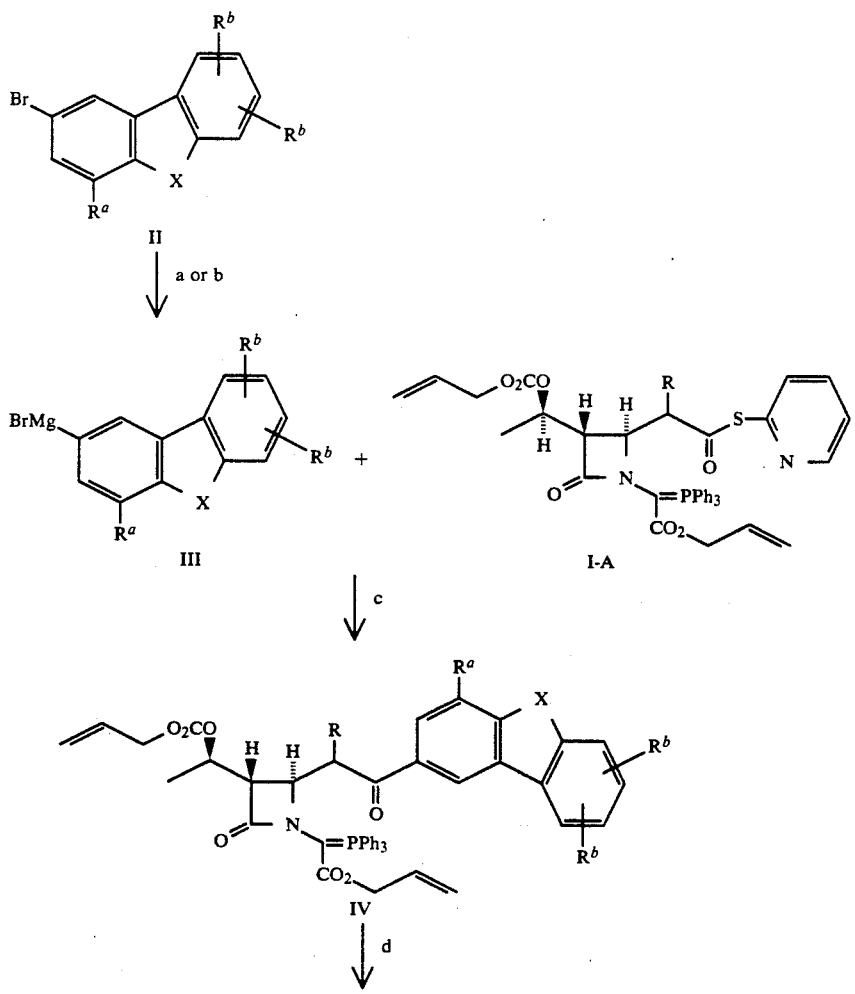

SCHEME II

-continued

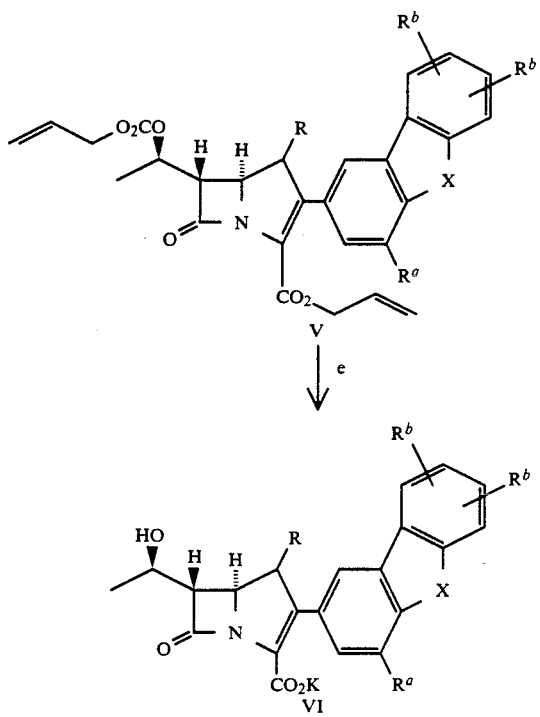

a. Mg, THF
b. i. t-BuLi, THF
   ii. MgBr$_2$
c. THF, $-70°$ C. $\longrightarrow$ $-20°$ C.
d. p-xylene, 138° C.
e. (Ph$_3$P)$_4$Pd
   C$_7$H$_{15}$CO$_2$H, C$_7$H$_{15}$CO$_2$K Scheme III shows an alternative process for the attachment of the base dibenzofuranyl or dibenzothienyl compound II to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify the bromodibenzofuran or bromodibenzothiophene II to the corresponding stannane IX. This is accomplished by reacting II with t-butyllithium in THF at from $-78°$ to $-50°$ C. followed by the addition of trimethyltin chloride. Alternatively, compound II may be reacted with hexamethylditin in the presence of a palladium(O) catalyst such as tetrakis(triphenylphosphine)-palladium in an inert solvent such as toluene at from 25° C. to 110° C. for from 0.25-24 hours to provide the stannane IX.

The other starting material for Scheme III is the 2-oxocarbapenam VII. The steps for preparing the intermediate VII are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck & Co., Inc. and hereby incorporated by reference.

Referring to Scheme III, the 2-oxocarbapenam VII is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran. An organic nitrogen base, such as triethylamine and the like, is then added to the reaction solution followed immediately by a silylating agent, such as trimethylsilyl trifluoromethanesulfonate to provide intermediate VIII. An aprotic polar coordinating solvent, such as DMF, 1-methyl-2-pyrrolidinone (NMP) and the like, is added. This is followed by the addition of a palladium compound, such as tris-(dibenzylideneacetone)dipalladium-chloroform, palladium acetate and the like, optionally a suitably substituted phenylphosphine, such as tris(4-methoxyphenyl)phosphine, tris(2,4,6-trimethoxyphenyl)phosphine (TTPP) and the like, and the stannane IX. A metal halide, such as lithium chloride, zinc chloride and the like, is added and the reaction solution is quickly warmed to a suitable temperature, such as 0° to 50° C., and allowed to stir for a suitable amount of time. The carbapenem X is obtained by conventional isolation/-purification methodology known in the art. Removal of the protecting groups from X may be accomplished in a conventional manner. Thus, treatment of X with 0.1-3.0 equivalents of acetic acid in tetrahydrofuran-water at 20°-50° C. followed by hydrogenation over palladium on carbon at atmospheric pressure in the presence of potassium carbonate provides the carbapenem carboxylate VI.

Generally speaking, the milder conditions of the synthesis shown in Scheme III allow for a wider range of functional groups $R^a/R^b$ to be present than the synthesis illustrated in Scheme II. The synthesis is also applicable to the oxidized forms of the dibenzothiophene nucleus (i.e., $X=SO$, $SO_2$). However, in certain cases it is advantageous for the $R^a$ and/or $R^b$ substituent of the stannane IX to be introduced in a protected or precursor form. Final elaboration of $R^a$ and/or $R^b$ from a precursor substituent, e.g., hydroxymethyl, may be accomplished on carbapenem intermediate X.

The above reaction Scheme illustrates a particular isomeric attachment of the dibenzofuran or dibenzothiophene nucleus to the carbapenem (defined previously as A). The alternative isomeric attachment (defined previously as B) may be obtained by changing the position of the bromine atom in the side-chain precursor II.

SCHEME III

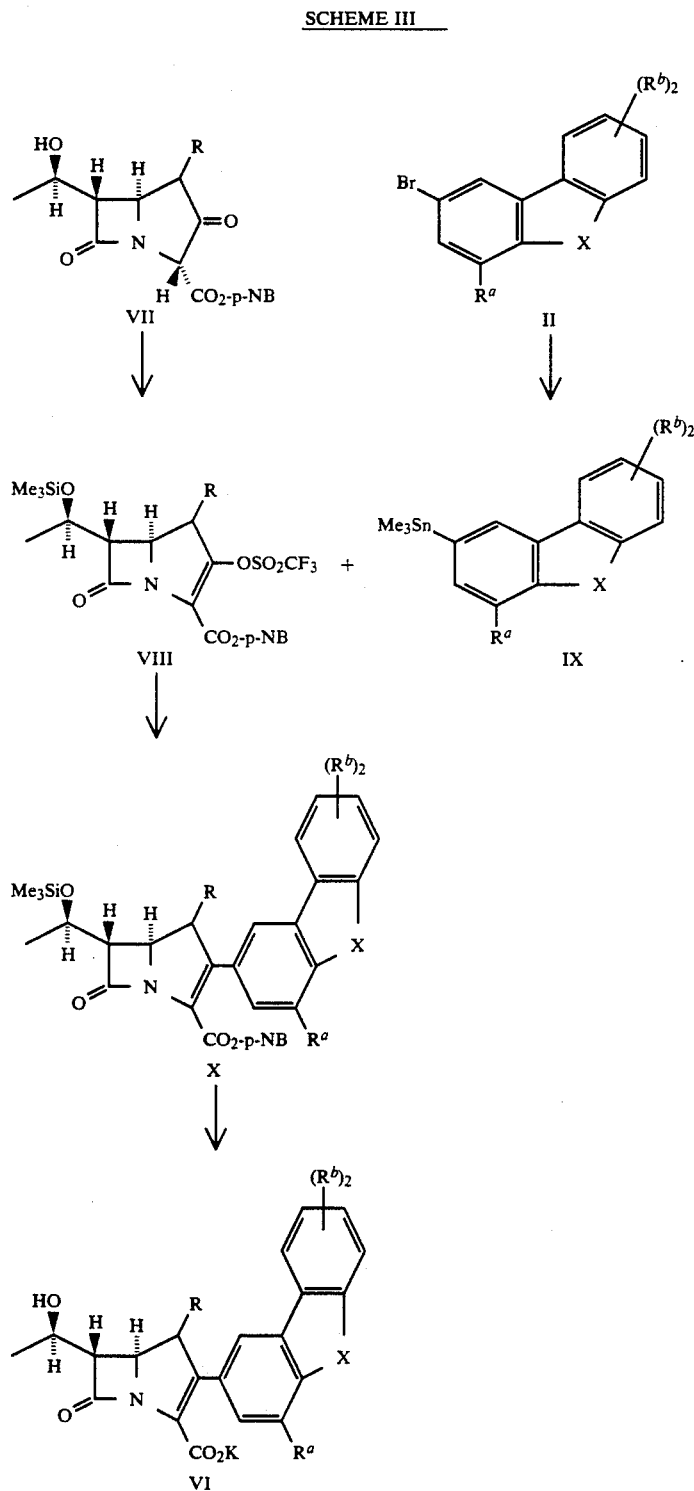

SCHEME III

-continued

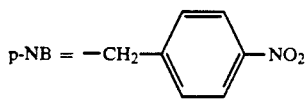

The general synthesis description depicted above in the Schemes shows a protected 1-hydroxyethyl substitution on the 6-position of the carbapenem. After final deprotection, a 1-hydroxyethyl substituent is obtained, which is preferred in most cases. However, it has been found that with certain 2-sidechain selections, the ultimate balance of favorable properties in the overall molecule may be enhanced by selection of the 6-(1-fluoroethyl) moiety instead. Preparation of 6-(fluoroalkyl) compounds within the scope of the present invention is carried out in a straightforward manner using techniques well known in the art of preparing carbapenem antibacterial compounds. See, e.g., J. G. deVries et al., Heterocycles, 23 (8), 1915 (1985); BE 900 718 A (Sandoz); Japanese Patent Pub. No. 6-0163-882-A (Sanruku Ocean); and Examples 41-43 and 323-324.

Unless otherwise indicated, all of the temperatures in the working examples which follow are in degrees Celsius (°C.).

phoranylidene)methyl-3-[1R-(allyloxycarbonyloxy)-ethyl)-4-[(2-pyridylthio)carbonyl]methyl-azetidin-2-one 1 (1.063 g, 1.5 mmol) in 8 ml of THF at −50° C. The temperature was allowed to rise to −10° C. during 45 minutes, and then the reaction mixture was hydrolyzed with saturated NH$_4$Cl solution, diluted with a large volume of ethyl ether, and washed successively with saturated NH$_4$Cl, 1N NaOH (2X), H$_2$O, and brine. Drying (MgSO$_4$) and evaporation gave a yellow oil which was purified by flash chromatography through 100 g of silica gel (65:35 EtOAc/hexane) to yield 453 mg (39%) of the title ketone as a white foam.

$^1$H-NMR (300 MHz, CDCl$_3$): inter alia; δ1.17 (d, J=6.3 Hz, 3H, CH$_3$).

IR (CHCl$_3$): 1745 (β-lactam), 1680 (ketone), 1615 cm$^{-1}$ (ylide).

EXAMPLE 1

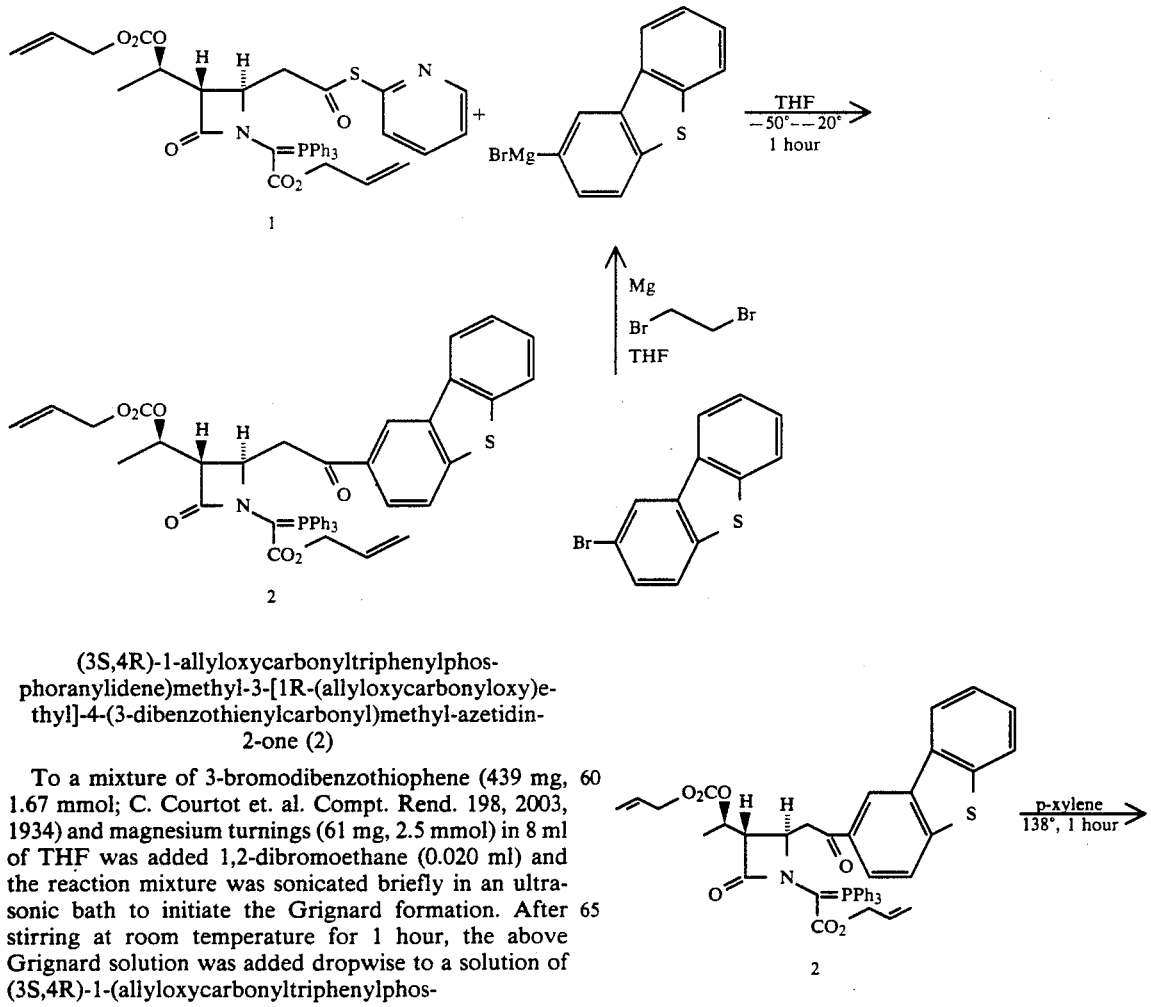

(3S,4R)-1-allyloxycarbonyltriphenylphosphoranylidene)methyl-3-[1R-(allyloxycarbonyloxy)ethyl]-4-(3-dibenzothienylcarbonyl)methyl-azetidin-2-one (2)

To a mixture of 3-bromodibenzothiophene (439 mg, 1.67 mmol; C. Courtot et. al. Compt. Rend. 198, 2003, 1934) and magnesium turnings (61 mg, 2.5 mmol) in 8 ml of THF was added 1,2-dibromoethane (0.020 ml) and the reaction mixture was sonicated briefly in an ultrasonic bath to initiate the Grignard formation. After stirring at room temperature for 1 hour, the above Grignard solution was added dropwise to a solution of (3S,4R)-1-(allyloxycarbonyltriphenylphos-

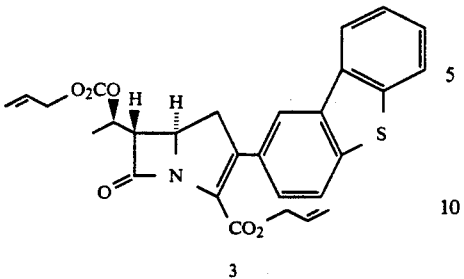

3

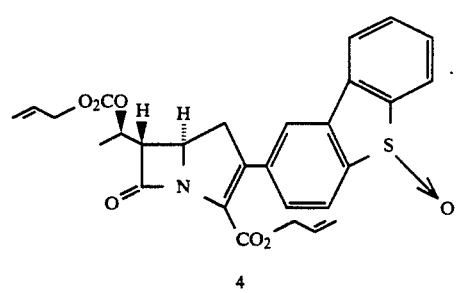

4

Allyl-(5R,6S)-2-(3-dibenzothienyl)-6-[1R-(allyloxycarbonyloxy)ethyl]-carbapen-2-em-3-carboxylate (3)

A solution of the phosphorane 2 (230 mg, 0.294 mmol) and several crystals of p-hydroquinone in 10 ml of p-xylene was heated to reflux (138° C.). After 1 hour, the solution was cooled to room temperature, concentrated under high vacuum, and the residual oil was purified by flash chromatography through 25 g of silica gel (35:65 EtOAc/hexane) to yield 145 mg (98%) of the title carbapenem as a pale yellow oil.

$^1$H-NMR (300 MHz, CDCl$_3$): δ1.50 (d, J=6.3 Hz, 3H, CH$_3$); 3.25-3.45 (m, 2H, H1); 3.45 (dd, J=2.8, 8.5 Hz, 1H, H6); 4.33 (dt, J=2.8, 9.2 Hz, 1H, H5); 4.55-4.75 (m, 4H, —OCH$_2$C=C); 5.1-5.4 (m, 5H, H8, —C=CH$_2$); 5.75-6.0 (m, 2H, —CH=C); 7.4-7.5 (m, 3H); 7.81 (d, J=8.2, 1H); 7.8-7.85 (m, 1H), 8.05-8.15 (m, 1H); 8.15 (d, J=1.6 Hz, 1H).

IR (CHCl$_3$): 1780 (β-lactam), 1745 (carbonate), 1725 cm$^{-1}$ (ester).

UV (CH$_3$CN): λmax = 320 nm (ε = 10,800).

EXAMPLE 3

Allyl-(5R,6S)-2-(9-oxo-3-dibenzothienyl)-6-[1R-(allyloxycarbonyloxy)ethyl]-carbapen-2-em-3-carboxylate (4)

A solution of the carbapenem 3 (150.1 mg, 0.298 mmol) in 3 ml of methylene chloride was cooled to 0° C. and 0.5M aqueous NaHCO$_3$ (1.5 ml) was added followed by 99% m-chloroperbenzoic acid (78 mg, 0.45 mmol). The two-phase mixture was vigorously stirred for 45 minutes and was then quenched with 5% Na$_2$S$_2$O$_3$ and stirred until a negative starch-iodide test was obtained. The reaction mixture was diluted with ethyl acetate and washed with H$_2$O and brine. Drying (MgSO$_4$) and evaporation gave a yellow oil which was separated by flash chromatography through 15 g of silica gel (7:3 EtOAc/hexane) to yield 82 mg (53%) of the title sulfoxide as a yellow oil.

$^1$H-NMR (300 NHz, CDCl$_3$): δ1.48 (d, J=6.41 Hz, 3H, CH$_3$); 3.15-3.4 (m, 2H, H1), 3.46 (dd, J=2.8, 8.2 Hz, 1H, H6); 4.33 (dt, d=2.8, 9.1 Hz, 1H, H5); 4.55-4.75 (m, 4H, —OCH$_2$C=C), 5.1-5.4 (m, 5H, H8, —C=CH$_2$); 5.75-6.0 (m, 2H, —CH=C), 7.35-8.0 (m, 7H, ArH).

IR (CHCl$_3$): 1785 (β-lactam), 1745 (carbonate), 1725 cm$^{-1}$ (ester).

UV (CH$_3$CN): λmax = 294 nm (ε = 10,500).

EXAMPLE 4

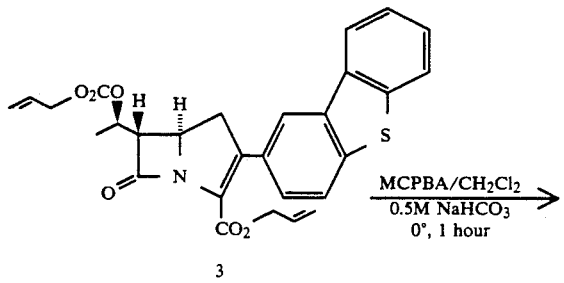

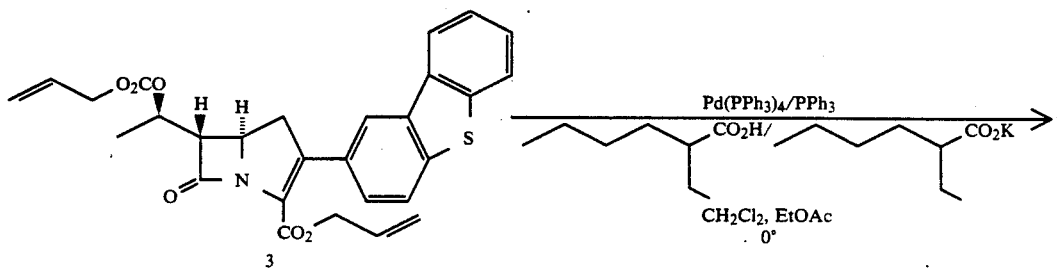

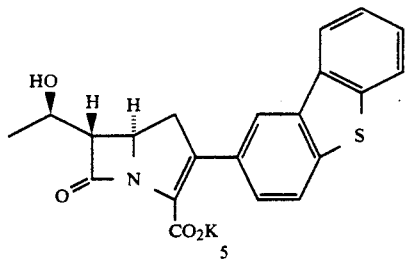

Potassium (5R,6S)-2-(3-dibenzothienyl)-6-(1R-hydroxyethyl)-carbapen-2-em-3-carboxylate (5)

To a solution of the carbapenem 3 (66.5 mg, 0.132 mmol) in 0.7 ml of ethyl acetate at 0° C. were added in sequence a solution of potassium 2-ethylhexanoate in ethyl acetate (0.5M, 0.26 ml), a solution of 2-ethylhexanoic acid in methylene chloride (1.0M, 0.13 ml), and a solution of tetrakis(triphenylphosphine)palladium (14 mg, 0.012 mmol) and triphenylphosphine (10 mg, 0.038 mmol) in 0.7 ml of methylene chloride. After 1 hour, the reaction mixture was pipetted into a centrifuge tube containing cold ethyl ether (2 ml) and the solid was isolated by centrifugation, washing twice with ethyl ether. After drying under a stream of nitrogen and then in vacuo, 54.6 mg of a yellow solid was obtained. Purification by reverse-phase preparative TLC (2:1 H$_2$O/CH$_3$CN) yielded 26.8 mg (48%) of the title compound as an off-white lyophilized solid.

$^1$H-NMR (300 MHz, 2:1 D$_2$O/CD$_3$CN): $\delta$1.66 (d, J=6.2 Hz, 3H, CH$_3$); 3.52 (dd, J=9.9, 16.9 Hz, 1H, H1a); 3.82 (dd, J=2.7, 6.0 Hz, 1H, H6); 3.89 (dd, J=8.7, 16.9 Hz, 1H, H1b); 4.59 (m, 1H, H8); 4.67 (dt, J=2.7, 9.8 Hz, 1H, H5); 7.85-7.95 (m, 3H), 8.24 (d, J=8.4 Hz, 1H); 8.3 (m, 1H); 8.6 (s, 1H); 8.6-8.65 (m, 1H).

IR (KBr): 1750 ($\beta$-lactam), 1600 cm$^{-1}$ (carboxylate).
UV (H$_2$O): $\lambda$max=310 nm ($\epsilon$=13,800), 299 (14,300).

EXAMPLE 5

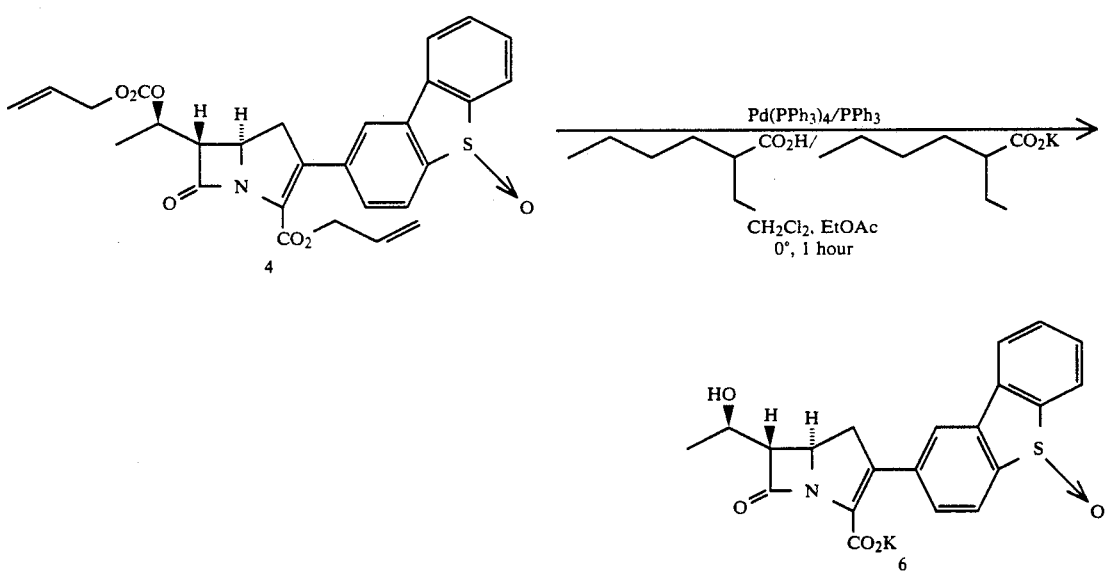

Potassium (5R,6S)-2-(9-oxo-3-dibenzothienyl)-6-(1R-hydroxyethyl)-carbapen-2-em-3-carboxylate (6)

In a manner analogous to that described in Example 4, the carbapenem 4 (113.8 mg, 0.219 mmol) was deallylated to yield 44.5 mg (47%) of the title compound as an off-white lyophilized solid.

$^1$H-NMR (300 MHz, 2:1 D$_2$O/CH$_3$CN): $\delta$1.69 (d, J=6.4 Hz, 3H, CH$_3$); 3.53 (dd, J=9.9, 16.8 Hz, 1H, H1a); 3.8-3.95 (m, 2H, H6, H1b); 4.55-4.75 (m, 2H, H5, H8); 7.9-8.45 (m, 7H, ArH).

IR (KBr): 1750 ($\beta$-lactam), 1595 (carboxylate).
UV (H$_2$O): $\lambda$max=328 nm ($\epsilon$=9,700), 295 ($\epsilon$=14,000).

EXAMPLES 6-9

Operating as described in the previous examples, and employing the appropriate aryl bromides (ArBr) which are known in the literature, the following compounds were analogously prepared:

| Example No. | Ar | $\lambda_{max}^{H_2O}$ |
|---|---|---|
| 6 | 2-(methylsulfonyl)biphenyl | 329 nm(ε = 10,600) 294 nm(ε = 14,000) |
| 7 | dibenzofuran-yl | 290 nm(ε = 20,700) |
| 8 | 2-phenoxyphenyl | 322 nm(ε = 27,000) |
| 9 | 2-phenylthiophenyl | 321 nm(ε = 23,000) |

EXAMPLE 10

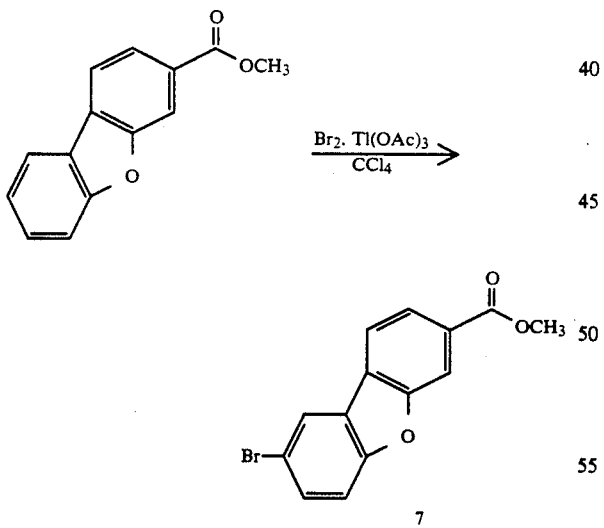

Methyl 3-Bromo-dibenzofuran-7-carboxylate (7)

To a solution of methyl dibenzofuran-2-carboxylate [0.109 g, 0.482 mmol; H. Gilman et. al., J. Amer. Chem. Soc. 61, 2836 (1939)] in carbon tetrachloride (3 ml) and methylene chloride (1.5 ml) at room temperature was added thallium(III) acetate sesquihydrate (58.9 mg, 0.144 mmol). A solution of bromine (76 mg. 0.48 mmol) in 0.5 ml of carbon tetrachloride was added slowly dropwise during 1 hour. After stirring for an additional 2 hours, the mixture was filtered through 30 g of silica gel, eluting with methylene chloride. The filtrate was washed successively with 10% NaHSO₃, saturated NaHCO₃, H₂O, and brine. Drying (MgSO₄) and evaporation yielded 102 mg (69%) of the title compound as a yellow solid which was used in the next step without further purification.

¹H-NMR (300 MHz, CDCl₃): δ3.98 (s, 3H, —OCH₃); 7.46 (d, 1H); 7.60 (dd, J=1.96, 8.73, 1H); 7.92 (d, J=8.11, 1H); 8.04–8.10 (m, 2H); 8.22 (s, 1H).

EXAMPLE 11

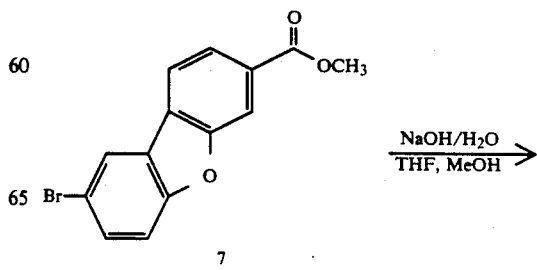

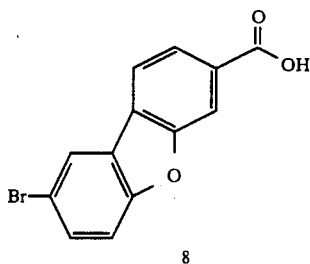

3-Bromo-dibenzofuran-7-carboxylic acid (8)

To a mixture of methyl 3-bromo-dibenzofuran-7-carboxylate (3.2 g, 10.5 mmol) in 2:1 THF:methanol (90 ml) was added 2.5N NaOH (60 ml). After stirring at room temperature for 1 hour, the reaction was complete. Nearly all the THF:methanol was evaporated off and then the mixture was adjusted to pH=1 with concentrated HCl and extracted with ethyl acetate. Drying (MgSO$_4$) and evaporation yielded 3.1 g (100%) of the title compounds which was used in the next reaction without purification.

$^1$H-NMR (300 MHz, d$_6$-DMSO): δ7.7–7.76 (m, 2H); 8.01 (dd, J=8.09, 1.34, 1H); 8.20 (bs, 1H); 8.30 (dd, J=8.18, 0.61, 1H); 8.54 (bs, 1H).

EXAMPLE 12

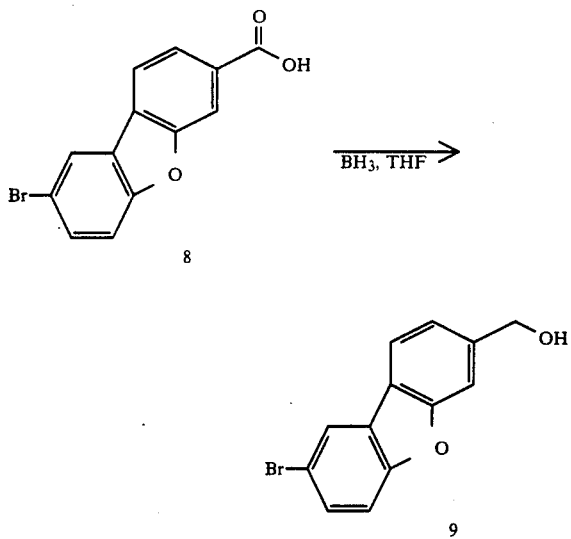

3-Bromo-7-(hydroxymethyl)-dibenzofuran (9)

A cloudy solution of 3-bromo-dibenzofuran-7-carboxylic acid (3.2 g, 10.9 mmol) in 80 ml THF was cooled to 0° C. and a solution of borane in THF (1.0M, 13.0 ml, 13.0 mmol) was added dropwise. The cooling bath was removed and the reaction was stirred at room temperature for 20 hours and was then quenched by the cautious addition of methanol (10 ml). The solution was evaporated to dryness in vacuo and the residue was dissolved in methanol-CH$_2$Cl$_2$ (1:1) and again evaporated. After one repetition of this dissolution-evaporation process, 2.74 g (90%) of the title compound was obtained as a brown solid and used in the next reaction without purification.

$^1$H-NMR (300 MHz, CDCl$_3$): δ4.85 (s, 2H); 7.33 (d, J=6.96, 1H); 7.41 (d, J=8.67, 1H); 7.52 (dd, J=8.76, 2.11, 1H); 7.58 (s, 1H); 7.85 (d, J=8, 1H); 8.03 (d, J=2.02, 1H).

EXAMPLE 13

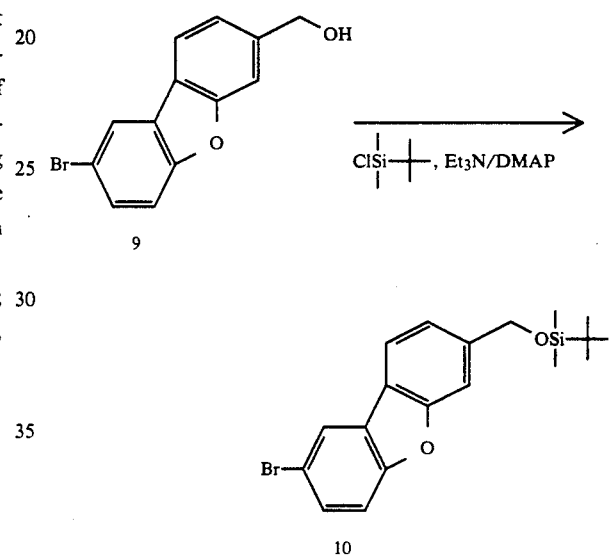

3-Bromo-7-(t-butyldimethylsilyloxymethyl)-dibenzofuran (10)

To a solution of 3-bromo-7-hydroxymethyl-dibenzofuran 9 (2.74 g, 9.9 mmol) and t-butyldimethylsilyl chloride (1.93 g, 12.8 mmol) in THF (60 ml) was added triethylamine (1.95 ml, 13.8 mmol) followed by 4-dimethylaminopyridine (120.7 mg, 0.99 mmol). After stirring at room temperature for 20 hours, the solution was poured into ethyl ether (180 ml) and washed successively with saturated NH$_4$Cl, saturated NaHCO$_3$, H$_2$O, and brine. Drying (MgSO$_4$) and evaporation gave a brown solid which was purified by flash chromatography through 100 g silica gel (10% CH$_2$Cl$_2$-hexane) to yield 3.2 g (82%) of the title compound as a pale yellow solid.

$^1$H-NMR (300 MHz, CDCl$_3$): δ0.11 (s, 6H), 0.953 (s, 9H); 4.88 (s, 2H); 7.26 (d, J=8.60, 1H); 7.41 (d, J=8.67, 1H); 7.5 (dd, J=8.0, 1.89, 1H); 7.56 (s, 1H); 7.82 (d, J=8.0, 1H); 8.02 (d, J=1.96, 1H).

EXAMPLE 14

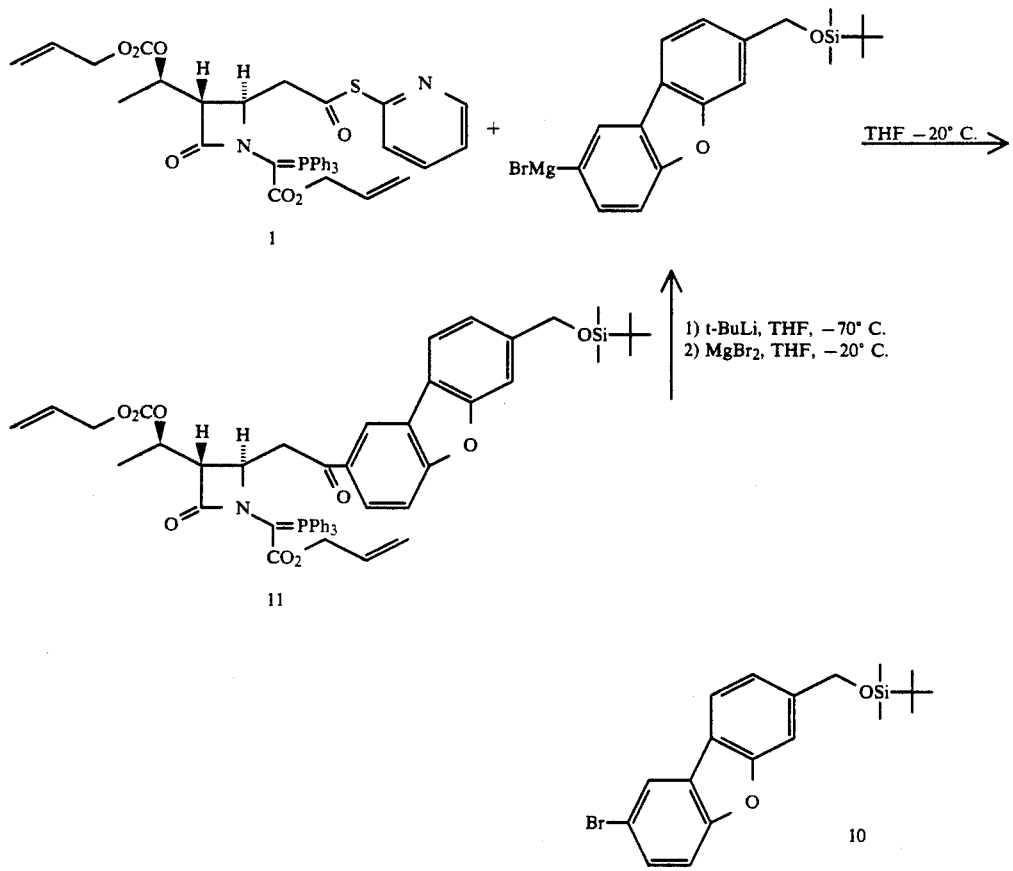

(3S,4R)-1-(allyloxycarbonyltriphenylphosphoranylidene)methyl-3-[1R-(allyloxycarbonyloxy)ethyl]-4-[2-(t-butyldimethylsilyloxymethyl)-6-dibenzofuranylcarbonyl]methyl-azetidin-2-one (11)

A solution of 3-bromo-7-(t-butyldimethylsilyloxymethyl)-dibenzofuran 10 (1.5 g, 3.8 mmol) in THF (12.9 ml) was cooled to −70° C. and a solution of t-butyllithium in pentane (1.7M, 4.47 ml, 7.79 mmol) was added. The solution was warmed to −20° C. over 15 minutes and then a solution of magnesium bromide in THF (0.25M, 16.7 ml) was added generating a reddish color. This Grignard solution was stirred at −20° C. for 20 minutes and was then added dropwise to a −70° C. solution of (3S,4R)-1-(allyloxycarbonyltriphenylphosphoranylidene)methyl-3-[1R-(allyloxycarbonyloxy)-ethyl)-4-[(2-pyridylthio)carbonyl]methyl-azetidin-2-one 1 (2.69 g, 3.80 mmol) in 13 ml in THF and allowed to warm to −20° C. over 20 minutes. The reaction was diluted into ethyl acetate washed successively with saturated NH$_4$Cl, 1N NaOH, H$_2$O, and brine. Drying (MgSO$_4$) and evaporation yielded 3.3 g of a yellow foam which was purified by flash chromatography through 250 g of silica gel (7:3 ethyl acetate:hexane) to yield 1.83 g (50%) of the title compound as a yellow foam.

IR (CHCl$_3$): 1740 (β-lactam), 1680 (ketone), 1610 cm$^{-1}$ (ylide).

$^1$H-NMR (300 MHz, CDCl$_3$): δ0.13 (s, 6H); 0.96 (s, 9H); 1.15 (d, J=6.22, 3H, CH$_3$).

EXAMPLE 15

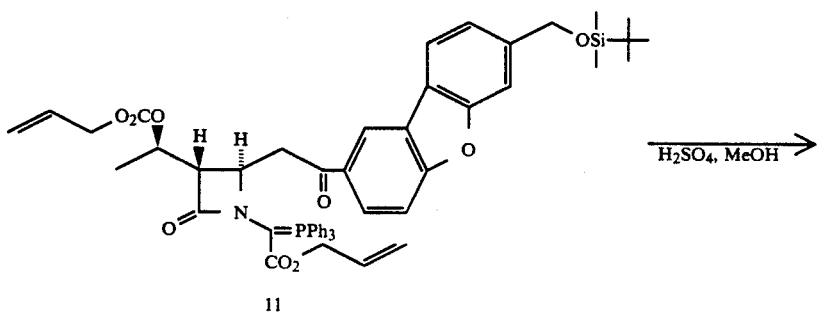

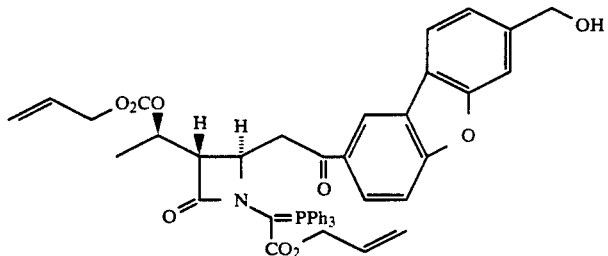

12

(3S,4R)-1-(allyloxycarbonyltriphenylphosphoranylidene)methyl-3-[1R-(allyloxycarbonyloxy)ethyl]-4-[2-(hydroxymethyl)-6-dibenzofuranylcarbonyl]-methyl-azetidin-2-one (12)

A solution of the silyl ether 11 (1.83 g, 1.9 mmol) in methanol (33 ml) was cooled to 0° C. and 1M H$_2$SO$_4$ (2.85 ml, 2.85 mmol) was added. The reaction was stirred at 0° C. for 1.5 hours, quenched with NaHCO$_3$, diluted into ethyl acetate and washed successively with saturated NaHCO$_3$, water and brine. Drying (MgSO$_4$) and evaporation yielded 1.8 g of a yellow solid which was purified by flash chromatography through 200 g silica gel (7:3 ethyl acetate:hexanes) yielding 1.1 g (82%) of the title compound.

IR (CHCl$_3$): 1740 (β-lactam), 1680 (ketone), 1610 cm$^{-1}$ (ylide).

$^1$H-NMR (300 MHz, CDCl$_3$) 1.15 (d, J=6.35, 3H, CH$_3$).

EXAMPLE 16 purified by flash chromatography through 50 g silica gel (7:3 ethyl acetate:hexanes) yielding 240 mg (46%) of the title compound as a yellow foam. IR (CHCl$_3$): 1780 (β-lactam), 1740 (carbonate) 1725 cm$^{-1}$ (ester).

$^1$H-NMR (300 MHz, CDCl$_3$): δ1.48 (d, J=6.41, 3H, —CH$_3$); 3.27-3.33 (m, 2H, H1ab); 3.42 (dd, J=8.39, 2.79, 1H, H6); 4.30 (dt, J=2.74, 9.38, 1H, H5); 4.57–4.75 (m, 4H, —OCH$_2$C═C); 4.82 (s, 2H, —CH$_2$—O); 5.11–5.38 (m, 5H, H8, —C═CH$_2$); 5.77–5.94 (m, 2H, —CH═C); 7.30 (d, J=7.94, 1H); 7.41–7.50 (m, 2H); 7.56 (s, 1H); 7.84 (d, J=8.0, 1H); 7.91 (s, 1H).

EXAMPLE 17

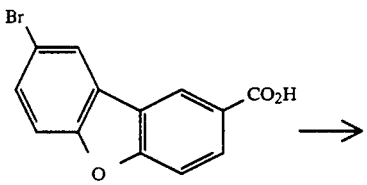

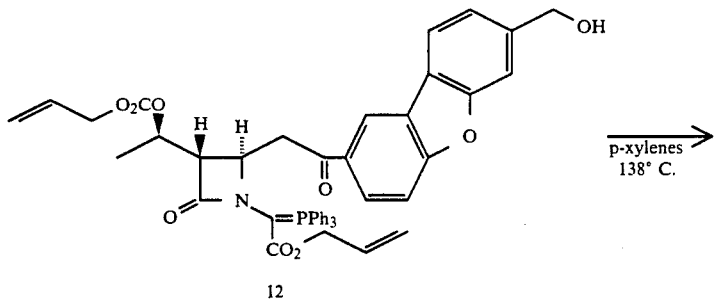

12 p-xylenes
138° C.

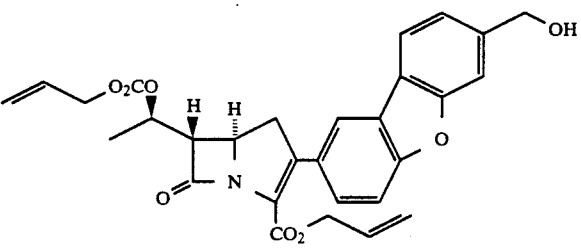

13

Allyl-(5R,6S)-2-(2-hydroxymethyl-6-dibenzofuranyl)-6-[1R-(allyloxycarbonyloxy)ethyl]-carbapen-2-em-3-carboxylate (13)

The phosphorane 12 (0.551 g, 0.693 mmol) was dissolved in p-xylenes (34.6 ml) in the presence of one crystal of hydroquinone and refluxed for 2 hours. Evaporation yielded 540 mg of a yellow solid which was

EXAMPLE 18

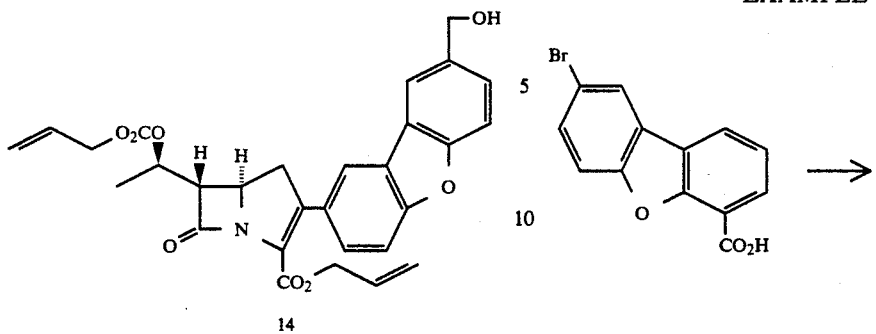

Allyl-(5R,6S)-2-(3-hydroxymethyl-6-dibenzofuranyl)-6-[1R-(allyloxycarbonyloxy)ethyl]-carbapen-2-em-3-carboxylate (14)

In an analogous manner to that described in Examples 12–16, but starting with 3-bromo-dibenzofuran-6-carboxylic acid [H. Gilman et. al., J. Amer. Chem. Soc. 61, 2836 (1939)], the title compound was obtained as a yellow foam.

IR (CHCl$_3$): 1780 ($\beta$-lactam), 1745 (carbonate), 1720 cm$^{-1}$ (ester).

$^1$H-NMR (300 MHz:CDCl$_3$): $\delta$1.49 (d, J=6.35, 3H, —CH$_3$); 3.31–3.34 (m, 2H, H1a,b); 3.43 (dd, J=8.48, 2.74, 1H, H6); 4.29 (dt, J=2.75, 9.35, 1H, H5); 4.58–4.75 (m, 4H, C=C—CH$_2$O); 4.82 (d, J=5.07, 2H, Ar—CH$_2$O—); 5.13–5.39 (m, 5H, H8, CH$_2$=C—); 5.79–5.94 (m, 2H, C=CH—); 7.43–7.95 (m, 6H, ArH).

Allyl-(5R,6S)-2-(1-hydroxymethyl-6-dibenzofuranyl)-6-[1R-(allyloxycarbonyloxy)ethyl]-carbapen-2-em-3-carboxylate (15)

In an analogous manner to that described in Examples 12–16, but starting with 6-bromo-dibenzofuran-1-carboxylic acid [H. Gilman et. at., J. Amer. Chem. Soc. 61, 643 (1939)], the title compound was obtained as a yellow foam.

IR (CHCl$_3$): 1780 ($\beta$-lactam), 1745 (carbonate), 1720 cm$^{-1}$ (ester).

$^1$H-NMR (300 MHz, CDCl$_3$) $\delta$1.48 (d, J=6.35, 3H, —CH$_3$); 3.29–3.34 (m, 2H, H1a,b); 3.42 (dd, J=8.36, 2.69, 1H, H6); 4.28 (dt, J=2.44, 9.22, 1H, H5); 4.57–4.70 (m, 4H, C=C—CH$_2$—); 5.05 (s, 2H, Ar—CH$_2$—O); 5.12–5.38 (m, 5H, H8, CH$_2$=C—); 5.77–5.93 (m, 2H, C=CH—); 7.34 (t, J=7.81, 1H); 7.43–7.54 (m, 3H); 7.82 (d, J=7.69, 1H); 7.94 (s, 1H).

EXAMPLE 19

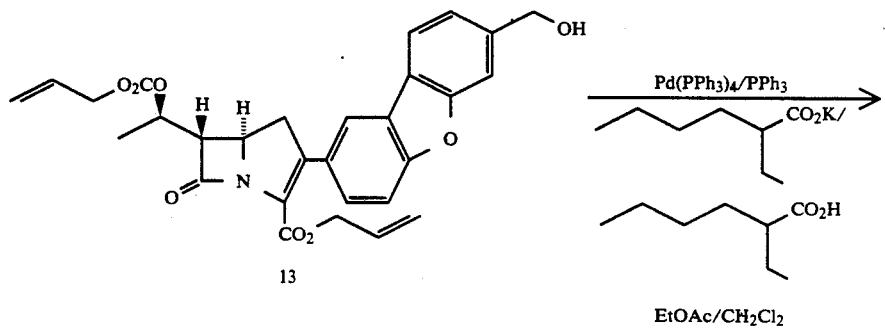

EtOAc/CH$_2$Cl$_2$

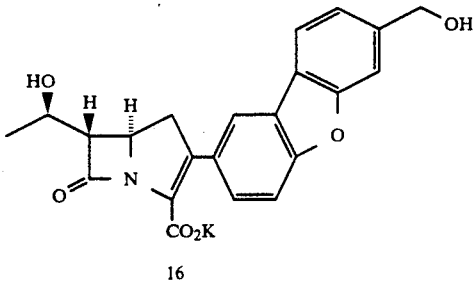

16

Potassium (5R,6S)-2-(2-hydroxymethyl-6-dibenzofuranyl)-6-(1R-hydroxyethyl)-carbapen-2-em-3-carboxylate (16)

To a solution of the carbapenem 13 (41 mg, 0.079 mmol), potassium 2-ethylhexanoate (0.5M in ethyl acetate, 0.158 ml), 2-ethylhexanoic acid (1M in methylene chloride, 0.079 ml) and triphenylphosphine (6.2 mg, 0.023 mmol) in 1:1 ethyl acetate-methylene chloride (1 ml) was added tetrakis (triphenylphosphine) palladium (9.1 mg, 0.0079 mmol) and the mixture was sonicated for 30 seconds in an ultrasonic bath and then stirred at 0° C. for 1 hour. During this time a tan precipitate formed. The mixture was added dropwise to ice cold ether (4 ml) and the precipitate was collected by centrifugation and washed with ethyl ether to give 41 mg of a tan solid. After drying under vacuum, this solid was purified by reverse phase prep tlc (4:1 $H_2O:CH_3CN$) to yield 16.6 mg (48%) of the title compound as a lyophilized solid.

UV ($H_2O$): $\lambda max = 291$ nm (68 =23,000).

IR (KBr): 1750 ($\beta$-lactam), 1590 cm$^{-1}$ (carboxylate).

$^1$H-NMR (300 MHz, 2:1 $D_2O:CD_3CN$) $\delta$1.68 (d, J=6.04, 3H, —CH$_3$), 3.52 (dd, J=9.55, 16.70, 1H, H1a); 3.82-3.93 (m, 2H, H1b, H6); 4.59-4.71 (m, 2H, H8, H5); 5.15 (s, 2H, —CH$_2$—O); 7.79 (d, J=7.57, 1H); 7.95-8.01 (m, 3H), 8.43-8.45 (m, 2H).

EXAMPLE 20

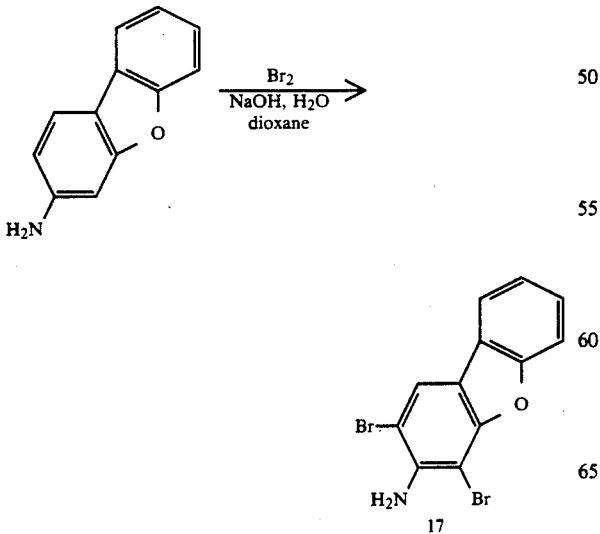

2-Amino-1,3-dibromodibenzofuran (17)

A suspension of 2-aminodibenzofuran [59.3 g, 0.324 mol; H. Gilman and S. Avakian, *J. Am. Chem. Soc.* 68, 580 (1946)] in 1.3 l of dioxane and 340 ml of 2N sodium hydroxide was cooled to 0° C. Bromine (109 g, 680 mmol) was added dropwise over 1 hour, after which time the reaction mixture had turned very dark and was allowed to stir at room temperature for 1 hour. The solution was then evaporated to a volume of 500 ml and extracted with methylene chloride (2 l). The organic layers were combined, dried over MgSO$_4$ and filtered through 1 kg of silica gel (methylene chloride), evaporated to dryness and again filtered through 1 kg of silica gel yielding 98 g (89%) of the title compound as a dark solid.

$^1$H-NMR (300 MHz, CDCl$_3$): $\delta$4.76 (bs, 2H); 7.21-7.39 (m, 2H); 7.54 (d, J=7.70, 1H); 7.54 (d, J=7.39, 1H); 7.93 (s, 1H).

FAB-MS: M/e=339, 341, 343 (M$^+$).

EXAMPLE 21

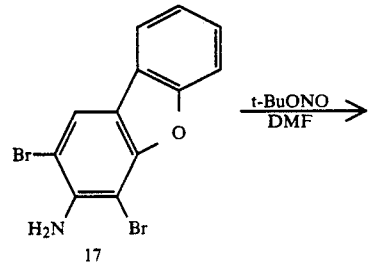

1,3-Dibromodibenzofuran (18)

To a solution of t-butylnitrite (0.89 ml, 7.2 mmol) dissolved in 10 ml of DMF at 50° C. was added dropwise a solution of 2-amino-1,3-dibromodibenzofuran 17 (1.0 g, 2.9 mmol) in 10 ml of DMF with nitrogen evolution. After stirring at 50° C. for 1 hour the reaction was diluted into ether and washed successively with H$_2$O and saturated NaCl. Drying over MgSO$_4$ and evaporation gave 1.1 g of a red solid which was purified by flash chromatography through 100 g of silica gel (20% methylene chloride: hexane) yielding 650 mg (68%) of the title compound as a pale orange solid.

$^1$H-NMR (300 MHz, CDCl$_3$): δ7.37 (t, J=7.69, 1H); 7.51 (t, J=7.14, 1H); 7.63 (d, J=8.25, 1H), 7.73 (d, J=1.77, 1H), 7.88 (d, J=7.57, 1H); 7.99 (s, 1H).

EI-MS: M/e=324, 326, 328 (M+).

EXAMPLE 22

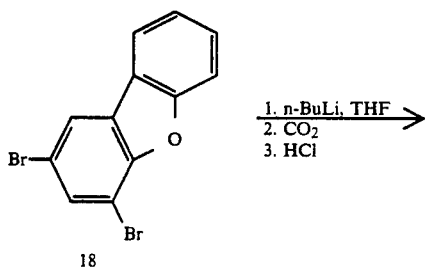

3-Bromodibenzofuran-1-carboxylic acid (19)

A solution of 1,3-dibromodibenzofuran 18 (2.4 g, 7.4 mmol) in 250 ml of THF was cooled to −70° C. and a solution of n-butyllithium in hexane (2.2M, 4.0 ml, 8.8 mmol) was added dropwise generating a red color. The solution was allowed to warm to −50° C. over 30 minutes and then CO$_2$ gas was bubbled into the reaction mixture for 30 minutes. The cooling bath was removed and after stirring at room temperature for 30 minutes, most of the THF was evaporated off and the reaction mixture was diluted with methylene chloride (1000 ml) and extracted with sodium hydroxide (1N). The aqueous layer was brought to pH 3 with concentrated hydrochloric acid, and then extracted with methylene chloride (1000 ml).

Evaporation of the organic phase gave 2.0 g (91%) of the title compound as a yellow solid which was used without purification.

$^1$H-NMR (300 MHz, d$_6$-Acetone): δ7.49 (t, J=7.4 Hz, 1H); 7.65 (t, J=7.5 Hz, 1H); 7.75 (d, J=8.1 Hz, 1H); 8.19 (d, J=2.1 Hz, 1H); 8.24 (d, J=7.6, 1H); 8.60 (d, J=2.1 Hz, 1H).

FAB-MS: M/e=291, 293 (M+H).

EXAMPLE 23

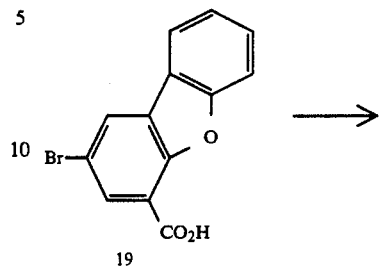

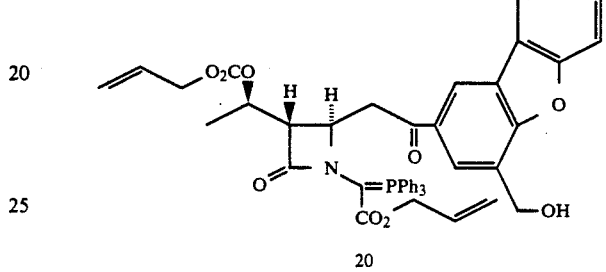

(3S,4R)-1-(allyloxycarbonyltriphenylphosphoranylidene)methyl-3-[1R-(allyloxycarbonyloxy)ethyl]-4-[1-hydroxymethyl-3-dibenzofuranylcarbonyl]-methylazetidin-2-one (20)

In an analogous manner to that described in Examples 12-15, but starting with 3-bromodibenzofuran-1-carboxylic acid 19, the title compound was obtained as a yellow foam.

IR (CHCl$_3$): 1750 (β-lactam); 1665 (ketone); 1620 cm$^{-1}$ (ylide).

EXAMPLE 24

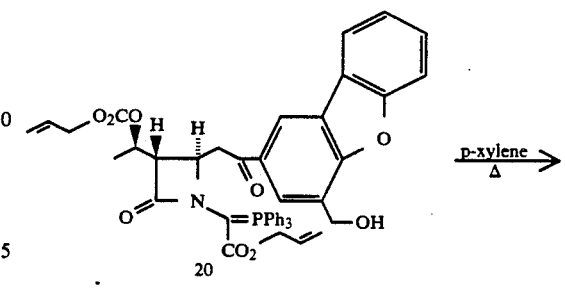

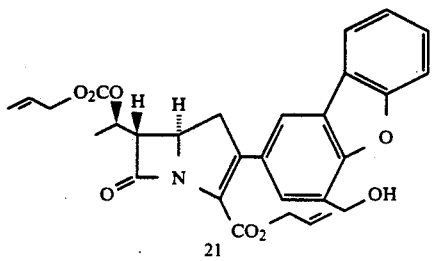

Allyl-(5R, 6S)-2-(1-hydroxymethyl-3-dibenzofuranyl)-6-[1R-(allyloxycarbonyloxy)ethyl]-carbapen-2-em-3-carboxylate (21)

In a manner analogous to that described in Example 16, 1.04 g (1.3 mmol) of ylide 20 was cyclized to yield 0.70 g (99%) of the title compound as a yellow oil.

IR (CHCl$_3$): 1780 ($\beta$-lactam); 1740 (carbonate); 1720 cm$^{-1}$ (ester).

$^1$H-NMR (300 MHz, CDCl$_3$): $\delta$1.47 (d, J=6.28 Hz, 3H, —CH$_3$); 3.25–3.37 (m, 2H, H1a,b); 3.41 (dd, J=2.7, 8.3, 1H, H6); 4.28 (dt, J=2.7, 9.47, 1H, H5); 4.56–4.73 (m, 4H, C=C—CH$_2$—); 5.01 (d, J=6.05, 2H, Ar—CH$_2$—O); 5.10–5.38 (m, 5H, H8, CH$_2$=C—); 5.77–5.93 (m, 2H, C=CH—); 7.33 (t, J=7.5, 1H); 7.45 (t, J=7.3, 1H); 7.49 (s, 1H); 7.55 (d, J=8.1, 1H); 7.85–7.89 (m, 2H).

EXAMPLE 25

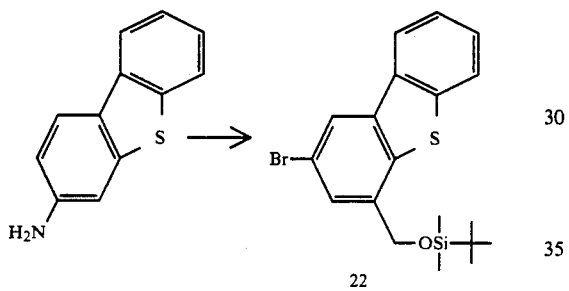

3-Bromo-1-(t-butyldimethylsilyloxymethyl)-dibenzothiophene (22)

In an analogous manner to that described in Examples 20–22, 12 and 13, 2-aminodibenzothiophene [R. K. Brown et al., J. Am. Chem. Soc., 70, 1748 (1948)] was converted to the title compound which was obtained as a yellow solid.

$^1$H-NMR (300 MHz, CDCl$_3$): $\delta$0.19 (s, 6H); 1.01 (s, 9H); 4.91 (s, 2H); 7.4–7.5 (m, 2H); 7.60 (s, 1H); 7.80–7.85 (m, 1H); 8.0–8.1 (m, 1H); 8.13 (d, J=1.8 Hz, 1H).

FAB-MS: M/e=406, 408 (M+).

EXAMPLE 26

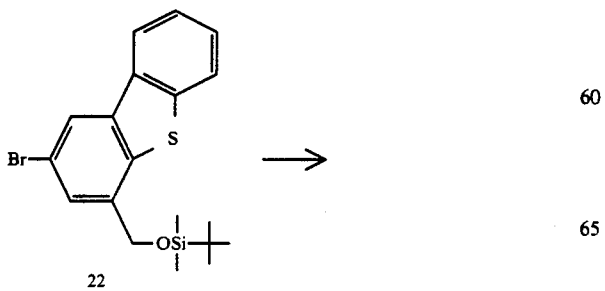

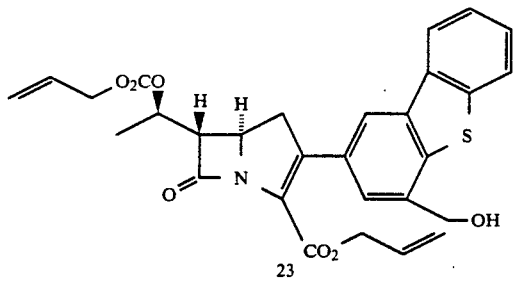

Allyl-(5R, 6S)-2-(1-hydroxymethyl-3-dibenzothienyl)-6-[1R-(allyloxycarbonyloxy)ethyl]-carbapen-2-em-3-carboxylate (23)

In an analogous manner to that described in Examples 14–16, but starting with 3-bromo-1-(t-butyldimethylsilyloxymethyl)-dibenzothiophene 22, the title compound was obtained as a yellow foam.

$^1$H-NMR (300 MHz, CDCl$_3$): $\delta$1.48 (d, J=6.41 Hz, CH$_3$); 3.25–3.45 (m, 2H, H1); 3.43 (dd, J=2.8, 8.4 Hz 1H, H6); 4.31 (dt, J=2.8, 9.3 Hz, 1H, H5); 4.55–4.75 (m, 4H, —OCH$_2$C=C); 4.93 (d, J=5.7 Hz, 2H, Ar—CH$_2$—O); 5.1–5.4 (m, 5H, H8, —C=CH$_2$); 5.75–6.0 (m, 2H, —CH=C); 7.4–7.5 (m, 3H); 7.8–7.9 (m, 1H); 8.05–8.15 (m, 2H). IR (CHCl$_3$): 1780 ($\beta$-lactam); 1745 (carbonate); 1720 cm$^{-1}$ (ester).

UV (CH$_3$CN): $\lambda_{max}$=325 nm ($\epsilon$=11,600).

EXAMPLE 27

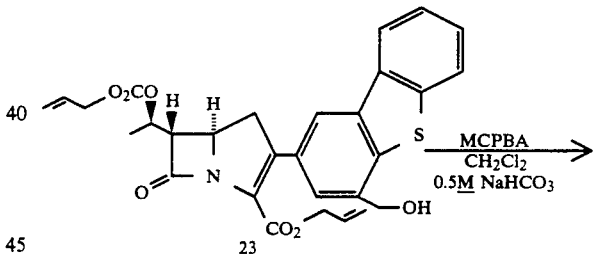

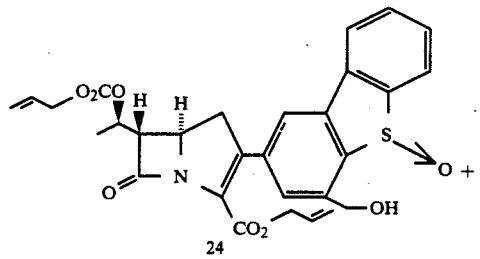

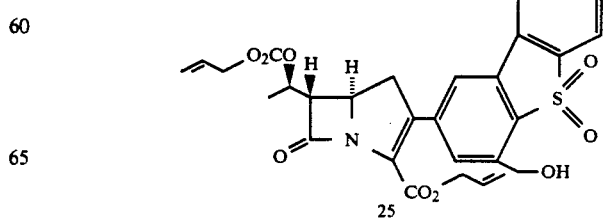

Allyl-(5R, 6S)-2-(1-hydroxymethyl-9-oxo-3-dibenzothienyl)-6-[1R-(allyloxycarbonyloxy)ethyl]-carbapen-2-em-3-carboxylate (24) and allyl-(5R, 6S)-2-(1-hydroxymethyl-9,9-dioxo-3-dibenzothienyl-6-[1R-(allyloxycarbonyloxy)ethyl]-carbapen-2-em-3-carboxylate (25)

A solution of the carbapenem 23 (272.4 mg, 0.510 mmol) in 5 ml of methylene chloride and 2.5 ml of 0.5M aqueous sodium bicarbonate was cooled to 0° C. and 99% m-chloroperbenzoic acid (115 mg, 0.67 mmol, 1.3 equiv.) was added in one portion. The two-phase reaction mixture was vigorously stirred for 30 minutes and was then quenched with 5% aqueous $Na_2S_2O_3$ and stirred until a negative starch-iodide test was obtained. The reaction mixture was diluted with ethyl acetate and washed with $H_2O$ and brine. Drying over $MgSO_4$ and evaporation gave a yellow oil which was separated by flash chromatography through 30 g of silica gel (EtOAc) to yield 203 mg (72%) of the sulfoxide 24 as a yellow oil and a mixture of the less polar sulfone and unreacted starting material. The latter mixture was further separated by preparative TLC on silica gel (1:1 EtOAc/hexane) to yield 27 mg (9.4%) of the sulfone 25 and 8.5 mg (3.0%) of recovered starting material.

Sulfoxide 24

$^1$H-NMR (300 MHz, $CDCl_3$): δ1.49 (d, J=6.29 Hz, 3H, $CH_3$); 3.20–3.45 (m, 2H, H1); 3.46 (dd, J=2.9. 8.3 Hz, 1H, H6); 4.34 (dt, J=2.9, 9.3 Hz, 1H, H5); 4.55–4.75 (m, 4H, —$OCH_2C$≡C); 4.87 (dd, J=9.0, 13.6 Hz, 1H, Ar—$CH_A$—O—); 5.1-5.4 (m, 6H, H8, Ar—$CH_B$—O—, —C≡$CH_2$); 5.75–6.0 (m, 2H, —CH≡C); 7.37 (d, J=8.2 Hz, 1H); 7.53 (t, J=7.7 Hz, 1H); 7.62 (t, J=7.5 Hz, 1H); 7.7–7.8 (m, 2H); 7.99 (d, J=7.2 Hz, 1H).

Sulfone 25

$^1$H-NMR (300 MHz, $CDCl_3$): δ1.47 (d, J=6.35 Hz, 3H, $CH_3$); 3.25–3.45 (m, 2H, H1); 3.47 (dd, J=2.9, 8.2 Hz, 1H, H6); 4.33 (dt, Jq32 2.9, 9.4 Hz, 1H, H5); 4.55–4.75 (m, 4H, —$OCH_2C$≡C); 5.07 (d, J=6.29, 2H, Ar—$CH_2O$—); 5.1–5.4 (m, 5H, H8, —C≡$CH_2$); 5.75–6.0 (m, 2H, —CH≡C); 7.52 (bs, 1H); 7.54 (d, J=7.6, 1H); 7.63 (t, J=7 Hz, 1H); 7.70 (s, 1H); 7.73 (d, J=7.6 Hz, 1H); 7.80 (d, J=7.7 Hz, 1H).

EXAMPLE 28

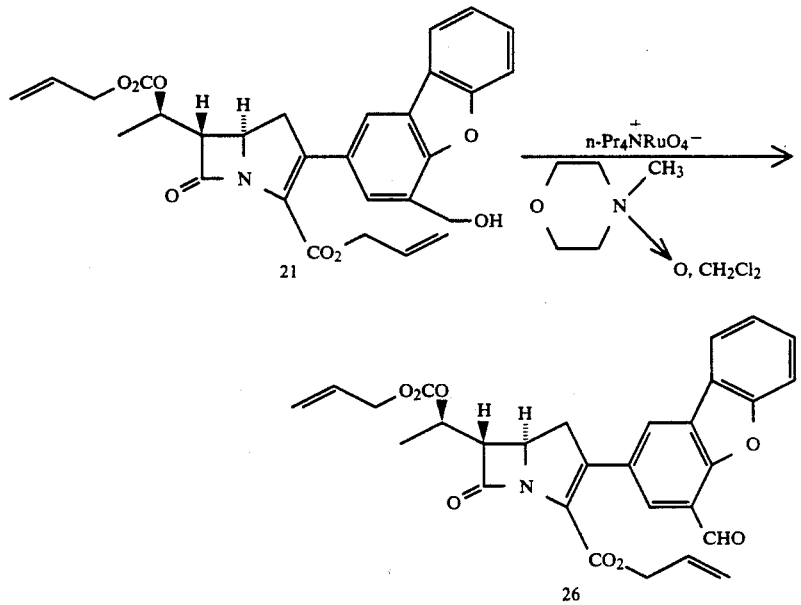

Allyl-(5R,6S)-2-(1-formyl-3-dibenzofuranyl)-6-[1R-(allyloxycarbonyloxy)ethyl]-carbapen-2-em-3-carboxylate (26)

To a solution of the alcohol 21 (271.9 mg, 0.525 mmol) in 7 ml of methylene chloride were added N-methylmorpholine-N-oxide (90.7 mg, 0.788 mmol) and powdered 3 Å molecular sieves (45 mg). The mixture was stirred at room temperature for 10 minutes and then tetra-n-propylammonium peruthenate (18.4 mg, 0.053 mmol) was added. After 20 minutes more, the reaction mixture was filtered through 30 g of silica gel, eluting with 9:1 ethyl acetate-methylene chloride. Evaporation of the filtrate yielded 223 g (82%) of the title compound as a yellow oil.

$^1$H-NMR (300 MHz, $CDCl_3$): δ1.50 (d. J=6.41 Hz, 3H, $CH_3$); 3.25–3.45 (m, 2H, H1); 3.46 (dd, J=2.8, 8.3 Hz, 1H, H6); 4.34 (dt, J=2.8, 9.3 Hz, 1H, H5); 4.55–4.75 (m, 4H, —$OCH_2C$≡C); 5.1–5.4 (m, 5H, H8, —C≡$CH_2$); 5.75–6.0 (m, 2H, —CH≡C); 7.4 (t, J=8 Hz, 1H);, 7.55 (t, J=7.5 Hz, 1H); 7.69 (d, J=8 Hz, 1 Hz); 7.93 (d, J=2 Hz, 1H); 7.95 (d, J=9 Hz, 1H); 8.25 (d, J=2 Hz, 1H); 10.57 (s, 1H).

IR ($CHCl_3$): 1780 (β-lactam); 1745 (carbonate); 1725 (ester); 1695 cm$^{-1}$ (aldehyde).

UV ($CH_3CN$): $\lambda_{max}$=300 nm (ε=15,700).

EXAMPLE 29

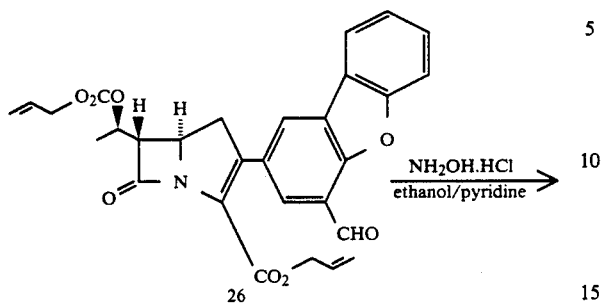

Allyl-(5R,6S)-2-(1-oximino-3-dibenzofuranyl)-6-[1R-(allyloxycarbonyloxy)ethyl]-carbapen-2-em-3-carboxylate (27)

To a solution of the aldehyde 26 (75 mg, 0.145 mmol) in ethanol (0.8 ml) and pyridine (0.8 ml) at 0° C. was added hydroxylamine hydrochloride (9.9 mg, 0.15 mmol). After 5 minutes the reaction mixture was diluted with ethyl acetate and washed successively with saturated NH4Cl, saturated NaHCO3 and H2O. Drying over MgSO4 and evaporation gave an oil which was purified by flash chromatography through 10 g of silica gel (7:3 ethyl acetate/hexane) to yield 71 mg (92%) of the title compound as a yellow oil. $^1$H-NMR (300 MHz, CDCl3): δ1.49 (d, J=6.25 Hz, 3H, CH3); 3.25-3.45 (m, 2H, H1); 3.44 (dd, J=2.7, 8.5 Hz, 1H, H6); 4.32 (dt, d=2.7, 9.1 Hz, 1H, H5); 4.5-4.8 (m, 4H, —OCH2C=C): 5.1-5.4 (m, 5H, H8, —C=CH2); 5.75-6.0 (m, 2H, —CH=C); 7.37 (t, J=7.6 Hz, 1H), 7.5 (t, J=7.1 Hz, 1H); 7.64 (d, J=8.2 Hz, 1H); 7.7 (s, 1H), 7.91 (d, J=7.7 Hz, 1H); 7.98 (s, 1H); 8.56 (s, 1H); 8.6 (bs, 1H).

IR (CHCl3): 3330 (hydroxyl); 1780 (β-lactam); 1745 (carbonate); 1725 cm$^{-1}$ (ester).

UV (CH3CN): λ$_{max}$=297 nm (ε=10,000).

EXAMPLE 30

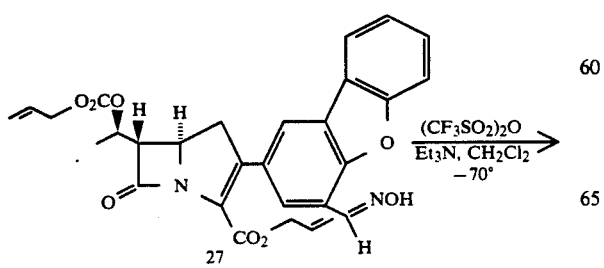

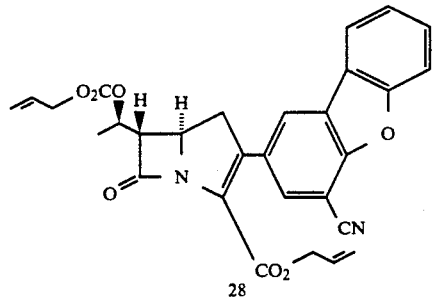

Allyl-(5R,6S)-2-(1-cyano-3-dibenzofuranyl)-6-[1R-allyloxycarbonyloxy)ethyl]-carbapen-2-em-3-carboxylate (28)

To a solution of the oxime 27 (70 mg, 0.13 mmol) in methylene chloride was cooled to −70° C. and triethylamine (0.039 ml, 0.28 mmol) was added followed by triflic anhydride (0.022 ml, 0.13 mmol). After 5 minutes, the red reaction mixture was diluted into ethyl acetate and the solution was washed successively with saturated NH4Cl, saturated NaHCO3, H2O, and brine. Drying over MgSO4 and evaporation gave an oil which was purified by flash chromatography through 7 g of silica gel (7:3 ethyl acetate/hexane) to yield 52.5 mg (77%) of the title compound as a yellow foam.

$^1$H-NMR (300 MHz, CDCl3): δ1.49 (d, J=6.41 Hz, 3H, CH3); 3.25-3.45 (m, 2H, H1); 3.46 (dd, J=2.9, 8.4 Hz, 1H, H6), 4.35 (dt, J=2.9, 9.2 Hz, 1H, H5); 4.55-4.80 (m, 4H, —OCH2C=C); 5.1-5.4 (m, 5H, H8, —C=CH2); 5.75-6.0 (m, 2H, —CH=C), 7.4 (t, J=7.6, 1H); 7.56 (t, J=8.5 Hz, 1H); 7.67 (d, J=8.2 Hz, 1H); 7.71 (d, J=1.7 Hz, 1H); 7.93 (d, J=7.7 Hz, 1H); 8.18 (d, J=1.7 Hz, 1H).

IR (CHCl3): 2240 (nitrile; 1780 (β-lactam); 1740 (carbonate); 1725 cm$^{-1}$ (ester).

UV (CH3CN): λ$_{max}$=295 nm (ε=17,200).

EXAMPLE 31

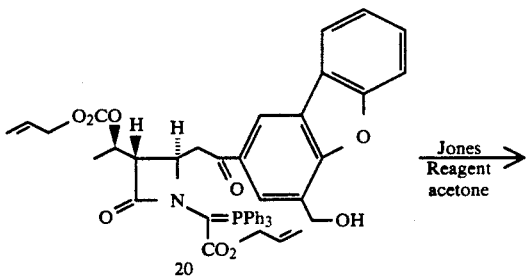

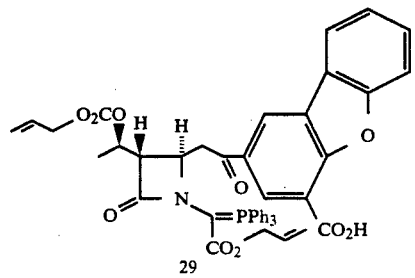

(3S,4R)-1-(allyloxycarbonyltriphenylphosphoranylidene)methyl-3-[1R-(allyloxycarbonyloxy)ethyl]-4-(1-carboxy-3-dibenzofuranylcarbonyl)methylazetidin-2-one (29)

A solution of the alcohol 20 (1.00 g, 1.22 mmol) in acetone (24 ml) was cooled to 0° C. and a solution of 2N Jones Reagent (1.8 ml, 3 equiv.) was added. The reaction mixture was stirred at 0° C. for 40 minutes and was then quenched with isopropyl alcohol and dried over Na$_2$SO$_4$. Filtration and evaporation gave a green solid which was purified by flash chromatography through 100 g of silica gel (15% methanol-ethyl acetate, 0.1% acetic acid) yielding 1.0 g (99%) of the title compound as a yellow foam.

IR (CHCl$_3$): 1745 (β-lactam); 1720 (carbonate); 1680 (ketone) 1610 cm$^{-1}$ (ylide, carboxylic acid).

EXAMPLE 32

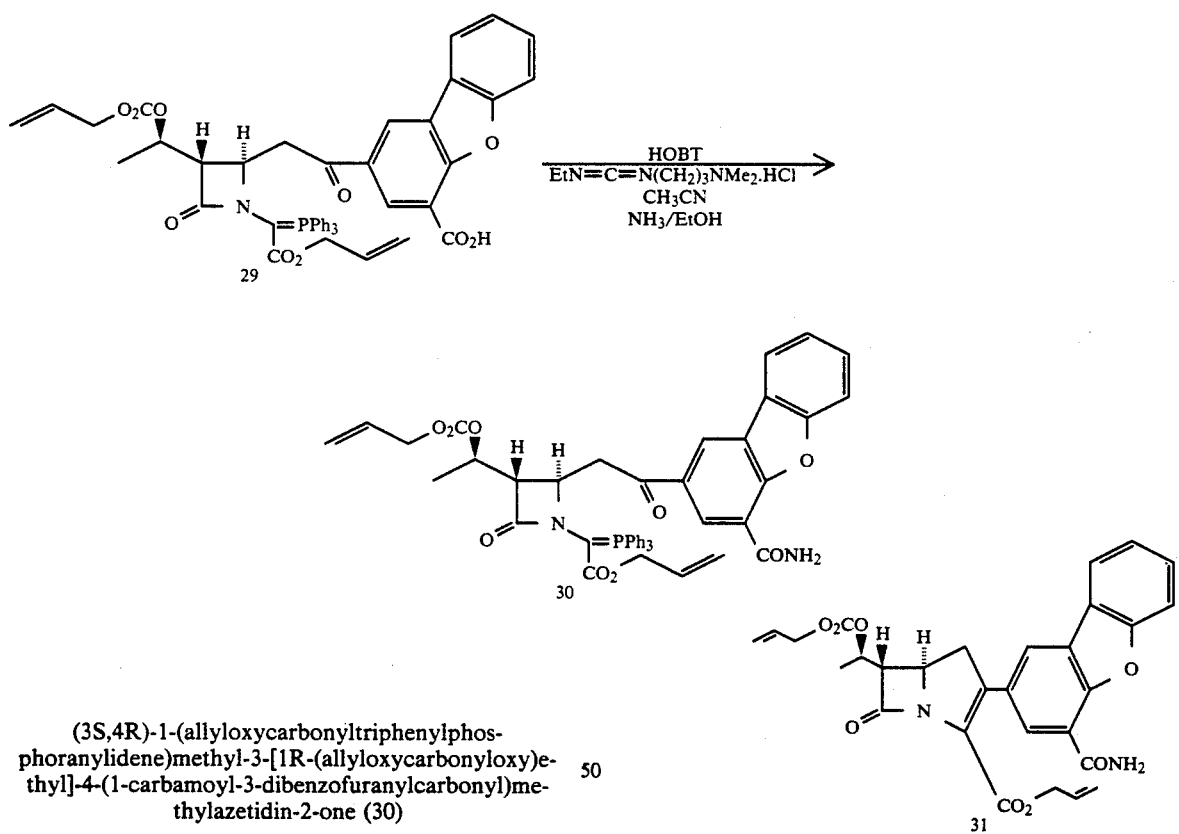

(3S,4R)-1-(allyloxycarbonyltriphenylphosphoranylidene)methyl-3-[1R-(allyloxycarbonyloxy)ethyl]-4-(1-carbamoyl-3-dibenzofuranylcarbonyl)methylazetidin-2-one (30)

To a solution of the carboxylic acid 29 (169 mg, 0.208 mmol) in acetonitrile (3 ml) was added 1-(3-dimethylaminopropyl)-3-ethylcarbodiimide hydrochloride (51.8 mg, 0.270 mmol) and 1-hydroxybenzotriazole hydrate (53.5 mg, 0.395 mmol) dissolved in THF (3 ml). The solution was stirred at room temperature for 20 minutes and then a solution of ammonia in ethanol (61 mg/ml, 1.5 ml) was added generating an orangish color and a small amount of precipitate. After stirring at room temperature for 20 minutes, the reaction mixture was evaporated to dryness giving a dark yellow solid which was purified by flash chromatography through 16 g of silica gel (7:2.5:5 ethyl acetate: hexane: methanol) yielding 116 mg (69%) of the title compound as a yellow oil.

IR (CHCl$_3$): 1740 (β-lactam); 1680 (ketone, amide); 1610 cm$^{-1}$ (ylide).

EXAMPLE 33

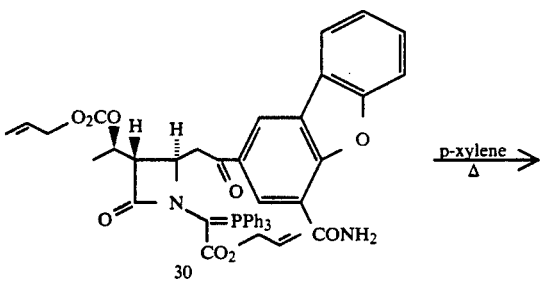

Allyl-(5R,6S)-2-(1-carbamoyl-3-dibenzofuranyl)-6-[1R-(allyloxycarbonyloxy)ethyl]-carbapen-2-em-3-carboxylate (31)

In a manner analogous to that described in Example 16, the ylide 30 (154 mg, 0.19 mmol) was cyclized to yield the title compound (83 mg, 84%) as a yellow foam.

IR (CHCl$_3$): 3510, 3400 (—NH$_2$); 1780 (β-lactam); 1740 (carbonate); 1720 (ester); 1680 cm$^{-1}$ (amide).

UV (acetonitrile): λ$_{max}$=297 nm (ε=18,600).

$^1$H-NMR (300 MHz, CDCl$_3$): δ1.49 (d, J=6.29 Hz, 3H, —CH$_3$); 3.34–3.37 (m, 2H, H1a,b); 3.44 (dd, J=2.8, 8.24, 1H, H6); 4.33 (dt, J=2.8, 9.34, 1H, H5); 4.58–4.75 (m, 4H, C=C—CH$_2$—); 5.11–5.39 (m, 5H, H8,

CH$_2$=C—); 5.78-5.94 (m, 2H, C=—CH—); 6.17 (s, 1H, NH); 7.40 (t, J=7.6, 1H); 7.49-7.54 (m, 3H); 7.60 (d, J=8.2, 1H); 7.94 (d, J=7.7, 1H), 8.19 (s, 1H).

EXAMPLE 34

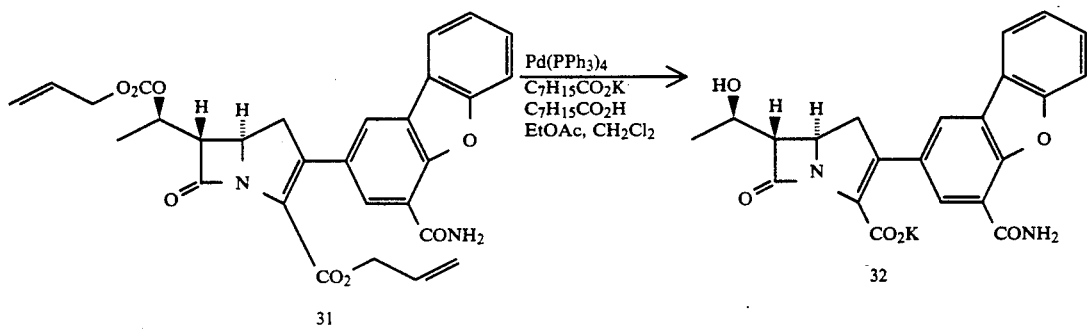

Potassium (5R,6S)-2-(1-carbamoyl-3-dibenzofuranyl)-6-(1R-hydroxyethyl)-carbapen-2-em-3-carboxylate (32)

In an analogous manner to that described in Example 19, 83 mg (0.16 mmol) of carbapenem 31 was deprotected to yield 35 mg (50%) of the title compound as an off-white lyophilized solid.

IR (KBr): 1750 (β-lactam); 1660 (amide); 1600 cm$^{-1}$ (carboxylate).

UV (H$_2$O): $\lambda_{max}$=297 nm ($\epsilon$=20,000).

$^1$H-NMR (300 MHz, 2:1 D$_2$O:CD$_3$CN): δ1.67 (d, J=6.47 Hz, 3H, —CH$_3$); 3.52 (dd, J=9.65, 16.7, 1H, H1a); 3.82-3.92 (m, 2H, H1b, H6); 4.57-4.71 (m, 2H, H8 H5); 7.83 (t, J=7.7, 1H); 7.96 (t, J=7.3, 1H); 8.07 (d, J=7.94, 1H); 8.34 (s, 1H); 8.46 (d, J=7.7, 1H); 8.60 (d, J=1.6, 1H).

EXAMPLE 35

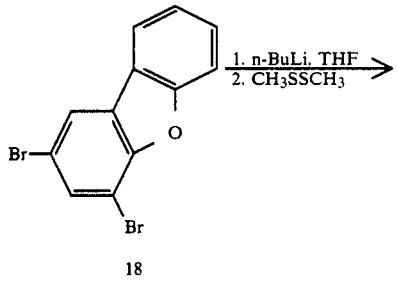

3-Bromo-1-methylthio-dibenzofuran

A solution of 1,3-dibromodibenzofuran 18 (0.500 g, 1.54 mmol) in THF (53 ml) was cooled to −70° C. and a solution of n-butyllithium in hexane (2.2M, 0.84 ml, 1.8 mmol) was added dropwise. The resulting red solution was allowed to warm to −50° C. over 30 minutes. Methyl disulfide (0.162 ml, 1.84 mmol) was added and the solution was allowed to warm to −10° C. After stirring for 20 minutes, the solution was poured into ethyl acetate and washed successively with 1N NaOH, H$_2$O, and brine. Drying over MgSO$_4$ and evaporation gave a tan solid which was purified by flash chromatography through 40 g of silica gel (10% CH$_2$Cl$_2$-hexane) to yield 394 mg (87%) of the title compound as a white powder.

$^1$H-NMR (300 MHz, CDCl$_3$): δ7.86-7.88 (m, 2H); 7.60 (d, J=8.24, 1H); 7.48 (t, J=7.21, 1H); 7.3-7.4 (m, 2H).

FAB-MS: M/e=292, 294 (M+).

EXAMPLE 36

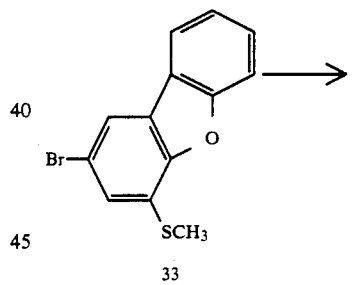

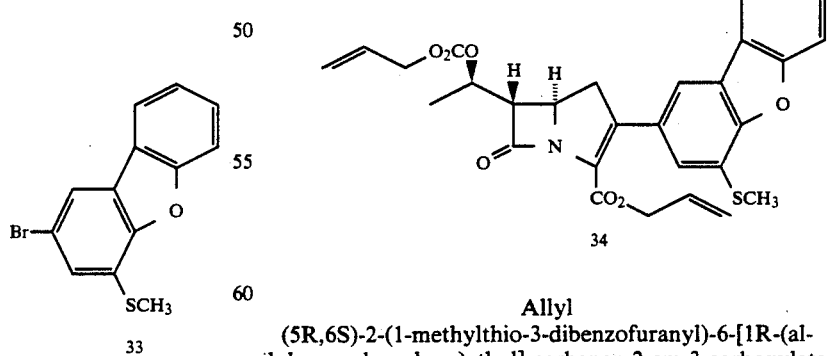

Allyl (5R,6S)-2-(1-methylthio-3-dibenzofuranyl)-6-[1R-(allyloxycarbonyloxy)ethyl]-carbapen-2-em-3-carboxylate (34)

In a manner analogous to that described in Examples 14 and 16, but starting with 1-methylthio-3-bromodibenzofuran 33, the title compound was obtained as a yellow foam.

IR (CHCl$_3$): 1780 ($\beta$-lactam); 1740 (carbonate); 1720 cm$^{-1}$ (ester).

UV (acetonitrile): $\lambda_{max}$=285 ($\epsilon$=20,600).

$^1$H-NMR (300 MHz, CDCl$_3$): $\delta$1.49 (d, J=6.41 Hz, 3H, —CH$_3$); 2.61 (s, 3H, —SCH$_3$); 3.31-3.35 (m, 2H, H1); 3.43 (dd, J=2.6, 8.37, 1H, H6); 4.31 (dt, J=2.4, 9.40, 1H, H5); 4.58-4.74 (m, 4H, C=C—CH$_2$—); 5.13-5.38 (m, 5H, H8, CH$_2$=C—); 5.78-5.94 (m, 2H, C=CH—); 7.32-7.38 (m, 2H); 7.47 (t, J=7.8, 1H); 7.62 (d, J=8.1, 1H); 7.76 (s, 1H); 7.88 (d, J=7.7, 1H).

EXAMPLE 37

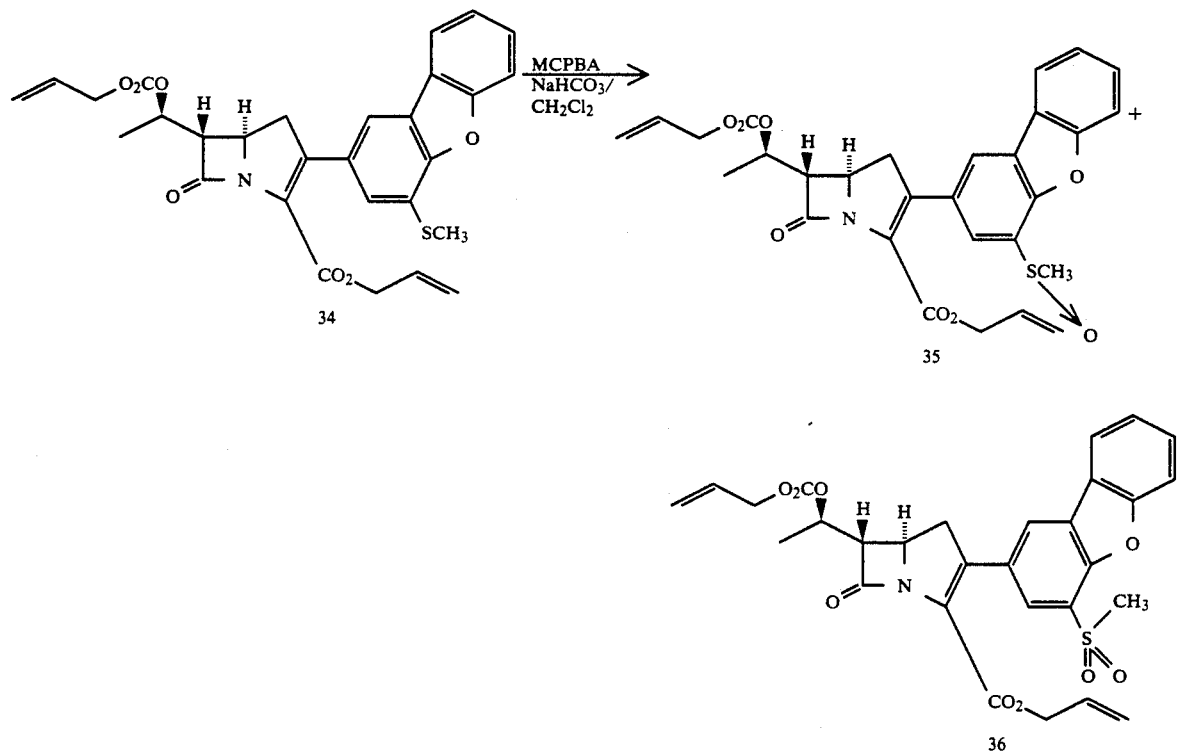

Allyl (5R,6S)-2-(1-methylsulfinyl-3-dibenzofuranyl)-6-[1R-(allyloxycarbonyloxy)ethyl]-carbapen-2-em-3-carboxylate (35) and allyl (5R,6S)-2-(1-methylsulfonyl-3-dibenzofuranyl)-6-[1R-(allyloxycarbonyloxy)ethyl]-carbapen-2-em-3-carboxylate (36)

To a solution of the carbapenem 34 (91.4 mg, 0.171 mmol) dissolved in methylene chloride (1.6 ml) at 0° C. was added aqueous sodium bicarbonate (0.5M, 0.8 ml) and m-chloroperbenzoic acid (44.1 mg, 0.256 mmol). After stirring vigorously for 10 minutes the reaction mixture was quenched with 5% aqueous Na$_2$S$_2$O$_3$, diluted into ethyl acetate and washed successively with saturated NaHCO$_3$, H$_2$O, and brine. Drying over MgSO$_4$ and evaporation gave 96 mg of a yellow oil which was purified by flash chromatography through 10 g of silica gel (7:3 ethyl acetate:hexane) yielding 15.7 mg (16%) of the sulfoxide as a yellow oil and 63.9 mg (68%) of the sulfone as a yellow oil.

Sulfoxide 35

IR (CHCl$_3$): 1780 ($\beta$-lactam); 1740 (carbonate); 1720 cm$^{-1}$ (ester).

UV (acetonitrile): $\lambda_{max}$=292 nm ($\epsilon$=22,600).

$^1$H-NMR (300 MHz, CDCl$_3$): $\delta$1.49 (d, J=6.12 Hz, 3H, CH$_3$); 3.33-3.49 (m, 6H, H6, H1, —SCH$_3$); 4.34 (dt, J=2.45, 9.70, 1H, H5); 4.59-4.71 (m, 4H, C=C—CH$_2$—); 5.15-5.39 (m, 4H, CH$_2$=C—); 5.8-6.1 (m, 2H, C=CH—); 7.43 (t, J=7.4, 1H); 7.56 (t, J=7.1, 1H); 7.69 (d, J=8.2, 1H); 7.94-7.97 (m, 2H); 8.28 (d, J=1.7, 1H).

Sulfone 36

IR (CHCl$_3$): 1780 ($\beta$-lactam); 1740 (carbonate); 1720 cm$^{-1}$ (ester).

UV (acetonitrile): $\lambda_{max}$=291 nm ($\epsilon$=17,500).

$^1$H-NMR (300 MHz, CDCl$_3$): $\delta$1.49 (d, J=6.42, 3H, —CH$_3$); 3.00 (s, 3H, —SCH$_3$); 3.34-3.41 (m, 2H, H1a,b); 3.44 (dd, J=2.6, 8.18, 1H, H6); 4.32 (dt, J=2.2, 7.08, 1H, H5); 4.55-4.75 (m, 4H, C=C—CH$_2$—); 5.13-5.39 (m, 5H, H8, CH$_2$=C—); 5.79-5.94 (m, 2H, C=CH—); 7.40 (t, J=7.7, 1H); 7.51 (t, J=7.1, 1H); 7.59 (d, J=8.1, 1H); 7.84 (dd, J=2.5, 1.7, 1H); 7.94 (d, J=7.7, 1H); 8.14 (s, 1H).

EXAMPLE 38

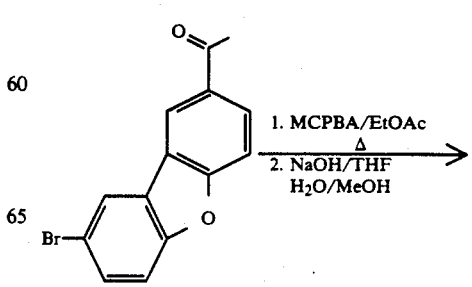

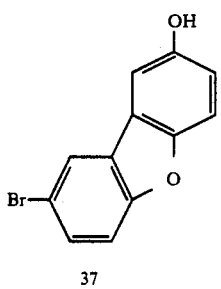

37

3-Bromo-6-hydroxydibenzofuran (37)

A solution of 3-bromo-6-acetyl-dibenzofuran (1.0 g, 3.4 mmol; H. Gilman, et. al., J. Amer. Chem. Soc., 61, 2836, 1939) was dissolved in 35 ml ethyl acetate and m-chloroperbenzoic acid (718.5 mg, 4.1 mmol) was added. The mixture was refluxed for 48 hours, then quenched with 5% $Na_2S_2O_3$. The mixture was poured into 100 ml of ethyl acetate and was then washed successively with $NaHCO_3$ (sat.), $H_2O$, NaCl (sat.) Drying $MgSO_4$ and evaporation gave 1.06 g of a yellow solid.

This solid was dissolved in 2:1 THF:methane at room temperature and 2N NaOH was added. The solution stirred for 5 minutes and then most of the THF was evaporated off. The residue was extracted thoroughly with ethyl acetate and the organic layers were combined, washed successively with 2N HCl, $H_2O$, and brine. Drying and evaporation gave 950 mg of a yellow solid which was purified by flash chromatography through 100 g of silica gel (10% ethyl acetate-hexanes) to yield 309 mg (34%) of the title compound.

$^1$H-NMR (300 MHz, $CDCl_3$) 6.96 (dd, J=8.82, 2.59, 1H); 7.28 (d, J=2.62, 1H); 7.37–7.42 (m, 2H); 7.49 (dd, J=1.96, J=8.8, 1H); 7.98 (d, J=2.02, 1H).

EXAMPLE 39

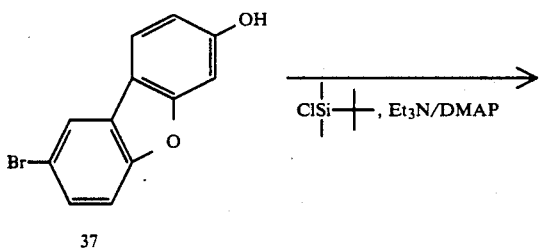

3-Bromo-6-(t-butyldimethylsilyloxy)-dibenzofuran (38)

To a solution of 3-bromo-6-hydroxydibenzofuran (309 mg, 1.17 mmol) in 8 ml THF at room temperature were added triethylamine (0.23 ml, 1.6 mmol), 4-dimethylaminopyridine (14 mg, 0.12 mmol) and t-butyldimethylsilyl chloride (229 mg, 1.5 mmol). The mixture was stirred at room temperature overnight and then diluted into ethyl acetate and washed successively with $NH_4Cl$ (sat.), $H_2O$, and brine. Drying ($MgSO_4$) and evaporation gave 421 mg of brown solid which was purified by flash chromatography through 40 g silica gel (10% EtOAc/hexane) to yield 388 mg (87%) of the title compound.

$^1$H-NMR (300 MHz, $CDCl_3$): δ0.21 (s, 6H); 1.00 (s, 9H); 6.96 (dd, J=8.82, 2.66, 1H); 7.29 (d, J=2.38, 1H); 7.37 (s, 1H); 7.40 (s, 1H); 7.5 (dd, J=8.80, 2.2, 1H); 7.9 (d, J=1.89, 1H).

EXAMPLE 40

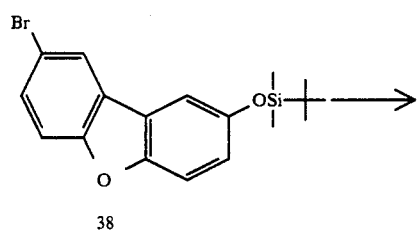

38

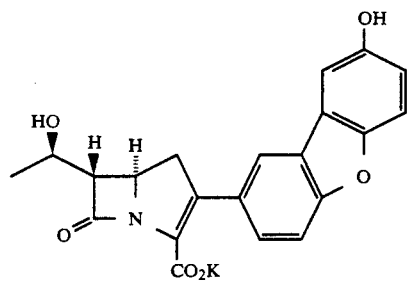

39

Potassium (5R,6S)-2-(3-hydroxy-6-dibenzofuranyl)-6-(1-R-hydroxyethyl)-carbapen-2-em-3-carboxylate (39)

In a manner analogous to that described in Examples 14–16 and 19, but starting with 3-bromo-6-(t-butyldimethylsilyoxy)-dibenzofuran 38 the title compound was obtained as a lyophilized solid.

UV ($H_2O$): λmax=304 nm (ε=19,500).

IR (KBr): 1740 (β-lactam), 1690 cm$^{-1}$ (carboxylate).

$^1$H-NMR (300 MHz, 2:1 $D_2O$:$CD_3CN$): δ1.68 (d, J=4.70, 3H, —$CH_3$); 3.52 (dd, J=17.09, 9.28, 1H, H1a); 3.81–3.91 (m, 2H, H6, H1b); 4.58–4.70 (m, 2H, H5, H8); 7.38–7.42 (m, 1H), 7.85–7.91 (m, 4H), 8.37 (s, 1H).

EXAMPLE 41

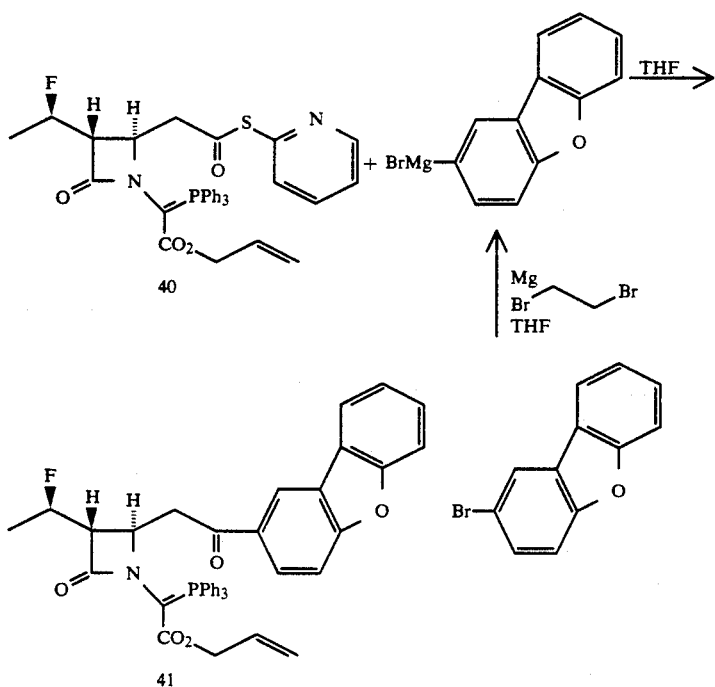

(3R,4R)-1-(allyloxycarbonyltriphenylphos- phoranylidene)methyl-3-(1R-fluoroethyl)-4-(3-diben- zofuranylcarbonyl)methyl-azetidin-2-one (41)

To a solution of 3-bromodibenzofuran (250 mg, 1.01 mmol) in 2.5 ml of THF were added magnesium (36 mg, 1.5 mmol) and dibromoethane (0.01 ml). The mixture was sonicated briefly and was then stirred at room temperature for 1 hour. The 0.4M Grignard solution thus prepared was used as described below.

To a solution of (3R,4R)-1-(allyloxycarbonyltri- phenylphosphoranylidene)methyl-3-(1R-fluoroethyl)-4- [(2-pyridylthio)carbonyl]methyl-azetidin-2-one 40 (150 mg, 0.23 mmol) in THF (0.7 ml) at $-40°$ C. was added (0.059 ml, 0.236 mmol) of the above 0.4M Grignard solution. The temperature was allowed to rise to $-20°$ C. over 20 minutes at which time the reaction was complete. The solution was diluted into 25 ml ethyl acetate and washed successively with saturated $NH_4Cl$, 1N NaOH, $H_2O$, and brine. Drying ($MgSO_4$) and evaporation gave a yellow foam which was purified by flash chromatography through 15 g of silica gel (7:3 ethyl acetate:hexane) to yield 115 mg (71%) of the title compound as a yellow foam.

IR ($CHCl_3$): 1749 ($\beta$-lactam), 1680 (ketone), 1615 cm$^{-1}$ (ylide).

$^1$H-NMR (300 MHz, $CDCl_3$): $\delta 1.22$ (dd, J=18.7, 6.59, 3H, $CH_3$)

EXAMPLE 42

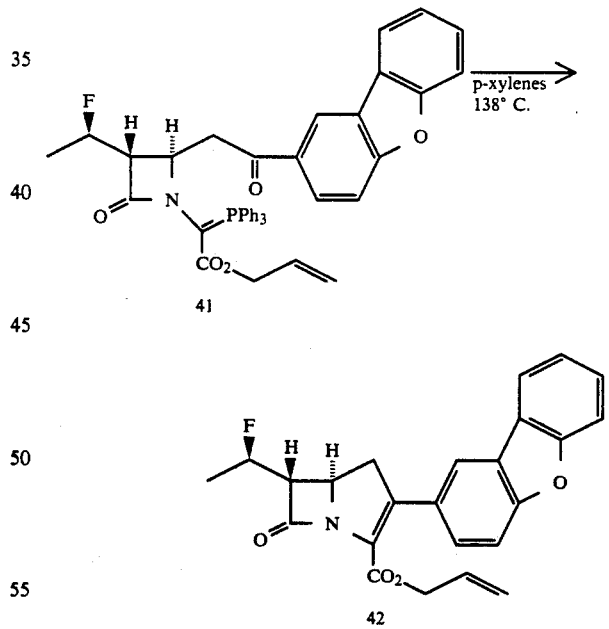

Allyl-(5R,6R)-2-(3-dibenzofuranyl)-6-(1R-fluoroethyl)- carbapen-2-em-3-carboxylate (42)

A solution of the phosphorane 41 (112 mg, 0.16 mmol) and several crystals of hydroquinone in 9 ml of p-xylene was refluxed (138° C.) for 1.5 hours. The reaction was evaporated giving a yellow oil which was purified by flash chromatography through 10 g of silica gel (3:7 ethyl acetate:hexanes) yielding 44 mg (67%) of the title compound as a yellow foam.

FAB-MS: 405 (M+1).

$^1$H-NMR (300 MHz, CDCl$_3$): δ1.51 (dd, J=17.67, 6.38, 3H, —CH$_3$); 3,3-3.4 (m, 2H, H1a,b); 3.42 (dd, J=8.03, 2.65, 1H, H6); 4.34 (dt, J=2.68, 9.46, 1H, H5); 4.58-4.71 (m, 2H, O—CH$_2$—C≡C); 4.9-5.3 (m, 3H, H8, CH$_2$=C—); 5.7-5.8 (m, 1H, C=CH—); 7.34 (t, J=7.93, 1H); 7.4-7.6 (m, 3H); 7.91 (d, J=7.14, 1H); 7.97 (s, 1H).

EXAMPLE 43

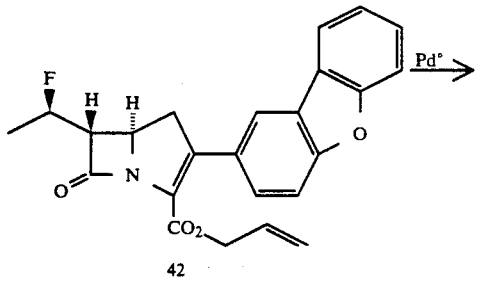

42

43

Potassium (5R,6R)-2-(3-dibenzofuranyl-6-(1R-fluoroethyl)-carbapen-2-em-3-carboxylate (43)

To a solution of the carbapenem 42 (44 mg, 0.108 mmol) in 0.9 ml of ethyl acetate at 0° C. was added potassium 2-ethylhexanoate (0.5M in ethyl acetate 0.217 ml, 0.108 mmol) followed by a solution of tetrakis(triphenylphosphine)palladium (13 mg, 0.011 mmol) and triphenylphosphine (8.4 mg, 0.32 mmol) in 0.5 ml dichloromethane. The reaction mixture was stirred for 30 minutes during which time a yellow precipitate formed and was then added dropwise to 4 ml of ethyl ether. The precipitate was collected by centrifugation, washed with ethyl ether, and dried under vacuum to give 31 mg of a yellow solid. Purification by reverse phase prep tlc (2:1 H$_2$O:CH$_3$CN) yielded 4.7 mg (10%) of the title compoune as a lyophilized solid.

UV (H$_2$O): λmax=288 (ε=23,000).

IR (KBr): 1750 (β-lactam), 1600 cm$^{-1}$ (carboxylate).

$^1$H-NMR (300 MHz, 2:1 D$_2$O:CD$_3$CN) δ1.83 (dd, J=6.13, 24.75, 3H, CH$_3$); 3.51 (dd, J=9.80, 16.75, 1H, H1a); 3.89 (dd, J=8.76, 16.61, 1H, H1b); 4.00-4.09 (m, 1H, H6); 4.70-4.76 (m, 1H, H5); 5.41-5.61 (m, J=38.3, 1H, H8); 7.77-8.44 (m, ArH, 7H).

TABLES I AND II

Employing the procedures described herein, additional compounds of the present invention were prepared. These are described in Tables I and II below, which additionally include characterizing data.

TABLE I

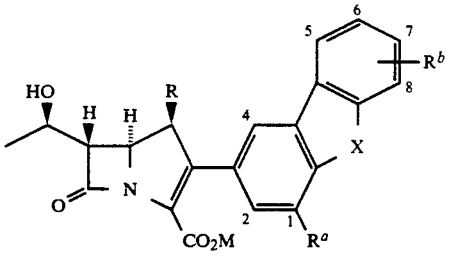

| EXP. NO. | M | R | X | R$^a$ | R$^b$ | λ$_{max}^{H_2O}$ (nm) |
|---|---|---|---|---|---|---|
| 44 | K | H | O | SCH$_3$ | H | 290 |
| 45 | K | H | O | S(O)CH$_3$ | H | 292 |
| 46 | K | H | O | SO$_2$CH$_3$ | H | 296 |
| 47 | K | H | O | SC$_2$H$_5$ | H | 293 |
| 48 | K | H | O | SCH$_2$CH$_2$OH | H | 293 |
| 49 | K | H | O | S(O)CH$_2$CH$_2$OH | H | 292 |
| 50 | K | H | O | SO$_2$CH$_2$CH$_2$OH | H | 295 |
| 51 | K | H | O | CH$_2$OH | H | 291 |
| 52 | K | H | O | CHO | H | 295 |
| 53 | K | H | O | CH=NOH | H | 296 |
| 54 | K | H | O | CN | H | 292 |
| 55 | K | H | O | CO$_2$K | H | 297 |
| 56 | K | H | O | CO$_2$CH$_3$ | H | 298 |
| 57 | K | H | O | H | 8-CH$_2$OH | 290 |
| 58 | K | H | O | H | 7-CHO | 321 |
| 59 | K | H | O | H | 7-CH=NOH | 312 |
| 60 | K | H | O | H | 7-CN | 303 |
| 61 | K | H | O | H | 6-CH$_2$OH | 292 |
| 62 | K | H | S | H | 7-CN | 304 |
| 63 | K | H | S | H | 7-CH$_2$OH | 300 |
| 64 | K | H | SO | H | 7-CH$_2$OH | 296 |
| 65 | K | H | SO$_2$ | H | 7-CH$_2$OH | 328 |
| 66 | K | H | S | H | 7-CHO | 312 |
| 67 | K | H | SO | H | 7-CHO | 313 |
| 68 | K | H | S | H | 7-CH$_2$N$_3$ | 300 |
| 69 | K | H | S | CH$_2$OH | H | 312 |
| 70 | K | H | SO | CH$_2$OH | H | 332 |
| 71 | K | H | SO$_2$ | CH$_2$OH | H | 331 |
| 72 | K | H | S | CHO | H | 305 |
| 73 | K | H | SO | CHO | H | 336 |
| 74 | K | H | S | CH(=NOH) | H | 303 |
| 75 | K | H | S | CN | H | 306 |
| 76 | K | H | S | Cl | H | 314 |
| 77 | K | H | SO | Cl | H | 338 |
| 94 | K | H | O | CONHCH$_3$ | H | 296 |
| 95 | K | H | O | CON(CH$_3$)$_2$ | H | 291 |
| 98 | K | H | O | CONHCH$_2$CN | H | 295, 248 |
| 105 | K | H | O | H | 6-CHO | 302 |
| 106 | K | H | O | H | 8-CHO | 307 |
| 113 | K | H | O | H | 7-CONH$_2$ | 302 |
| 161 | K | H | S | CONH$_2$ | H | 304, 237 |
| 164 | K | H | S | H | 7-CONH$_2$ | 326, 290 |
| 209 | K | H | SO | CN | H | 341, 250 |
| 212 | K | H | SO | H | 7-CN | 303, 255 |
| 214 | K | H | SO | CONH$_2$ | H | 334, 299, 249 |
| 259 | K | H | SO$_2$ | CHO | H | 339 |
| 267 | K | H | SO$_2$ | H | 7-CN | 300, 251 |

TABLE II

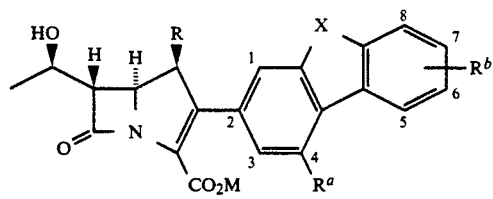

| EXP. NO. | M | R | X | $R^a$ | $R^b$ | $\lambda_{max}^{H_2O}$ (nm) |
|---|---|---|---|---|---|---|
| 78 | K | H | O | H | 6-CH$_2$OH | 328 |

TABLE II

Employing the procedures described herein, additional compounds of the present invention may be prepared, as set forth in Table III.

TABLE III

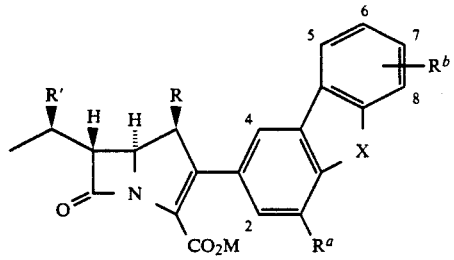

| EXP. NO. | M | R' | R | X | $R^a$ | $R^b$ |
|---|---|---|---|---|---|---|
| 79 | K | OH | H | O | F | H |
| 80 | K | OH | H | O | OH | H |
| 81 | K | OH | H | O | SCF$_3$ | H |
| 82 | K | OH | H | O | CF$_3$ | H |
| 83 | K | OH | H | O | NHCOCH$_3$ | H |
| 84 | K | OH | H | O | NHSO$_2$CH$_3$ | H |
| 85 | K | OH | H | O | SO$_3$K | H |
| 86 | K | OH | H | O | SO$_2$NH$_2$ | H |
| 87 | K | OH | H | O | SO$_2$NHCN | H |
| 88 | K | OH | H | O | SO$_2$NHCONH$_2$ | H |
| 89 | K | OH | H | O | PO$_3$KH | H |
| 90 | K | OH | H | O | COCH$_3$ | H |
| 91 | K | OH | H | O | CH=NOCH$_2$CO$_2$H | H |
| 92 | K | OH | H | O | CH=NOC(CH$_3$)$_2$CO$_2$H | H |
| 93 | K | OH | H | O | CO$_2$CH$_2$CH$_2$OH | H |
| 96 | K | OH | H | O | CONHOH | H |
| 97 | K | OH | H | O | CONHCH$_2$CONH$_2$ | H |
| 99 | K | OH | H | O | (1H-tetrazol-5-yl) | H |
| 100 | K | OH | H | O | (1-CH$_3$-tetrazol-5-yl) | H |

TABLE III-continued

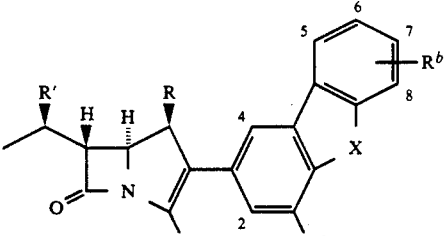

| EXP. NO. | M | R' | R | X | $R^a$ | $R^b$ |
|---|---|---|---|---|---|---|
| 101 | K | OH | H | O | (2-CH$_3$-tetrazol-5-yl) | H |
| 102 | K | OH | H | O | (1-CH$_2$CH$_2$OH-tetrazol-5-yl) | H |
| 103 | K | OH | H | O | (2-CH$_2$CH$_2$OH-tetrazol-5-yl) | H |
| 104 | K | OH | H | O | H | 5-CHO |
| 107 | K | OH | H | O | H | 5-CN |
| 108 | K | OH | H | O | H | 6-CN |
| 109 | K | OH | H | O | H | 8-CN |
| 110 | K | F | CH$_3$ | O | CONH$_2$ | H |
| 111 | K | OH | H | O | H | 5-CONH$_2$ |
| 112 | K | OH | H | O | H | 6-CONH$_2$ |
| 114 | K | OH | H | O | H | 8-CONH$_2$ |
| 115 | K | OH | H | O | F | 7-CH$_2$OH |
| 116 | K | OH | H | O | F | 7-CHO |
| 117 | K | OH | H | O | F | 7-CONH$_2$ |
| 118 | K | OH | H | O | F | 7-CN |
| 119 | K | OH | H | O | F | 7-CO$_2$K |
| 120 | K | OH | H | O | SOCH$_3$ | 7-CHO |
| 121 | K | OH | H | O | CN | 7-SOCH$_3$ |
| 122 | K | OH | H | O | CHO | 7-SOCH$_3$ |
| 123 | K | OH | H | O | CONH$_2$ | 7-SOCH$_3$ |
| 124 | K | F | H | O | CONH$_2$ | H |
| 125 | K | F | H | O | CN | H |
| 126 | K | F | H | O | CHO | H |
| 127 | K | OH | CH$_3$ | O | CONH$_2$ | H |
| 128 | K | OH | CH$_3$ | O | CN | H |
| 129 | K | OH | CH$_3$ | O | CHO | H |
| 130 | K | OH | H | S | F | H |
| 131 | K | OH | H | S | OH | H |
| 132 | K | OH | H | S | SCF$_3$ | H |
| 133 | K | OH | H | S | CF$_3$ | H |
| 134 | K | OH | H | S | NHCOCH$_3$ | H |
| 135 | K | OH | H | S | NHSO$_2$CH$_3$ | H |
| 136 | K | OH | H | S | SO$_3$K | H |
| 137 | K | OH | H | S | SO$_2$NH$_2$ | H |
| 138 | K | OH | H | S | SO$_2$NHCN | H |
| 139 | K | OH | H | S | SO$_2$NHCONH$_2$ | H |
| 140 | K | OH | H | S | PO$_3$KH | H |
| 141 | K | OH | H | S | COCH$_3$ | H |
| 142 | K | OH | H | S | CH=NOCH$_2$CO$_2$H | H |
| 143 | K | OH | H | S | CH=NOC(CH$_3$)$_2$CO$_2$H | H |
| 144 | K | OH | H | S | CO$_2$CH$_2$CH$_2$OH | H |
| 145 | K | OH | H | S | CONHCH$_3$ | H |

TABLE III-continued

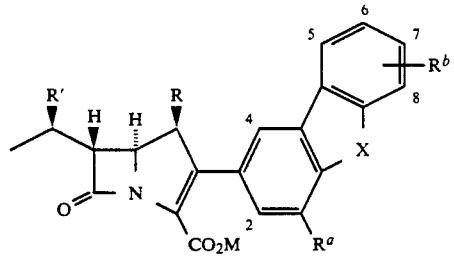
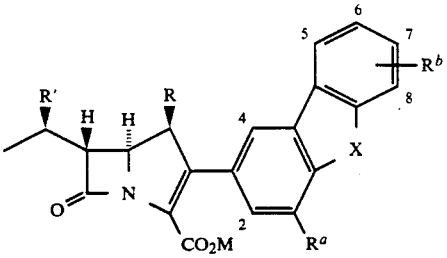

| EXP. NO. | M | R' | R | X | Rᵃ | Rᵇ |
|---|---|---|---|---|---|---|
| 146 | K | OH | H | S | CON(CH₃)₂ | H |
| 147 | K | OH | H | S | CONHOH | H |
| 148 | K | OH | H | S | CONHCH₂CONH₂ | H |
| 149 | K | OH | H | S | CONHCH₂CN | H |
| 150 | K | OH | H | S | (tetrazole, HN) | H |
| 151 | K | OH | H | S | (tetrazole, N-CH₃) | H |
| 152 | K | OH | H | S | (triazole, N-CH₃) | H |
| 153 | K | OH | H | S | (tetrazole, N-CH₂CH₂OH) | H |
| 154 | K | OH | H | S | (triazole, N-CH₂CH₂OH) | H |
| 155 | K | OH | H | S | H | 5-CHO |
| 156 | K | OH | H | S | H | 6-CHO |
| 157 | K | OH | H | S | H | 8-CHO |
| 158 | K | OH | H | S | H | 5-CN |
| 159 | K | OH | H | S | H | 6-CN |
| 160 | K | OH | H | S | H | 8-CN |
| 162 | K | OH | H | S | H | 5-CONH₂ |
| 163 | K | OH | H | S | H | 6-CONH₂ |
| 165 | K | OH | H | S | H | 8-CONH₂ |
| 166 | K | OH | H | S | F | 7-CH₂OH |
| 167 | K | OH | H | S | F | 7-CHO |
| 168 | K | OH | H | S | F | 7-CONH₂ |
| 169 | K | OH | H | S | F | 7-CN |
| 170 | K | OH | H | S | F | 7-CO₂K |
| 171 | K | OH | H | S | SOCH₃ | 7-CHO |
| 172 | K | OH | H | S | CN | 7-SOCH₃ |
| 173 | K | OH | H | S | CHO | 7-SOCH₃ |
| 174 | K | OH | H | S | CONH₂ | 7-SOCH₃ |
| 175 | K | F | H | S | CONH₂ | H |
| 176 | K | F | H | S | CN | H |
| 177 | K | F | H | S | CHO | H |
| 178 | K | OH | CH₃ | S | CONH₂ | H |
| 179 | K | OH | CH₃ | S | CN | H |
| 180 | K | OH | CH₃ | S | CHO | H |
| 181 | K | OH | H | SO | F | H |
| 182 | K | OH | H | SO | OH | H |
| 183 | K | OH | H | SO | SCF₃ | H |
| 184 | K | OH | H | SO | CF₃ | H |
| 185 | K | OH | H | SO | NHCOCH₃ | H |
| 186 | K | OH | H | SO | NHSO₂CH₃ | H |
| 187 | K | OH | H | SO | SO₃K | H |
| 188 | K | OH | H | SO | SO₂NH₂ | H |
| 189 | K | OH | H | SO | SO₂NHCN | H |
| 190 | K | OH | H | SO | SO₂NHCONH₂ | H |
| 191 | K | OH | H | SO | PO₃KH | H |
| 192 | K | OH | H | SO | COCH₃ | H |
| 193 | K | OH | H | SO | CH=NOCH₂CO₂H | H |
| 194 | K | OH | H | SO | CH=NOC(CH₃)₂CO₂H | H |
| 195 | K | OH | H | SO | CO₂CH₂CH₂OH | H |
| 196 | K | OH | H | SO | CONHCH₃ | H |
| 197 | K | OH | H | SO | CON(CH₃)₂ | H |
| 198 | K | OH | H | SO | CONHOH | H |
| 199 | K | OH | H | SO | CONHCH₂CONH₂ | H |
| 200 | K | OH | H | SO | CONHCH₂CN | H |
| 201 | K | OH | H | SO | (tetrazole, HN) | H |
| 202 | K | OH | H | SO | (tetrazole, N-CH₃) | H |
| 203 | K | OH | H | SO | (triazole, N-CH₃) | H |
| 204 | K | OH | H | SO | (tetrazole, N-CH₂CH₂OH) | H |
| 205 | K | OH | H | SO | (triazole, N-CH₂CH₂OH) | H |
| 206 | K | OH | H | SO | H | 5-CHO |
| 207 | K | OH | H | SO | H | 6-CHO |
| 208 | K | OH | H | SO | H | 8-CHO |
| 210 | K | OH | H | SO | H | 5-CN |
| 211 | K | OH | H | SO | H | 6-CN |

TABLE III-continued

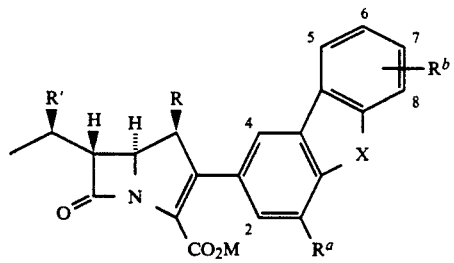

| EXP. NO. | M | R' | R | X | R$^a$ | R$^b$ |
|---|---|---|---|---|---|---|
| 213 | K | OH | H | SO | H | 8-CN |
| 215 | K | OH | H | SO | H | 5-CONH$_2$ |
| 216 | K | OH | H | SO | H | 6-CONH$_2$ |
| 217 | K | OH | H | SO | H | 7-CONH$_2$ |
| 218 | K | OH | H | SO | H | 8-CONH$_2$ |
| 219 | K | OH | H | SO | F | 7-CH$_2$OH |
| 220 | K | OH | H | SO | F | 7-CHO |
| 221 | K | OH | H | SO | F | 7-CONH$_2$ |
| 222 | K | OH | H | SO | F | 7-CN |
| 223 | K | OH | H | SO | F | 7-CO$_2$K |
| 224 | K | OH | H | SO | SOCH$_3$ | 7-CHO |
| 225 | K | OH | H | SO | CN | 7-SOCH$_3$ |
| 226 | K | OH | H | SO | CHO | 7-SOCH$_3$ |
| 227 | K | OH | H | SO | CONH$_2$ | 7-SOCH$_3$ |
| 228 | K | F | H | SO | CONH$_2$ | H |
| 229 | K | F | H | SO | CN | H |
| 230 | K | F | H | SO | CHO | H |
| 231 | K | OH | CH$_3$ | SO | CONH$_2$ | H |
| 232 | K | OH | CH$_3$ | SO | CN | H |
| 233 | K | OH | CH$_3$ | SO | CHO | H |
| 234 | K | OH | H | SO$_2$ | F | H |
| 235 | K | OH | H | SO$_2$ | OH | H |
| 236 | K | OH | H | SO$_2$ | SF$_3$ | H |
| 237 | K | OH | H | SO$_2$ | CF$_3$ | H |
| 238 | K | OH | H | SO$_2$ | NHCOCH$_3$ | H |
| 239 | K | OH | H | SO$_2$ | NHSO$_2$CH$_3$ | H |
| 240 | K | OH | H | SO$_2$ | SO$_3$K | H |
| 241 | K | OH | H | SO$_2$ | SO$_2$NH$_2$ | H |
| 242 | K | OH | H | SO$_2$ | SO$_2$NHCN | H |
| 243 | K | OH | H | SO$_2$ | SO$_2$NHCONH$_2$ | H |
| 244 | K | OH | H | SO$_2$ | PO$_3$KH | H |
| 245 | K | OH | H | SO$_2$ | COCH$_3$ | H |
| 246 | K | OH | H | SO$_2$ | CH=NOCH$_2$CO$_2$H | H |
| 247 | K | OH | H | SO$_2$ | CH=NOC(CH$_3$)$_2$CO$_2$H | H |
| 248 | K | OH | H | SO$_2$ | CO$_2$CH$_2$CH$_2$OH | H |
| 249 | K | OH | H | SO$_2$ | CONHCH$_3$ | H |
| 250 | K | OH | H | SO$_2$ | CON(CH$_3$)$_2$ | H |
| 251 | K | OH | H | SO$_2$ | CONHOH | H |
| 252 | K | OH | H | SO$_2$ | CONHCH$_2$CONH$_2$ | H |
| 253 | K | OH | H | SO$_2$ | CONHCH$_2$CN | H |
| 254 | K | OH | H | SO$_2$ | 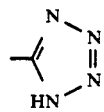 (tetrazole, HN) | H |
| 255 | K | OH | H | SO$_2$ | 1-methyl-tetrazol-5-yl | H |
| 256 | K | OH | H | SO$_2$ | 2-methyl-tetrazol-5-yl | H |
| 257 | K | OH | H | SO$_2$ | 1-(2-hydroxyethyl)-tetrazol-5-yl | H |
| 258 | K | OH | H | SO$_2$ | 2-(2-hydroxyethyl)-tetrazol-5-yl | H |
| 260 | K | OH | H | SO$_2$ | H | 5-CHO |
| 261 | K | OH | H | SO$_2$ | H | 6-CHO |
| 262 | K | OH | H | SO$_2$ | H | 7-CHO |
| 263 | K | OH | H | SO$_2$ | H | 8-CHO |
| 264 | K | OH | H | SO$_2$ | CN | H |
| 265 | K | OH | H | SO$_2$ | H | 5-CN |
| 266 | K | OH | H | SO$_2$ | H | 6-CN |
| 268 | K | OH | H | SO$_2$ | H | 8-CN |
| 269 | K | OH | H | SO$_2$ | CONH$_2$ | H |
| 270 | K | OH | H | SO$_2$ | H | CONH$_2$ |
| 271 | K | OH | H | SO$_2$ | H | 6-CONH$_2$ |
| 272 | K | OH | H | SO$_2$ | H | 7-CONH$_2$ |
| 273 | K | OH | H | SO$_2$ | H | 8-CONH$_2$ |
| 274 | K | OH | H | SO$_2$ | F | 7-CH$_2$OH |
| 274 | K | OH | H | SO$_2$ | F | 7-CHO |
| 276 | K | OH | H | SO$_2$ | F | 7-CONH$_2$ |
| 277 | K | OH | H | SO$_2$ | F | 7-CN |
| 278 | K | OH | H | SO$_2$ | F | 7-CO$_2$K |
| 279 | K | F | H | SO$_2$ | CONH$_2$ | H |
| 280 | K | F | H | SO$_2$ | CN | H |
| 281 | K | F | H | SO$_2$ | CHO | H |
| 282 | K | OH | CH$_3$ | SO$_2$ | CONH$_2$ | H |
| 283 | K | OH | CH$_3$ | SO$_2$ | CN | H |
| 284 | K | OH | CH$_3$ | SO$_2$ | CHO | H |

EXAMPLE 285

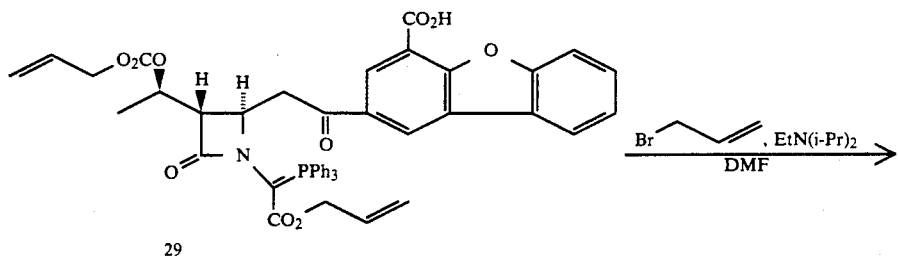

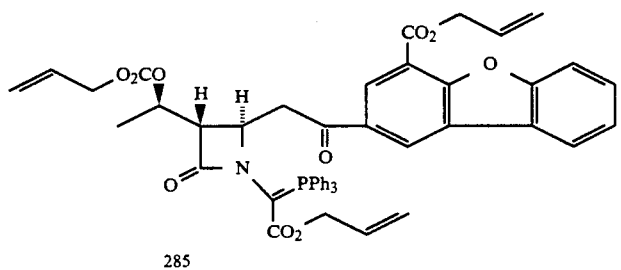

(3S,4R)-1-(allyloxycarbonyltriphenylphosphoranylidene)methyl-3-[1R-(allyloxycarbonyloxy)ethyl]-4-(1-allyloxycarbonyl-3-dibenzofuranylcarbonyl)-methylazetidin-2-one (285)

To a solution of the carboxylic acid 29 (100 mg, 0.123 mmol) in 1.5 ml of dimethylformamide were added diisopropylethylamine (0.032 ml, 0.18 mmol), and allyl bromide (0.016 ml, 0.18 mmol). After 3 hours, the reaction mixture was diluted into ethyl acetate and washed with water and brine. Drying (MgSO₄) and evaporation followed by flash chromatography of the residue through 10 g of silica gel (7:3 EtOAc/hexane) yielded 49.8 mg (47%) of the title compound.

IR (CHCl₃): 1740 (β-lactam, carbonate), 1685 (ketone), 1610 cm⁻¹ (ylide).

EXAMPLE 286

Allyl-(5R,6S)-2-(1-allyloxycarbonyl-3-dibenzofuranyl)-6-[1R-(allyloxycarbonyloxy)ethyl]-carbapen-2-em-3-carboxylate (286)

In a manner analogous to that described in Example 16, 128 mg (0.151 mmol) of the ylide 285 was cyclized to yield 62 mg (72%) of the title compound as a yellow oil.

¹H-NMR (300 MHz, CDCl₃): δ1.50 (d, J=6.3 Hz, 3H, CH₃), 3.26–3.46 (ABX, 2H, H1), 3.45 (dd, J=2.8, 8.3 Hz, 1H, H6), 4.32 (ddd, J=2.8, 9.2, 9.6 Hz, 1H, H5), 4.55–4.75 (m, 4H, O—CH₂C=C), 5.92–5.98 (m, 2H, O—CH₂C=C), 5.1–5.6 (m, 7H, H8, —C=CH₂), 5.75–6.20 (m, 3H, —CH=C), 7.38 (t, J=7.4 Hz, 1H), 7.51 (t, J=7.8 Hz, 1H), 7.68 (d, J=8.2 Hz, 1H), 7.92 (d, J=7.7 Hz, 1H), 8.09 (d, J=2.0 Hz, 1H), 8.19 (d, J=1.8 Hz, 1H).

IR (CHCl₃): 1780 (β-lactam), 1740 (carbonate), 1720 cm⁻¹ (esters).

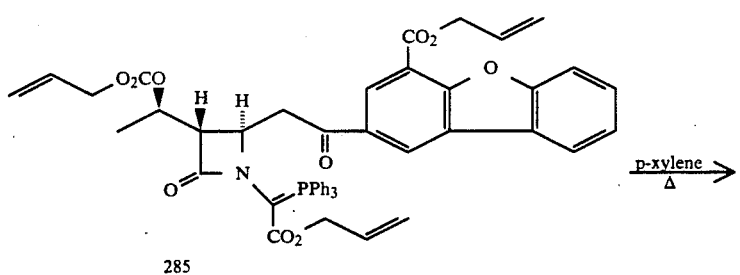

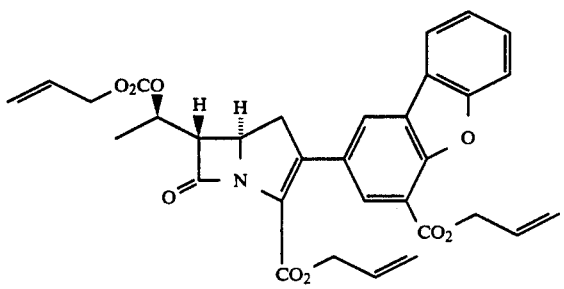

UV (CH$_3$CN): λmax=297 nm (ε=17,000).

EXAMPLE 287

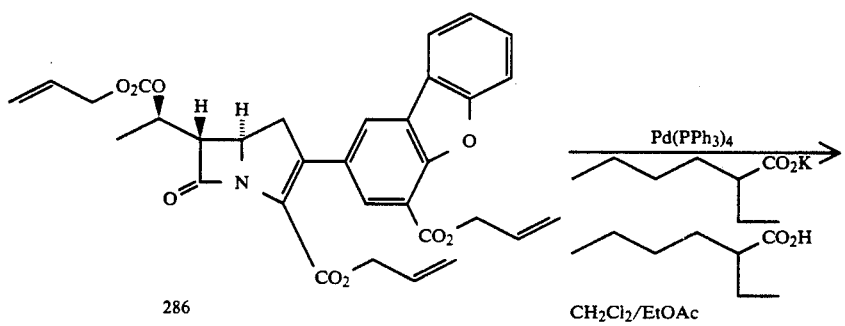

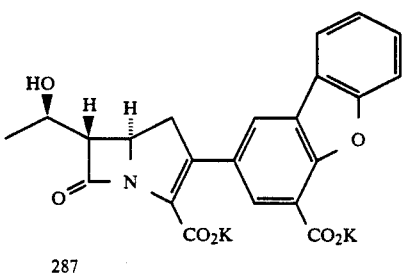

Potassium (5R,6S)-2-[1-(potassium-alkoxycarbonyl)-3-dibenzofuranyl]-6-(1R-hydroxyethyl)-carbapen-2-em-3-carboxylate (287)

To a solution of the carbapenem 286 (45 mg, 0.093 mmol) in 1 ml of methylene chloride and 0.25 ml of ethyl acetate at ambient temperature were added in sequence a solution of potassium 2-ethylhexanoate in ethyl acetate (0.5M, 0.37 ml), a solution of 2-ethylhexanoic acid in methylene chloride (1.0M, 0.093 ml), triphenylphosphine (7.3 mg, 0.028 mmol), and tetrakis(triphenylphosphine)palladium (10.7 mg, 0.0093 mmol). The reaction mixture was stirred at room temperature for 1 hour, during which time a precipitate formed. The reaction mixture was pipetted into a centrifuge tube containing cold ethyl ether and the solid was isolated by centrifugation, washing twice with additional ethyl ether. After drying under vacuum, the solid was purified by reverse phase preparative TLC (9:1 H$_2$O/CH$_3$CN, then 6:1 H$_2$O/CH$_3$CN) to yield 12.3 mg (27%) of the title compound as a fluffy white lyophilized solid. Compound 287 is also listed in Table I, where it is designated as Example 55.

$^1$H-NMR (300 MHz, 2:1 D$_2$O/CD$_3$CN): δ1.43 (d, J=6.5 Hz, 3H, CH$_3$), 3.29 (dd, J=9.8, 17 Hz, 1H, H1a), 3.58–3.72 (m, 2H, H1b, H6), 4.32–4.52 (m, 2H, H5, H8), 7.52 (dd, J=7.4, 7.6 Hz, 1H), 7.65 (dd, J=7.4, 8.1 Hz, 1H), 7.77 (d, J=8.1 Hz, 1H), 7.89 (s, 1H), 8.15 (d, J=7.6 Hz, 1H), 8.20 (s, 1H).

IR (KBr): 1750 (β-lactam), 1590 cm$^{-1}$ (carboxylates).
UV (H$_2$O): λmax=297 nm (ε=17,000).

EXAMPLE 288

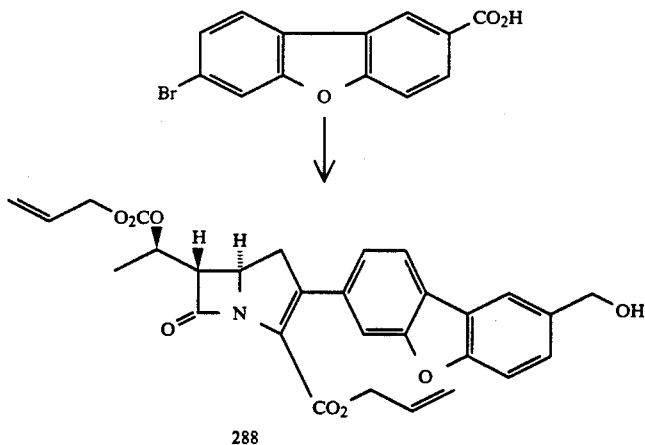

Allyl-(5R,6S)-2-(3-hydroxymethyl-7-dibenzofuranyl)-6-[1R-(allyloxycarbonyloxy)ethyl]-carbapen-2-em-3-carboxylate (288)

In an analogous manner to that described in Examples 12–16, but starting with 7-bromodibenzofuran-3-carboxylic acid, the title compound was obtained as a yellow foam.

¹H-NMR (300 MHz, CDCl₃): δ1.48 (d, J=6.4 Hz, 3H, CH₃), 3.20–3.44 (ABX, 2H, H1), 3.43 (dd, J=2.8, 8.5 Hz, 1H, H6), 4.23 (ddd, J=2.8, 9.2, 9.6, 1H, H5), 4.56–4.78 (m, 4H, —OCH₂C=C), 4.82 (s, 2H, ArCH₂O—), 5.1–5.4 (m, 5H, H8, —C=CH₂), 5.75–6.00 (m, 2H, —CH=C), 7.32 (dd, J=1.5, 8.1 Hz, 1H), 7.45 (dd, J=1.7, 8.5 Hz, 1H), 7.52 (d, J=8.5 Hz, 1H), 7.57 (s, 1H), 7.87 (d, J=8.1 Hz, 1H), 7.93 (s, 1H).

IR (CHCl₃): 1775 (β-lactam), 1740 (carbonate), 1725 cm⁻¹ (ester).

UV (CH₃CN): λmax=320 nm (ε=12,400), 303 nm (ε=13,600).

EXAMPLE 289

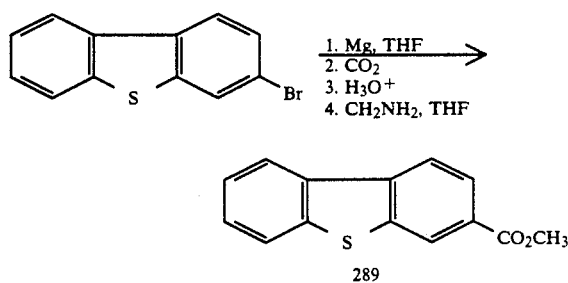

Methyl dibenzothiophene-2-carboxylate (289)

To a mixture of 2-bromodibenzothiophene (6.616 g, 25.14 mmol; H. Gilman and R. K. Ingham, J. Am. Chem. Soc. 75 3843, 1953) and magnesium turnings (0.734 g, 30.2 mmol) in 100 ml of THF was added 1,2-dibromoethane (0.10 ml) and the reaction mixture was sonicated briefly in an ultrasonic bath to initiate the Grignard formation. After stirring at room temperature for 1 hour, the yellow reaction mixture was cooled to −50° C. and carbon dioxide was bubbled through the solution for 20 minutes. During this time the yellow color faded and some precipitate deposited. The reaction mixture was allowed to warm to room temperature and became a nearly colorless solution. The reaction mixture was acidified with 1N HCl, and most of the THF was evaporated in vacuo. The residue was extracted with ethyl acetate, and the resulting organic suspension was washed with water and brine, diluted with toluene, and evaporated in vacuo to give 5.56 g of crude carboxylic acid. The crude product was suspended in 100 ml of THF and excess ethereal diazomethane was added giving a yellow solution. The excess diazomethane was consumed by addition of a small amount of acetic acid, and evaporation in vacuo gave 6.06 g of crude methyl ester. Flash chromatography through 500 g of silica gel (3:2 CH₂Cl₂/hexane) yielded 4.60 g (76%) of the title compound as a white solid, mp 127°–129° C.

¹H-NMR (300 MHz, CDCl₃): δ3.96 (s, 3H, OCH₃), 7.44–7.54 (m, 2H), 7.83–7.92 (m, 1H), 8.10 (dd, J=1.6, 8.2 Hz, 1H), 8.18 (d, J=8.1 Hz), 8.15–8.22 (m, 1H), 8.55 (d, J=1.6 Hz, 1H).

FAB-MS: m/e=243 (M+H).

EXAMPLE 290

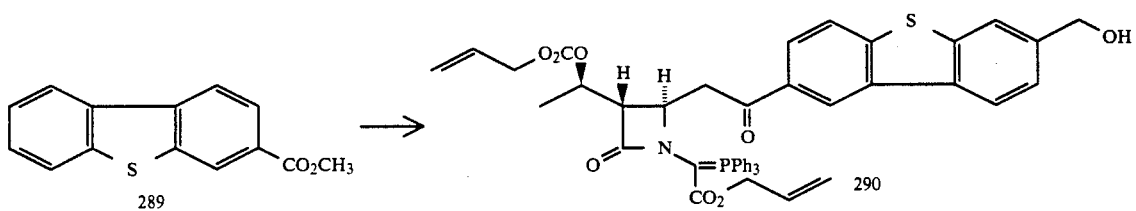

(3S,4R)-1-(allyloxycarbonyltriphenylphosphoranylidene)methyl-3-[1R-(allyloxycarbonyloxy)ethyl]-4-[2-(hydroxymethyl)-6-dibenzothienylcarbonyl]-methylazetidin-2-one (290)

In a manner analogous to that described in Examples 10–15, but starting with methyl dibenzothiophene-2-carboxylate, the title compound was obtained as a yellow foam.

IR (CHCl₃): 3450 (hydroxyl), 1745 (β-lactam), 1680 (ketone), 1610 cm⁻¹ (ylide).

EXAMPLE 291

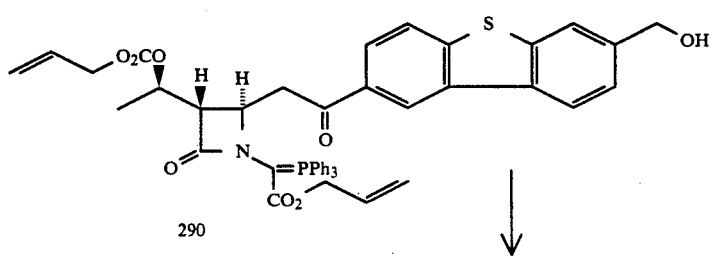

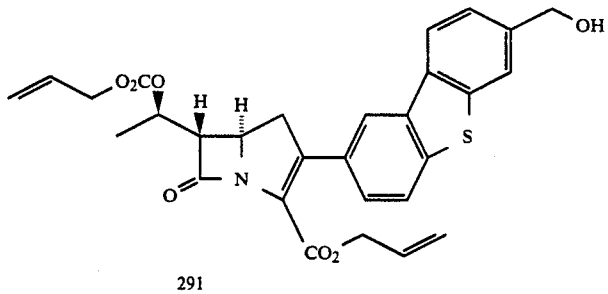

Allyl-(5R,6S)-2-(2-hydroxymethyl-6-dibenzothienyl)-6-[1R-(allyloxycarbonyloxy)ethyl]-carbapen-2-em-3-carboxylate (291)

In a manner analogous to that described in Example 16, 2.396 g (2.952 mmol) of ylide 290 was cyclized to yield 1.337 g (85%) of the title carbapenem as a yellow foam.

$^1$H-NMR (300 MHz, CDCl$_3$): δ1.45 (d, J=6.3 Hz, 3H, CH$_3$), 3.25-3.45 (m, 2H, H1), 3.44 (dd, J=2.8, 8.4 Hz, 1H, H6), 4.32 (ddd, J=2.8, 9.3, 9.5 Hz, 1H, H5), 4.55-4.80 (m, 4H, —OCH$_2$C≡C), 4.84 (s, 2H, ArCH$_2$O—), 5.1-5.4 (m, 5H, H8, —C=CH$_2$), 5.75-6.0 (m, 2H, —CH=C), 7.4 (d, J=8.3, 2H), 7.78 (d, J=8.5 Hz, 1H), 7.86 (s, 1H), 8.07 (d, J=8.1 Hz, 1H), 8.13 (s, 1H).

IR (CHCl$_3$): 1780 (β-lactam), 1745 (carbonate), 1725 cm$^{-1}$ (ester).

UV (CH$_3$CN): λmax=316 nm (ε=9,200), 292 nm (ε=12,000), 239 nm (ε=32,000).

EXAMPLE 292 mmol), the sulfoxide 292A (803.4 mg, 52%) and the sulfone 292B (119.2 mg, 7.5%) were prepared.

Sulfoxide 292A $^1$H-NMR (300 MHz, CDCl$_3$): δ1.45 (d, J=6.4 Hz, 3H, CH$_3$), 3.1-3.4 (m, 2H, H1), 3.4-3.5 (m, 1H, H6), 4.29 (br t, J=9.4 Hz, 1H, H5), 4.50-4.75 (m, 6H, —OCH$_2$C≡C, —OCH$_2$Ar), 5.1-5.4 (m, 5H, H8, —C=CH$_2$), 5.75-6.00 (m, 2H, —CH=C), 7.3-7.5 (m, 2H,) 7.59 (dd, J=2.4, 7.9 Hz, 1H), 7.71 (s, 1H), 7.75-7.90 (m, 2H).

Sulfone 292B $^1$H-NMR (300 MHz, CDCl$_3$): δ1.47 (d, J=6.2 Hz, 3H, CH$_3$), 3.21 (dd, J=10, 18.2 Hz, 1H, H1), 3.35 (dd, J=9.0, 18.2 Hz, 1H, H1), 3.47 (dd, J=2.8, 8.1 Hz, 1H, H6), 4.32 (ddd, J=2.8, 9.0, 10 Hz, 1H, H5), 4.55-4.75 (m, 4H, —OCH$_2$C≡C), 4.73 (bs, 2H, —OCH$_2$Ar), 5.1-5.4 (m, 5H, H8, —C=CH$_2$), 5.75-6.00 (m, 2H, —CH=C), 7.40 (d, J=7.9 Hz, 1H), 7.57 (d, J=8.1 Hz, 1H), 7.67 (d, J=7.9 Hz, 1H), 7.7-7.8 (m, 3H).

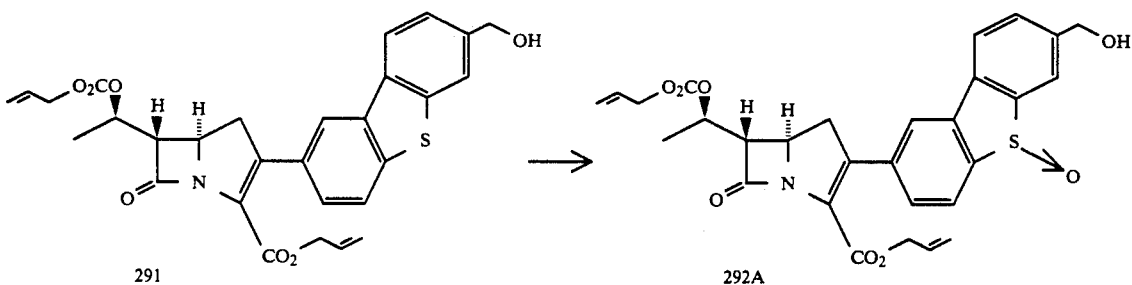

Allyl-(5R,6S)-2-(2-hydroxymethyl-9-oxo-6-dibenzothienyl)-6-[1R-(allyloxycarbonyloxy)ethyl]-carbapen-2-em-3-carboxylate (292A) and allyl-(5R,6S)-2-(2-hydroxymethyl-9,9-dioxo-6-dibenzothienyl)-6-[1R-(allyloxycarbonyloxy)ethyl]-carbapen-2-em-3-carboxylate (292B)

In a manner analogous to that described in Example 27, but starting with the carbapenem 291 (1.509 g, 2.827

EXAMPLE 293

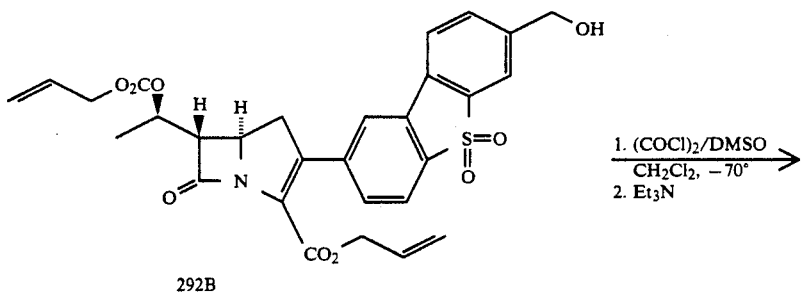

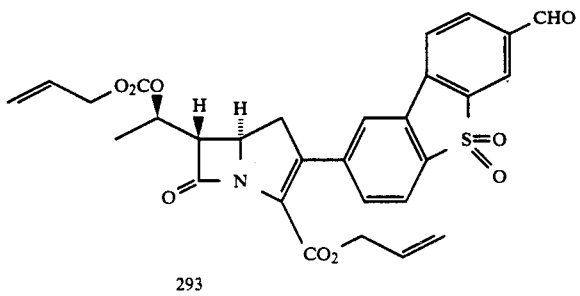

Allyl-(5R,6S)-2-(2-formyl-9,9-dioxo-6-dibenzothienyl)-6-[1R-(allyloxycarbonyloxy)ethyl]-carbepen-2-em-3-carboxylate (293)

A solution of oxalyl chloride in CH$_2$Cl$_2$ (2.0M, 0.095 ml) diluted with 1 ml of CH$_2$Cl$_2$ and cooled to $-70°$ C. A solution of dimethylsulfoxide in CH$_2$Cl$_2$ (2.0M, 0.130 ml) was added followed 5 minutes later by a solution of the carbapenem 292B (95.7 mg, 0.169 mmol) in CH$_2$Cl$_2$ (0.75 ml). After 10 minutes more, triethylamine (0.060 ml, 0.42 mmol) was added and the reaction mixture was allowed to warm to $-25°$ C. during 15 minutes. The reaction mixture was hydrolyzed with sat. NaHCO$_3$, and then diluted with ethyl acetate and washed successively with sat. NaHCO$_3$, sat. NH$_4$Cl, water, and brine. Drying (MgSO$_4$) and evaporation followed by flash chromatography through 10 g of silica gel (3:2 EtOAc/hexane) yielded 60.5 mg (63%) of the desired aldehyde as a yellow foam.

$^1$H-NMR (300 MHz, CDCl$_3$): δ1.48 (d, J=6.47 Hz, 3H, CH$_3$), 3.24 (dd, J=10, 18.2 Hz, 1H, H1), 3.37 (dd, J=8.9, 18.2 Hz, 1H, H1), 3.48 (dd, J=3.0, 8.2 Hz, 1H, H6), 4.35 (ddd, J=3.0, 8.9, 10 Hz, 1H, H5), 4.55–4.80 (m, 4H, —OCH$_2$C═C), 5.1–5.4 (m, 5H, H8, —C═CH$_2$), 5.75–6.00 (m, 2H, —CH═C), 7.53 (dd, J=1.4, 8.0 Hz, 1H), 7.83 (d, J=8.0 Hz, 1H), 7.9 (s, 1H), 7.91 (d, 1H, partially obscured), 8.15 (dd, J=1.5, 7.9 Hz, 1H), 8.29 (s, 1H), 10.06 (s, 1H, —CHO).

IR (CHCl$_3$): 1785 (β-lactam), 1745 (carbonate), 1725 (ester), 1705 cm$^{-1}$ (aldehyde).

UV (CH$_3$CN): λmax=306 nm (ε=22,700), 252 (ε=19,000), 225 (ε=20,000).

EXAMPLE 294

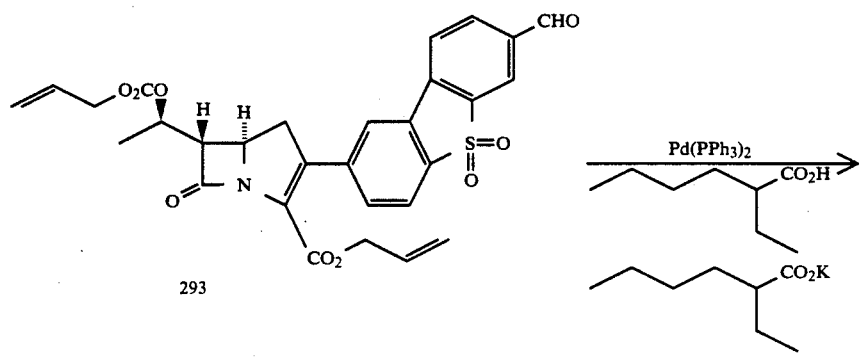

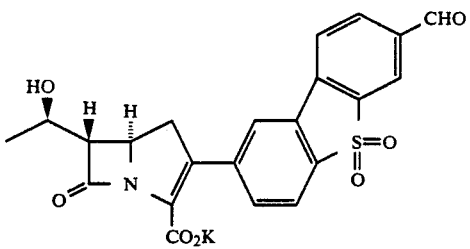

294

Potassium (5R,6S)-2-(2-formyl-9,9-dioxo-6-dibenzothienyl)-6-(1R-hydroxyethyl)carbapen-2-em-3-carboxylate (294)

In an analogous manner to that described in Example 19, the carbapenem 293 (32.2 mg, 0.0571 mmol) was de-allylated to provide the title compound (12.5 mg, 46%) as a yellow lyophilized solid. Compound 294 is also listed in Table III, where it is designated as Example 262.

$^1$H-NMR (300 MHz, 2:1 D$_2$O/CD$_3$CN): $\delta$1.68 (d, J=6.2 Hz, 3H, CH$_3$), 3.54 (dd, J=10, 17 Hz, 1H, H1a), 3.84–3.96 (m, 2H, H1b), 4.55–4.66 (m, 1H, H8), 4.72 (br, t, J=10 Hz, 1H, H5), 8.07 (d, J=8.2 Hz, 1H), 8.28 (d, J=8.2 Hz, 1H), 8.46 (s, 1H), 8.62 (d, J=8 Hz, 1H), 8.67 (d, J=8 Hz, 1H), 8.80 (s, 1H), 10.43 (s, 1H, CHO)

IR (KBr): 1760 ($\beta$-lactam), 1700 (aldehyde), 1600 cm$^{-1}$ (carboxylate).

UV (H$_2$O): $\lambda$max=308 nm ($\epsilon$=25,700).

EXAMPLE 295

Allyl-(5R,6S)-2-(2-cyano-9,9-dioxo-6-dibenzothienl)-6-[1R-(allyloxycarbonyloxy)ethyl]-carbapen-2-em-3-carboxylate (295)

In a manner analogous to that described in Examples 29 and 30, the aldehyde 293 was converted to the title compound in 36% overall yield.

$^1$H-NMR (300 MHz, CDCl$_3$): $\delta$1.48 (d, J=6.3 Hz, 3H, CH$_3$), 3.30 (ABX, J$_{AB}$=18.2 Hz, J$_{AX}$=8.9, J$_{BX}$=10, $\Delta_{AB}$=34.5, 2H, H1), 3.47 (dd, J=2.9, 8.2 Hz, 1H, H6), 4.35 (ddd, J=2.9, 9.0, 9.8 Hz, 1H, H5), 4.45–4.80 (m, 4H, —OCH$_2$C=C), 5.1–5.4 (m, 5H, H8, —C=CH$_2$), 5.75–6.00 (m, 2H, —CH=C), 7.54 (dd, J=1.5, 8.2 Hz, 1H), 7.83 (d, J=8.1 Hz, 1H), 7.84–7.98 (m, 3H), 8.07 (s, 1H).

IR (CHCl$_3$): 2240 (nitrile), 1785 ($\beta$-lactam), 1745 (carbonate), 1730 cm$^{-1}$ (ester).

UV (CH$_3$CN): $\lambda$max=295 nm ($\epsilon$=23,000), 250 nm ($\epsilon$=30,000).

EXAMPLE 296

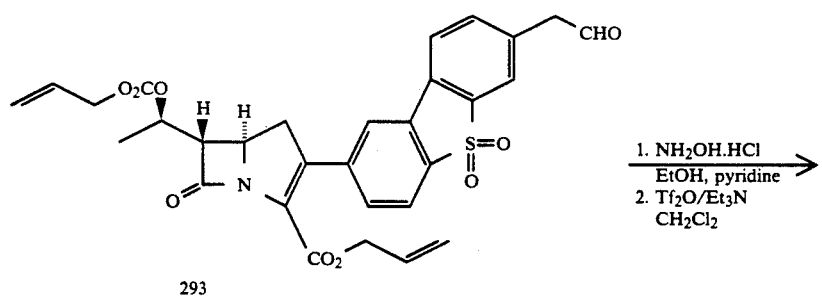

293

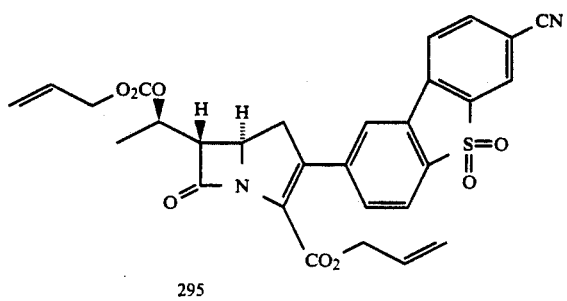

295

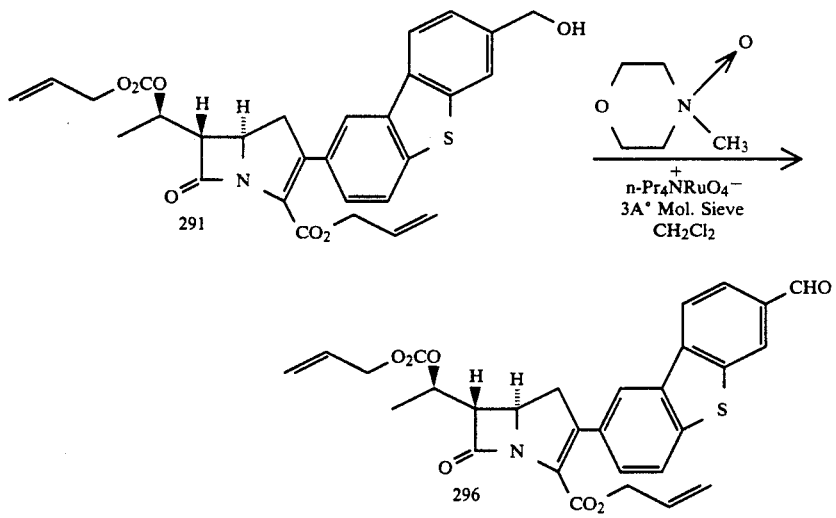

Allyl-(5R,6S)-2-(2-formyl-6-dibenzothienyl)-6-[1R-(allyloxycarbonyloxy)ethyl]-carbapen-2-em-3-carboxylate (296)

In an analogous manner to that described in Example 28, the alcohol 291 (154 mg, 0.289 mmol) was oxidized to provide the aldehyde 296 (122 mg, 79%) as a brown foam.

$^1$H-NMR (300 MHz, CDCl$_3$): δ1.50 (d, J=6.4 Hz, 3H, CH$_3$), 3.25-3.50 (m, 2H, H1), 3.45 (dd, J=2.8, 8.3 Hz, 1H, H6), 4.34 (ddd, J=2.8, 9.2, 9.6 Hz, 1H, H5), 4.55-4.80 (m, 4H, —OCH$_2$C=C), 5.1-5.4 (m, 5H, H8, —C=CH$_2$), 5.75-6.00 (m, 2H, —CH=C), 7.53 (dd, J=1.7, 8.4 Hz, 1H), 7.86 (d, J=8.4 Hz, 1H), 7.96 (dd, J=1.4, 8.2 Hz, 1H), 8.22 (d, J=8.2 Hz, 1H), 8.24 (s, 1H), 8.35 (s, 1H), 10.1 (s, 1H, —CHO).

EXAMPLE 297

Allyl-(5R,6S)-2-[2-(1-hydroxyethyl)-6-dibenzothienyl]-6-[1R-(allyloxycarbonyloxy)ethyl]-carbapen-2-em-3-carboxylate (297)

A solution of the aldehyde 296 (122 mg, 0.023 mmol) in THF was cooled to −70° C. and a solution of methylmagnesium bromide in butyl ether (1.0M, 0.240 ml, 1.05 equiv.) was added dropwise. After 20 minutes, the reaction was quenched by the addition of a solution of acetic acid in THF (2.0M, 0.120 ml). The reaction mixture was hydrolyzed with sat. NH$_4$Cl, diluted with ethyl acetate, and washed successively with sat. NH$_4$Cl, water, and brine. Drying (MgSO$_4$) and evaporation gave a yellow oil which was separated by preparative TLC on silica gel (7:3 EtOAc/hexane) to yield 58.0 mg (46%) of the tile compound 297 and return 20.0 mg (16%) of unreacted starting material.

$^1$H-NMR (300 MHz, CDCl$_3$): δ1.49 (d, J=6.3 Hz, 3H, CH$_3$), 1.55 (d, J=6.4 Hz, 3H, CH$_3$), 3.25-3.45 (m, 2H, H1), 3.44 (dd, J=2.8, 8.4 Hz, 1H, H6), 4.31 (ddd, J=2.8, 9.2, 9.6 Hz, 1H, H5), 4.55-4.75 (m, 4H, —OCH$_2$C=C), 5.0-5.1 (m, 1H, ArCH—O), 5.1-5.4 (m,

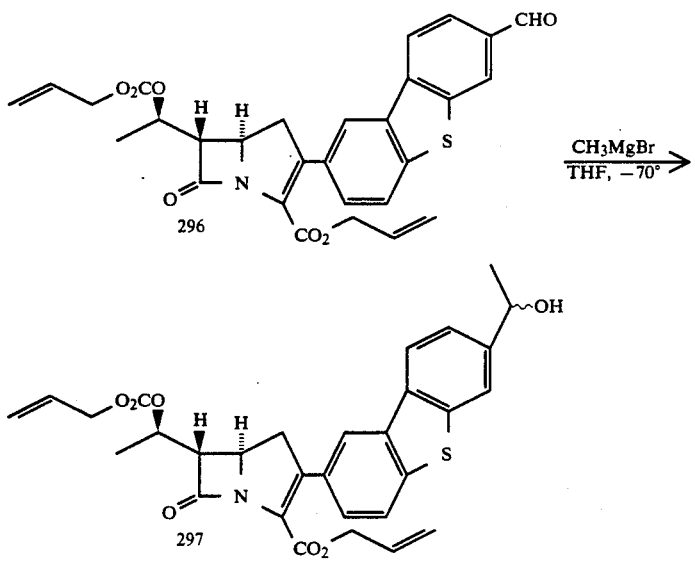

5H, H8, —C=CH₂), 5.75-6.00 (m, 2H, —CH=C), 7.35-7.40 (m, 2H), 7.78 (d, J=8.4 Hz, 1H), 7.86 (s, 1H), 8.05 (d, J=8.2 Hz, 1H), 8.11 (d, J=1.7 Hz, 1H).

¹H-NMR (300 MHz, CDCl₃): δ1.47 (d, J=6.4 Hz, 6H, CH₃), 3.15-3.40 (m, 2H, H1), 3.4-3.5 (m, 1H, H6), 4.32 (ddd, J=2.8, 9.3, 9.5 Hz, 1H, H5), 4.55-4.75 (m, 4H, —OCH₂=C), 4.85-4.95 (m, 1H, ArCHO—), 5.1-5.4 (m, 5H, H8, —C=CH₂), 5.75-6.00 (m, 2H, —CH=C),

EXAMPLE 298

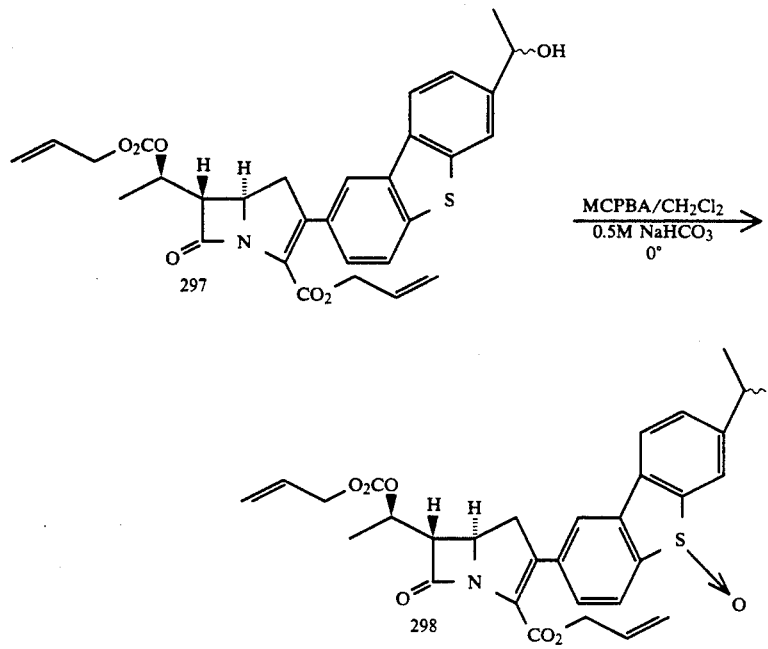

Allyl-(5R,6S)-2-[2-(1-hydroxyethyl)-9-oxo-6-dibenzothienyl]-6-[1R-(allyloxycarbonyloxy)ethyl]-carbapen-2-em-3-carboxylate (298)

In an analogous manner to that described in Example 27, carbapenem 297 (58.0 mg, 0.106 mmol) was oxidized to provide sulfoxide 298 (38.6 mg, 65%) along with a small amount of the corresponding sulfone, which was not isolated.

7.35-7.45 (m, 1H), 7.53 (d, J=8.0 Hz, 1H), 7.6-7.7 (m, 1H), 7.74 (s, 1H), 7.85-7.95 (m, 2H).

EXAMPLE 299

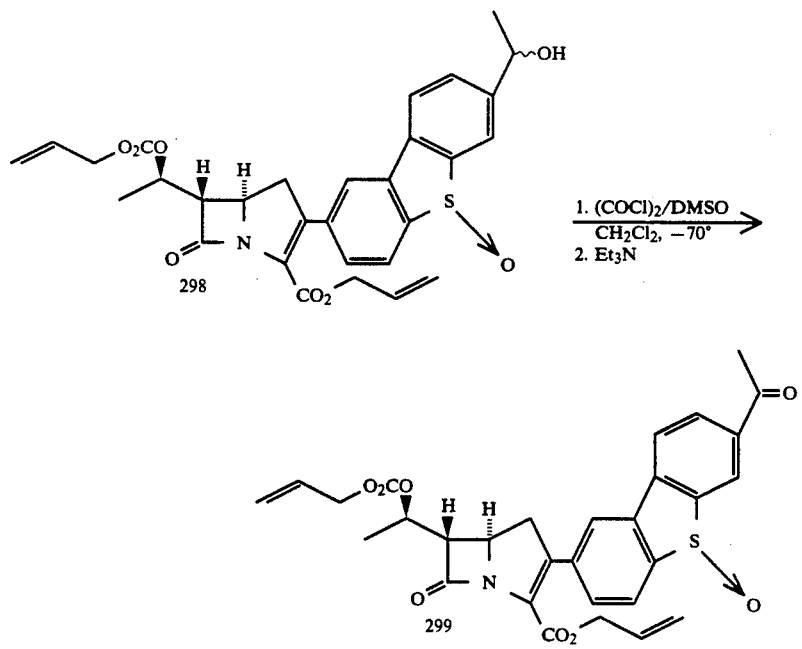

Allyl-(5R,6S)-2-[2-acetyl-9-oxo-6-dibenzothienyl)-6-[1R-(allyloxycarbonyloxy)ethyl]-carbapen-2-em-3-carboxylate (299)

In a manner analogous to that described in Example 293, carbapenem 298 (38.6 mg, 0.0685 mmol) was oxidized to provide the title compound (26.1 mg, 68%) as a yellow oil.

$^1$H-NMR (300 MHz, CDCl$_3$): δ1.48 (d, J=6.2 Hz, 3H, CH$_3$), 2.66 (s, 3H, —COCH$_3$), 3.18–3.43 (m, 2H, H1), 3.47 (dd, J=2.8, 8.2 Hz, 1H, H6), 4.34 (dt, J=2.8, 9.4 Hz, 1H, H5), 4.55–4.75 (m, 2H, —OCH$_2$C=C), 5.1–5.4 (m, 5H, H8, —C=CH$_2$), 5.75–6.00 (m, 2H, —CH=C), 7.45–7.55 (m, 1H), 7.8–7.9 (m, 2H), 7.99 (d, J=8.1 Hz, 1H), 8.20 (d, J=7.3 Hz, 1H), 8.53 (s, 1H).

IR (CHCl$_3$): 1785 (β-lactam), 1745 (carbonate), 1725 (ester), 1690 cm$^{-1}$ (ketone).

UV (CH$_3$CN): λmax=350 nm (ε=20,000), 264 (ε=19,400), 231 (ε=18,500).

EXAMPLE 300

Allyl-(5R,6S)-2-(2-carbamoyl-6-dibenzothienyl)-6-[1R-(allyloxycarbonyloxy)ethyl]carbapen-2-em-3-carboxylate (300)

In an analogous manner to that described in Examples 31–3, but starting with the ylide 290, the title carbapenem 300 was obtained as a light yellow foam.

$^1$H-NMR (300 MHz, CDCl$_3$): δ1.49 (d, J=6.3 Hz, 3H, CH$_3$), 3.23–3.46 (m, 2H, H1), 3.47 (dd, J=2.9, 8.4 Hz, 1H, H6), 4.33 (ddd, J=2.9, 9.1, 9.6 Hz, 1H, H5), 4.55–4.80 (m, 4H, —OCH$_2$=C), 5.1–5.4 (m, 5H, H8, —C=CH$_2$), 5.75–6.00 (m, 2H, —CH=C), 7.48 (dd, J=1.7, 8.4 Hz, 1H), 7.80 (d, J=8.3 Hz, 1H), 7.83 (dd, J=1.4, 8.3 Hz, 1H), 8.09 (d, J=8.3 Hz, 1H), 8.14 (d, J=1.5 Hz, 1H), 8.23 (d, J=1.4 Hz, 1H).

IR (CHCl$_3$): 3530, 3420 (NH), 1780 (β-lactam), 1745 (carbonate), 1725 esterm 1680 cm$^{-1}$ (amide).

UV (CH$_3$CN): λmax=298 nm (ε=17,800), 278 (ε=19,600), 244 (ε=25,400).

EXAMPLE 301

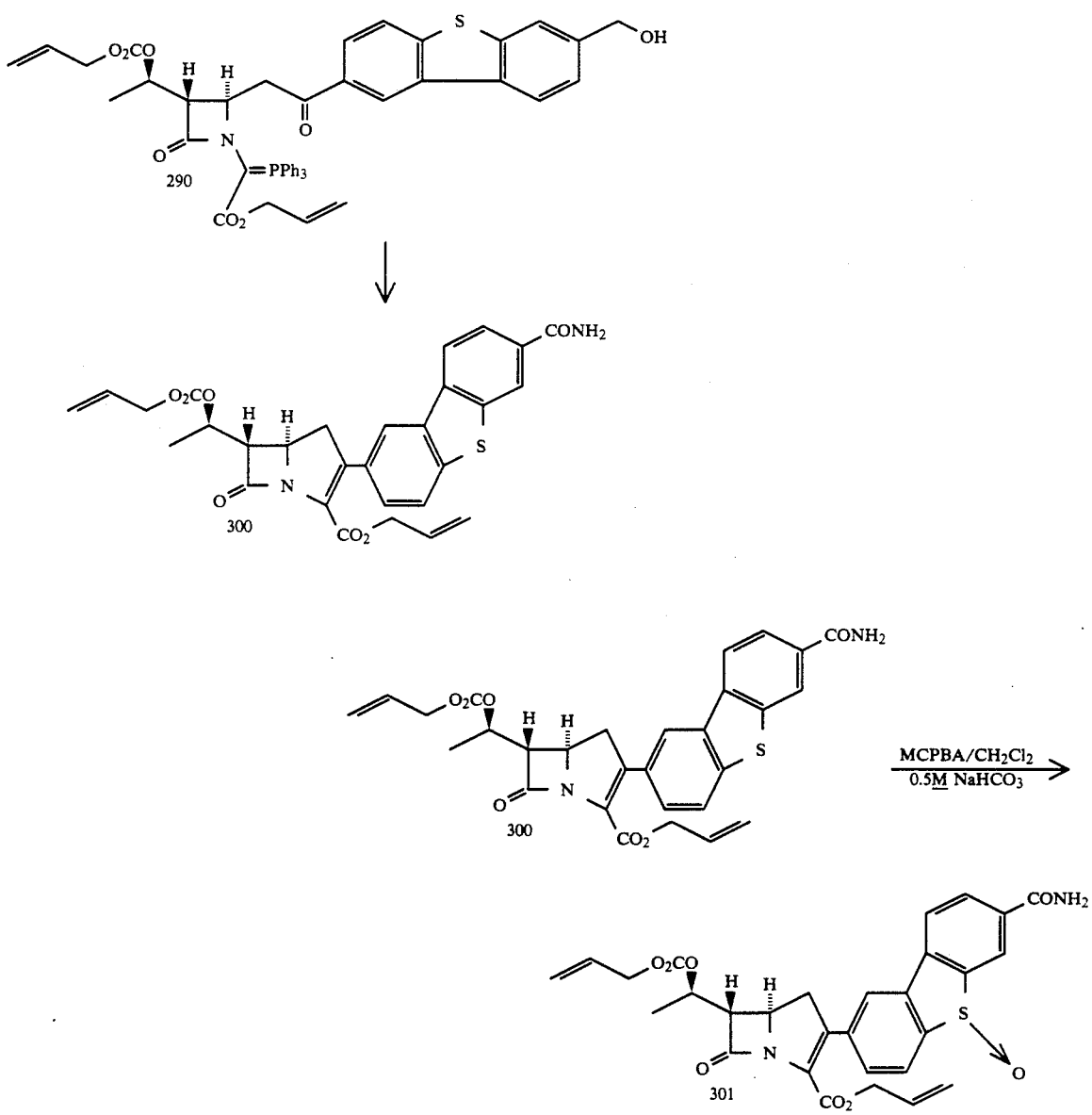

Allyl-(5R,6S)-2-(2-carbamoyl-9-oxo-6-dibenzothienyl)-6-[1R-(allyloxycarbonyloxy)ethyl]carbapen-2-em-3-carboxylate (301)

In a manner analogous to that described in Example 27, 138 mg (0.252 mmol) of carbapenem 300 was oxidized to yield 68.7 mg (48%) of the title sulfoxide as a yellow solid along with a small amount of the corresponding sulfone, which was not isolated.

$^1$H-NMR (300 MHz, CDCl$_3$): δ1.47 (d, J=6.4 Hz, 3H, CH$_3$), 3.22(dd, J=10, 18 Hz, 1H, H1), 3.39 (dd, J=8.6, 18 Hz, 1H, H1), 3.45–3.55 (m, 1H, H6), 4.33 (br t, J=9 Hz, 1H, H5), 4.55–4.80 (m, 4H, —OCH$_2$C=C), 5.1–5.4 (m, 5H, H8, —C=CH$_2$), 5.75–6.00 (m, 2H, —CH=C), 7.4–7.5 (m, 1H), 7.70 (dd, J=2.9, 8.1 Hz, 1H), 7.77 (d, J=9.0 Hz, 1H), 7.92 (d, J=8.1 Hz, 1H), 7.96–8.06 (m, 1H), 8.4 (bs, 1H).

IR (CHCl$_3$): 1785 (β-lactam), 1745 (carbonate), 1725 (ester), 1680 cm$^{-1}$ (amide).

UV (CH$_3$CN): λmax=298 nm (ε=13,900), 258 (ε=16,500), 237 (ε=16,200). EXAMPLE 302

Potassium (5R,6S)-2-(2-carbamoyl-9-oxo-6-dibenzothienyl)-6-(1R-hydroxyethyl)-carbapen-2-em-3-carboxylate (302)

In an analogous manner to that described in Example 19, the carbapenem 301 (47.0 mg, 0.0835 mmol) was de-allylated to provide the title compound (17.4 mg, 44%) as a yellow lyophilized solid. Compound 302 is also listed in Table III, where it is designated as Example 217.

$^1$H-NMR (300 MHz, 2:1 D$_2$O/CD$_3$CN): δ1.68 (d, J=6.4 Hz, 3H, CH$_3$), 3.53 (dd, J=10, 17 Hz, 1H, H1a), 3.80–3.96 (m, 2H, H1b, H6), 4.55–4.65 (m, 1H, H8), 4.7 (dd, J=2.8, 9.5 Hz, 1H, H5), 7.99 (dd, J=1.5, 8.1 Hz, 1H), 8.37 (d, J=8.1 Hz, 1H), 8.39 (s, 1H), 8.47 (d, J=8.2 Hz, 1H), 8.53 (dd, J=1.5, 8.2 Hz, 1H), 8.8 (d, J=1.5 Hz, 1H).

IR (KBr): 1760 (β-lactam), 1680 (amide), 1600 cm$^{-1}$ (carboxylate).

UV (H$_2$O): λmax=301 nm (δ=14,200), 255 nm (δ=13,900).

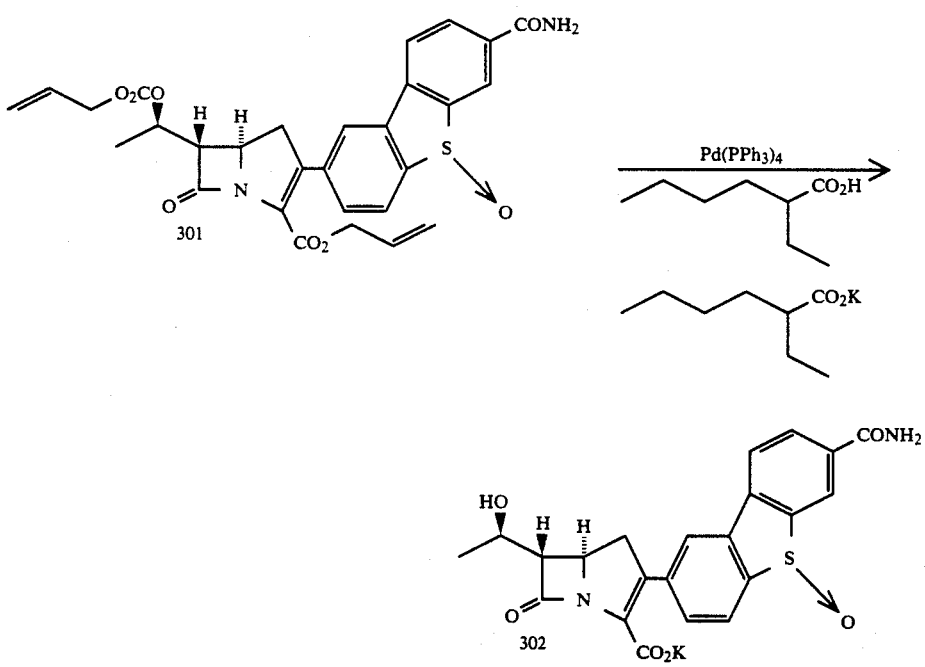

EXAMPLE 303

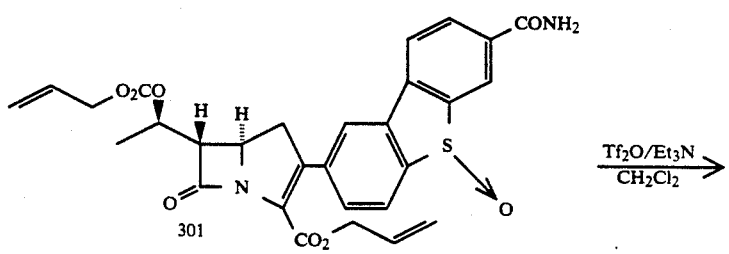

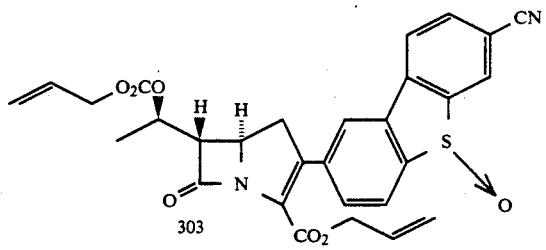

Allyl-(5R,6S)-2-(2-cyano-9-oxo-6-dibenzothienyl)-6-[1R-(allyloxycarbonyloxy)ethyl]carbapen-2-em-3-carboxylate (303)

A solution of the amide 301 (68.7 mg, 0.122 mmol) in 1.2 ml of CH₂Cl₂ was cooled to −70° C. and triethylamine (0.037 ml, 0.27 mmol) was added followed by trifluoromethanesulfonic anhydride (0.023 ml, 0.13 mmol). The orange reaction mixture was allowed to warm to −40° C. during 30 minutes and was then hydrolyzed with sat. NaHCO₃, diluted with ethyl acetate, and washed successively with sat. NaHCO₃, sat. NH₄Cl, water, and brine. Drying (MgSO₄) and evaporation gave an oil which was separated by preparative TLC on silica gel (EtOAc) to yield 13.5 mg (20%) of the title compound as a yellow foam and 14.3 mg (21%) of unreacted starting material.

¹H-NMR (300 MHz, CDCl₃): δ1.48 (d, J=6.35 Hz, 3H, CH₃), 3.18–3.44 (m, 2H, H1), 3.47 (dd, J=2.9, 8.3 Hz, 1H, H6), 4.35 (ddd, J=2.9, 9.2, 9.6 Hz, 1H, H5), 4.56–4.76 (m, 4H, —OCH₂C=C), 5.1–5.4 (m, 5H, H8, —C=CH₂), 5.75–6.00 (m, 2H, —CH=C), 7.48–7.56 (m, 1H), 7.85–7.92 (m, 3H), 8.01 (d, J=8.0 Hz, 1H), 8.25 (s, 1H).

IR (CHCl₃): 2240 (nitrile), 1785 (β-lactam), 1745 (carbonate), 1725 cm⁻¹ (ester).

EXAMPLE 304

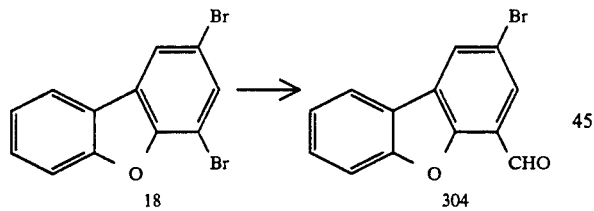

1-Formyl-3-bromodibenzofuran

To a stirred solution of 1,3-dibromobenzofuran 18 (10 g, 30.9 mmol) in anhydrous THF (250 mL) at −78° C. under nitrogen was added a 2.5M butyllithium in hexane solution (13.6 mL, 33.9 mmol). The resulting red solution was warmed to −50° C. and held there for 10 min. before anhydrous DMF (2.6 mL, 33.9 mmol) was added dropwise. The resulting rust colored solution was stirred an additional 20 min. at −50° to −40° C. before being quenched with saturated ammonium chloride solution (25 mL). The THF was removed under vacuum and the residue was dissolved in ethyl acetate (EtOAc) and washed sequentially with water, saturated aqueous ammonium chloride solution, water and brine. The organic solution was then dried with magnesium sulfate and decolorized with Norite. The mixture was then filtered and concentrated under vacuum. The residue was triturated with ether/hexane to provide 4.0 g of pale yellow flakes of dibenzofuran 304. The mother liquor was then chromatographed (silica gel, 30% EtOAc in hexanes) to provide an additional 2.1 g of dibenzofuran 304 (total yield: 73%).

¹H-NMR (300 MHz, CDCl₃): δ7.42 (t, J=7.5 Hz, 1H), 7.55 (t, J=7.3 Hz, 1H), 7.65 (d, J=7.9 Hz, 1H), 7.92 (d, J=7.7 Hz, 1H), 8.02 (d, J=1.6 Hz, 1H), 8.25 (d, J=1.9 Hz, 1H), 10.51 ppm (s, 1H).

EXAMPLE 305

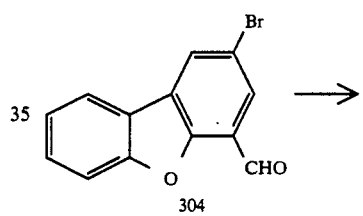

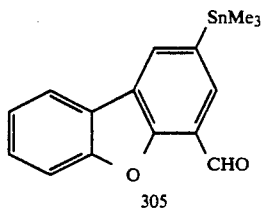

1-Formyl-3-(trimethylstannyl)dibenzofuran (305)

To a stirred solution of the dibenzofuran 304 (5 g, 18.2 mmol) in toluene (91 mL) was added hexamethylditin (3.9 mL, 20 mmol), tetrakis-(triphenylphosphine)-palladium(0) (1.05 g, 5 mol %) and triphenylphosphine (0.276 g, 5 mol %). Nitrogen was bubbled through the solution for 5 min., and the reaction solution was heated at reflux for 15 minutes under a nitrogen atmosphere. The reaction mixture was then poured into ether and the organic solution was washed with water (3 times) and then brine (2 times). The solution was dried with magnesium sulfate, filtered and concentrated under vacuum. The residue was purified by flash chromatography (silica gel, 5% EtOAc in CH₂Cl₂) and crystallized to provide 4.3 g (66% yield) of stannane 305 as a white solid.

¹H-NMR (300 MHz, CDCl₃): δ0.40 (s, 9H), 7.40 (t, J=6.3 Hz, 1H), 7.52 (t, J=6.3 Hz, 1H), 7.68 (d, J=6.1 Hz, 1H), 8.00 (m, 2H), 8.19 (s, 1H), 10.62 ppm (s, 1H).

EXAMPLE 306

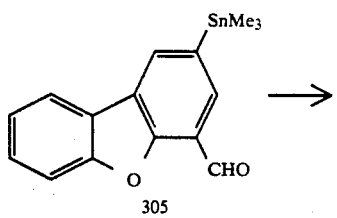

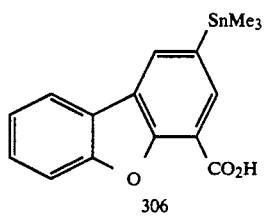

1-Carboxy-3-(trimethylstannyl)dibenzofuran (306)

A solution of tetra-n-butylammonium permanganate (5.1 g, 14.0 mmol) in anhydrous pyridine (35 mL) was transferred via cannula needle into a solution of the stannane 305 (5.0 g, 14.0 mmol) in anhydrous pyridine (35 mL) at 0° C. under a nitrogen atmosphere. The reaction was stirred for 30 min., then saturated aqueous sodium sulfate (50 mL) was added to quench the reaction. The mixture was then poured into ether and the layers separated. The organic layer was washed with 2N aqueous HCl (6 times with 100 mL), water (2 times) and then brine (2 times). The solution was dried with magnesium sulfate, then filtered and concentrated under vacuum to provide 4.8 g (92% yield) of the stannane 306 as a white solid.

$^1$H-NMR (300 MHz, CDCl$_3$): δ0.40 (s, 9H), 7.39 (t, J=8.4 Hz, 1H), 7.52 (t, J=8.4 Hz, 1H), 7.71 (d, J=8.4 Hz, 1H), 8.00 (d, J=7.8 Hz, 1H), 8.27 (s, 1H), 8.29 ppm (s, 1H).

EXAMPLE 307

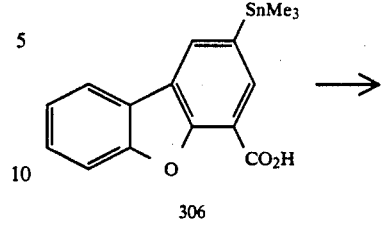

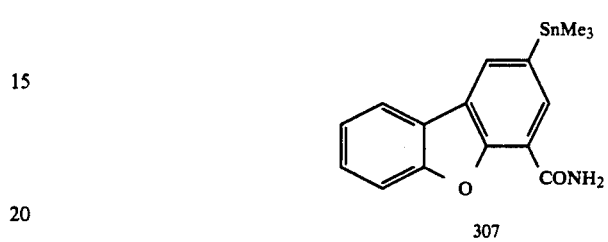

1-Carbamoyl-3-(trimethylstannyl)dibenzofuran (307)

To a stirred solution of the stannane 306 (1.1 g, 2.96 mmol) in anhydrous acetonitrile (5 mL) and THF (15 mL) under a nitrogen atmosphere was added 1-(3-dimethylaminopropyl)-3-ethylcarbodiimide hydrochloride (1.13 g, 5.9 mmol) and 1-hydroxybenzotriazole hydrate (1.2 g, 8.9 mmol). The solution was stirred 30 min., then 11 mL of a 2.6M ethanolic ammonia solution was added. The resulting milky white solution was stirred an additional 30 min. before being quenched with saturated aqueous ammonium chloride. The solvents were removed under vacuum and the residue taken up in ether (75 mL) and EtOAc (75 mL). The solution was washed with water (3 times) and brine (2 times), then dried with magnesium sulfate and filtered. The solution was concentrated under vacuum and the residue was purified by flash chromatography (silica gel, 35% EtOAc in hexanes) to provide 979 mg (88% yield) of stannane 307 as a white solid.

$^1$H-NMR (300 MHz, CDCl$_3$): δ0.38 (s, 9H), 6.10 (broad s, 1H), 7.41 (t, J=7.2 Hz, 1H), 7.49 (t, J=7.2 Hz, 1H), 7.54–7.66 (m, 2H), 7.99 (d, J=7.8 Hz, 1H), 8.22 (s, 1H), 8.35 ppm (s, 1H).

EXAMPLE 308

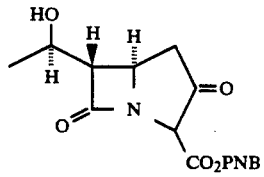

i) Tf$_2$O/ DIPA
ii) TMSOTf/ TEA iii) Pd$_2$(DBA)$_3$·CHCl$_3$/ZnCl$_2$
1-methyl-2-pyrrolidinone

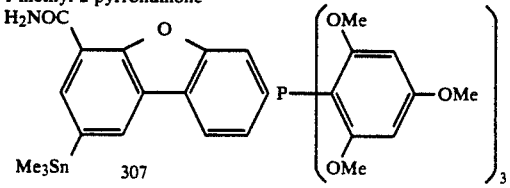

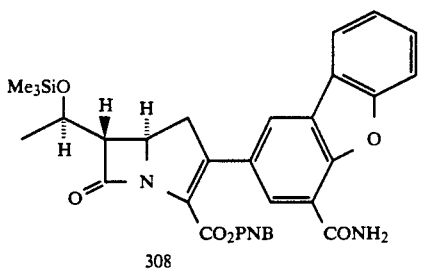

308 p-Nitrobenzyl-(5R,6S)-2-(1-carbamoyl-3-dibenzofuranyl)-6-[1R-(trimethylsilyloxy)-ethyl]carbapen-2-em-3-carboxylate (308)

A dry 15 mL receiving flask was charged with the bicyclic β-ketoester A (143 mg, 0.41 mmol) and a magnetic stir bar and the system was purged with nitrogen. Anhydrous tetrahydrofuran (2 mL) was added and upon dissolution of A, the reaction vessel was cooled to −78° C. under $N_2$. Diisopropylamine (0.063 mL, 0.45 mmol) was then added and the stirring was continued for 10 minutes. Trifluoromethanesulfonic anhydride (0.075 mL, 0.45 mmol) was added, followed by stirring for an additional 15 min. Triethylamine (0.062 mL, 0.45 mmol) was then added, followed by trimethylsilyl trifluoromethanesulfonate (0.087 mL, 0.45 mmol).

While the above reaction was stirred for 20 min., the organostannane 307 (168 mg, 0.45 mmol), tris(dibenzylideneacetone)dipalladium-chloroform (8.5 mg, 0.0082 mmol) and tris(2,4,6-trimethoxyphenyl)-phosphine (17.4 mg, 0.033 mmol) were weighed into a single vial and the vial was purged with nitrogen. When the above reaction time had elapsed, N-methylpyrrolidinone (2 mL) was added to the initial reaction mixture followed by the previously weighed solids. A 0.87M zinc chloride in ether solution (0.52 mL, 0.45 mmol) was then added. The low temperature bath was then removed and the reaction vessel was placed in a luke warm water bath to allow it to quickly reach ambient temperature. After reaching ambient temperature, the mixture was stirred for 20 minutes.

The reaction was then quenched by pouring the contents of the flask into a 125 mL separatory funnel containing diethyl ether, ethyl acetate and water. The organic phase was separated and washed with water and brine. The organic phase was dried over magnesium sulfate. The mixture was then filtered and the solvent removed under vacuum. Flash column chromatography of the residue (silica gel, 60–65% ethyl acetate/hexanes) provided 164 mg (67%) of carbapenem 308 as a slightly yellowish foam.

$^1$H-NMR (300 MHz, CDCl$_3$): δ0.15 (s, 9H), 1.30 (d, J=6.2 Hz, 3H), 3.28 (dd, J=6.4, 2.7 Hz, 1H), 3.31–3.45 (m, 2H), 4.21–4.35 (complex m, 2H), 5.21 (AB$_q$, J$_{AB}$=13.5 Hz, Δν$_{AB}$=50.1 Hz, 2H), 6.17 (broad singlet, 2H), 7.35–7.41 (m, 3H), 7.48–7.54 (m, 2H), 7.60 (d, J=8.3 Hz, 1H), 7.83 (d, J=7.2 Hz, 1H), 7.97 (d, J=8.8 Hz, 2H), 8.09 (d, J=2.0 Hz, 1H), 8.18 ppm (d, J=1.9 Hz, 1H);

IR (CHCl$_3$): 3510, 3400, 1770, 1720, 1675, 1590, 1520 cm$^{-1}$;

UV (CH$_3$CN): λ$_{max}$ 290 nm (ε11,000); λ$_{max}$ 250 nm (ε13,300).

EXAMPLE 309

Potassium (5R,6S)-2-(1-carbamoyl-3-dibenzofuranyl)-6-[1R-hydroxyethyl]carbapen-2-em-3-carboxylate (309)

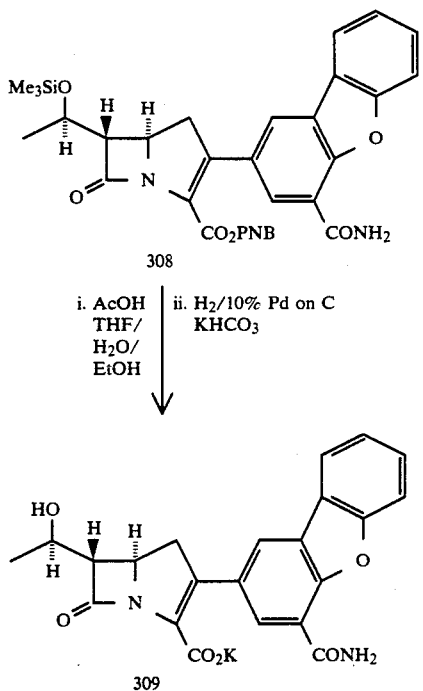

To a stirred solution of carbapenem 308 (170 mg, 0.277 mmol) in 25 mL of THF/water/EtOH (1.3:1:1.3) was added glacial acetic acid (0.004 mL, 0.07 mmol). The solution was heated at 35° C. for 70 min., and then potassium bicarbonate (55 mg, 0.55 mmol) was added followed by 10% palladium on carbon (17 mg, 10 wt. %). The reaction vessel was placed under a balloon filled with hydrogen and stirred in this atmosphere for 1 hour at ambient temperature. The reaction mixture was then filtered through a pad of Celite and the pad was rinsed with HPLC grade water. The organic layer was removed under vacuum and the aqueous solution which remained was frozen and lyophilized at 0° C. The residue was purified via reverse-phase thin layer chromatography (4:1 water:acetonitrile) to provide 99 mg of the carbapenem 309 (80.7% yield) as a white solid.

This example illustrates an alternative synthesis of carbapenem 32, the product compound of Example 34.

EXAMPLE 310

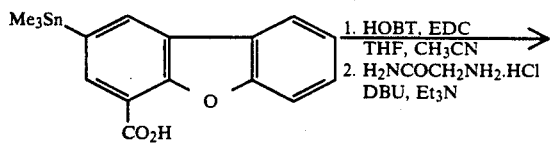

1-[N-(carbamoyl)methyl]carbamoyl-3-trimethylstannyldibenzofuran (310)

To a stirred solution of the stannyl-acid 306 (500 mg, 1.3 mmol) in dry THF (7.5 mL) under $N_2$ was added 1-(3-dimethylaminopropyl)-3-ethylcarbodiimide hydrochloride (307 mg, 1.6 mmol, 1.2 eq) and 1-hydroxybenzotriazole hydrate (270 mg, 2.0 mmol, 1.5 eq). Anhydrous $CH_3CN$ was added to solubilize the resulting suspension and the mixture was stirred for 30 minutes. A solution of glycinamide hydrochloride (293 mg, 2.6 mmol, 2.0 eq), triethylamine (0.46 mL, 3.3 mmol, 2.5 eq), and DBU (0.2 mL, 1.3 mmol, 1.0 eq) in DMF (10 mL) was then added. After 20 minutes had elapsed, the reaction mixture was poured into EtOAc (200 mL) and washed with water (4×25 mL) and brine (2×25 mL), then dried ($MgSO_4$), filtered, and concentrated in vacuo. Purification by silica gel flash column chromatography (EtOAc) provided 550 mg (96%) of 310 as a white solid.

$^1$H-NMR (300 MHz, $CDCl_3$): δ0.38 (s, 9H), 4.31 (d, J=5.6 Hz, 2H), 5.47 (broad s, 1H), 6.27 (broad s, 1H), 7.40 (t, J=7.9 Hz, 1H), 7.50 (t, J=7.8 Hz, 1H), 7.66 (d, J=8.2 Hz, 1H), 8.00 (d, J=7.6 Hz, 1H), 8.20 (s, 1H), 8.27-8.32 (m, 2H).

IR ($CHCl_3$): 3480, 3430, 3000, 1690 cm$^{-1}$.

EXAMPLE 311

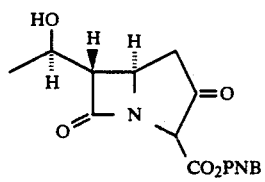

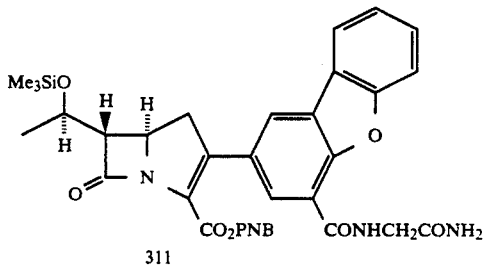

p-Nitrobenzyl-(5R,6S)-2-{1-[N-(carbamoyl)methyl]-carbamoyl-3-dibenzofuranyl}-6-[1R-(trimethylsilyloxy)-ethyl]carbapen-2-em-3-carboxylate (311)

In a manner analogous to that described in Example 308 but employing the stannane 310 (125 mg, 0.29 mmol) as a starting material, the title carbapenem (126 mg, 65%) was obtained.

$^1$H-NMR (300 MHz, $CDCl_3$): δ0.15 (s, 9H), 1.30 (d, J=6.2 Hz, 3H), 3.28 (dd, J=6.2, 2.7 Hz, 1H), 3.33–3.38 (m, 2H), 4.24–4.34 (m, 4H), 5.24 (ABq, J=13.5 Hz, $\Delta\nu_{AB}$=50.8 Hz, 2H), 5.58 (broad s, 1H), 6.22 (broad s, 1H), 7.36–7.43 (m, 3H), 7.52 (t, J=7.2 Hz, 1H), 7.74 (d, J=8.2 Hz, 1H), 7.83 (d, J=7.7 Hz, 1H), 8.01 (d, J=8.8 Hz, 2H), 8.07 (d, J=1.7 Hz, 1H), 8.17 (d, J=1.7 Hz, 1H), 8.27 (m, 1H).

EXAMPLE 312

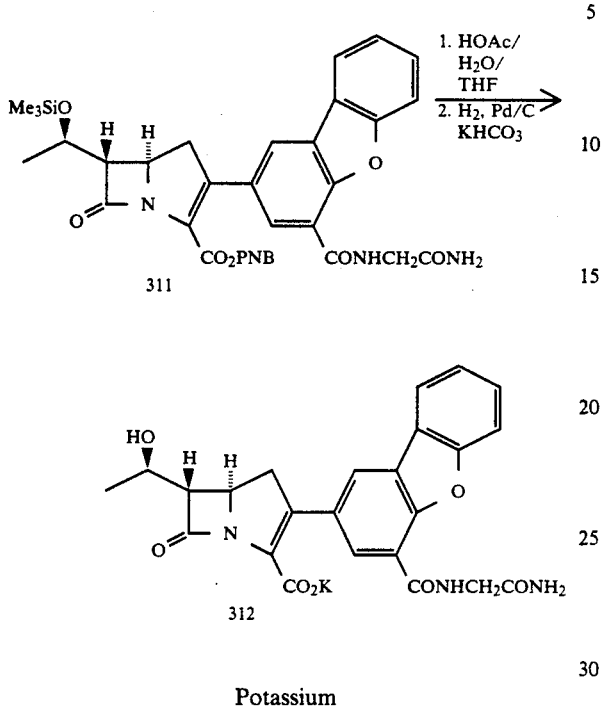

Potassium (5R,6S)-2-{1-[N-(carbamoyl)methyl]carbamoyl-3-dibenzofuranyl}-6-(1R-hydroxyethyl)-carbapen-2-em-3-carboxylate (312)

In an analogous manner to that described in Example 309, 40.7 mg (0.068 mmol) of the carbapenem 311 was deprotected to yield 22 mg (74%) of the title compound as a lyophilized solid. Compound 312 is also listed in Table III where it is designated as Example 97.

$^1$H-NMR (300 MHz, 2:1 D$_2$O/CD$_3$CN) 1.65 (d, J=6.3 Hz, 3H), 3.52 (dd, J=15, 9 Hz, 1H), 3.82-3.84 (m, 2H), 4.55 (s, 2H), 4.58-4.68 (m, 2H), 7.84 (t, J=7.3 Hz, 1H), 7.96 (t, J=8.2 Hz, 1H), 8.08 (d, J=8.2 Hz, 1H), 8.35 (d, J=1.6 Hz, 1H), 8.47 (d, J=7.3 Hz, 1H), 8.60 (d, J=1.6 Hz, 1H).

UV (H$_2$O): λ=296 nm (ε=14,000).

EXAMPLE 313

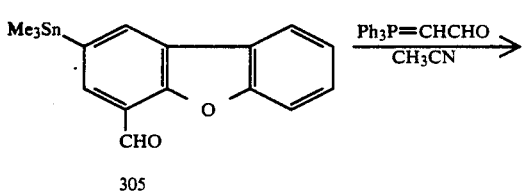

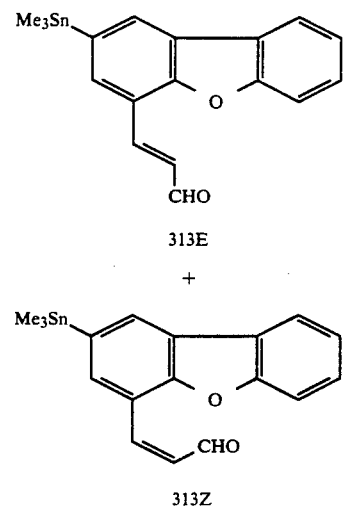

1-(E-propenal-3-yl)-3-trimethylstannyl-dibenzofuran (313E) and 1-(Z-propenal-3-yl)-3-trimethylstannyldibenzofuran (313Z)

A mixture of the stannyl-aldehyde 305 (207 mg, 0.58 mmol) and (triphenylphosphoranylidene)-acetaldehyde (1.06 g, 3.4 mmol, 6.0 eq.) in CH$_3$CN (10 mL) was stirred at reflux for 5 hours under N$_2$. The reaction mixture was poured into ether (175 mL) and washed with saturated NH$_4$Cl (2×25 mL), water (2×25 mL), and brine (2×25 mL), then dried (MgSO$_4$), filtered, and evaporated in vacuo. Purification by flash column chromatography (1:1 CH$_2$Cl$_2$/hex) provided 143.5 mg (64.5%) of the E olefin followed by 42 mg (19%) of the Z olefin.

E-Isomer (313E)

$^1$H-NMR (300 MHz CDCl$_3$): δ0.39 (s, 9H), 7.30–7.40 (m, 2H), 7.49 (t, J=7.1 Hz, 1H), 7.55–7.64 (m, 2H), 7.78 (d, J=16 Hz, 1H), 7.98 (d, J=7.7 Hz, 1H), 8.10 (s, 1H), 9.80 (d, J=7.9 Hz, 1H).

IR (CHCl$_3$) 3060, 3010, 1675, 1460 cm$^{-1}$.

Z-Isomer (313Z)

$^1$H-NMR (300 MHz CDCl$_3$): δ0.38 (s, 9H), 6.39 (dd, J=15, 8 Hz, 1H), 7.28–7.42 (m, 2H), 7.49 (t, J=7.1 Hz, 1H), 7.54–7.68 (m, 2H), 7.98 (d, J=7.0 Hz, 1H), 8.02 (s, 1H), 9.66 (d, J=7.9 Hz, 1H).

EXAMPLE 314

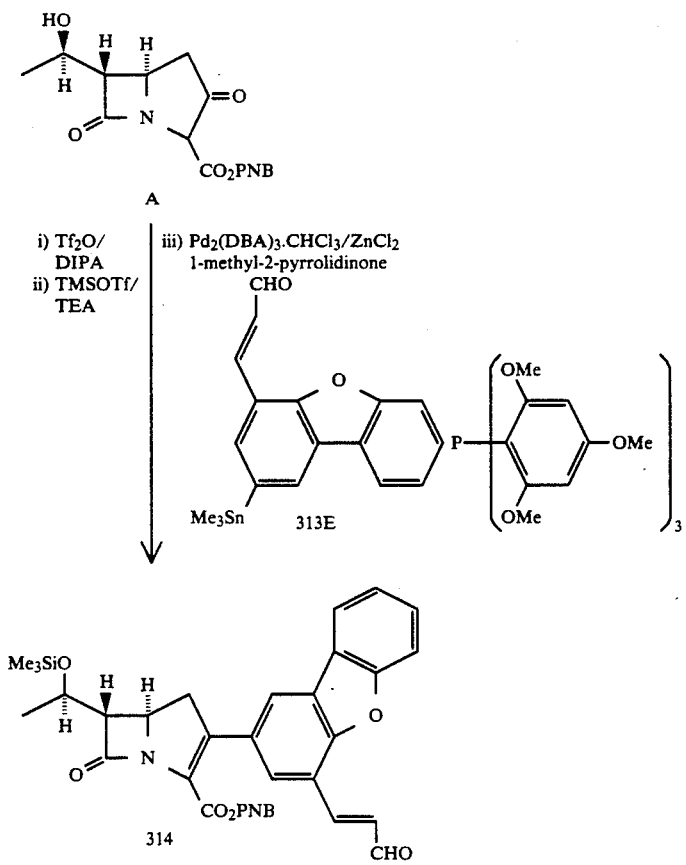

p-Nitrobenzyl-(5R,6S)-2-[1-(E-propenal-3-yl)-3-dibenzofuranyl]-6-[1R-(trimethylsilyloxy)ethyl]-carbapen-2-em-3-carboxylate (314)

Following the procedure described in Example 308, but employing the stannane 313E (137 mg, 0.36 mmol) as a starting material, the title carbapenem (154 mg, 69%) was prepared.

$^1$H-NMR (300 MHz, CDCl$_3$): δ0.38 (s, 9H), 1.31 (d, J=6.2 Hz, 3H), 3.28–3.28 (m, 3H), 4.25–4.36 (m, 2H), 5.26 (AB$_q$, J=13.7 Hz, Δν$_{AB}$=56.3 Hz, 2H), 7.29 (d, J=7.7 Hz, 1H), 7.38 (t, J=7.9 Hz, 1H), 7.45 (d, J=8.7 Hz, 2H), 7.52 (t, J=7.8 Hz, 1H), 7.62–7.65 (m, 2H), 7.70 (d, J=16 Hz, 1H), 7.85 (d, J=7.7 Hz, 1H), 7.98 (d, J=1.6 Hz, 1H), 8.00–8.05 (d, J=8.5 Hz, 2H), 9.79 (d, 7.2 Hz, 1H).

IR (CHCl$_3$): 3010, 2960, 1775, 1725, 1680 cm$^{-1}$.

UV (CH$_3$CN): λ$_1$=259 nm (ε$_1$=49,000), λ$_2$=283 nm (ε$_2$=52,000), λ$_3$=309 nm (ε$_3$=42,000).

EXAMPLE 315

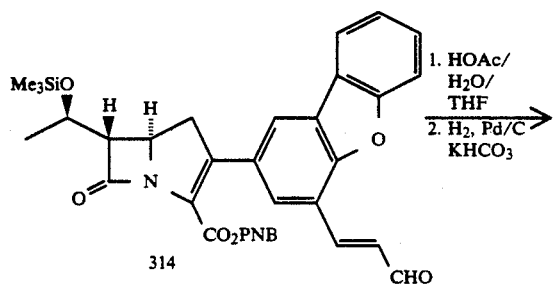

-continued

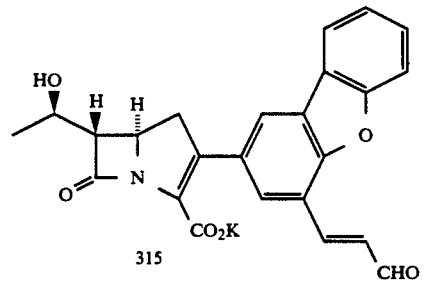

Potassium (5R,6S)-2-[1-(E-propenal-3-yl)-3-dibenzofuranyl]-6-(1R-hydroxyethyl)-carbapen-2-em-3-carboxylate (315)

In a manner analogous to that described in Example 309, the carbapenem 314 (44 mg, 0.070 mmol) was deprotected to yield the title compound (11.2 mg, 35%) as a lyophilized solid.

$^1$H-NMR (300 MHz, 2:1 D$_2$O/CD$_3$CN) 1.69 (d, J=6.0 Hz, 3H), 3.56 (dd, J=15, 9.9 Hz, 1H), 3.82–3.96 (m, 2H), 4.58–4.74 (complex m, 2H), 7.72 (dd, J=8.2 Hz, J=15.6 Hz, 1H), 7.87 (t, J=6.7 Hz, 1H), 8.00 (t, 6.7 Hz, 1H), 8.13 (d, J=7.5 Hz, 1H), 8.20 (s, 1H), 8.37 (d, J=15.4 Hz, 1H), 8.52 (d, J=8.0 Hz, 1H), 8.58 (s, 1H), 10.1 (d, J=8.4 Hz, 1H).

IR (KBr): 3400, 1755, 1670, 1620 cm$^{-1}$.

UV (H$_2$O): λ=288 nm, ε=23,000.

EXAMPLE 316

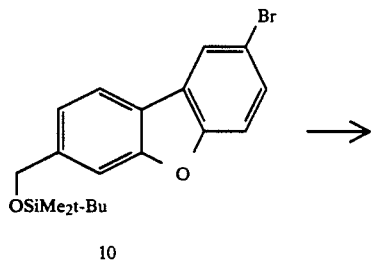

3-(Trimethylstannyl)-7-(t-butyldimethylsilyloxymethyl)dibenzofuran (316)

To a solution of the dibenzofuran 10 (995 mg, 2.5 mmol) in anhydrous THF (25 mL) at −78° C. under a nitrogen atmosphere was added a 1.7M t-butyllithium in pentane solution (3.0 mL, 5.1 mmol). The resulting yellow solution was stirred for 100 min., then trimethyltin chloride (548 mg, 2.75 mmol) was added as a solid. The mixture was allowed to warm to ambient temperature and then stirred for 3 hours. The reaction mixture was then poured into ether and the organic solution was washed with water (3 times) and then with brine. The organic solution was then dried with magnesium sulfate, filtered and concentrated under vacuum. Flash chromatography of the residue (silica gel, 10% methylene chloride in hexanes) provided 815 mg of the stannane 316 (68% yield) as a crystalline solid.

$^1$H-NMR (300 MHz, CDCl$_3$): δ0.22 (s, 6H), 0.35 (s, 9H), 0.95 (s, 9H), 4.88 (s, 2H), 7.24–7.28 (m, 1H), 7.52–7.59 (m, 3H), 7.89 (d, J=7.2 Hz, 1H), 8.02 ppm (s, 1H).

EXAMPLE 317

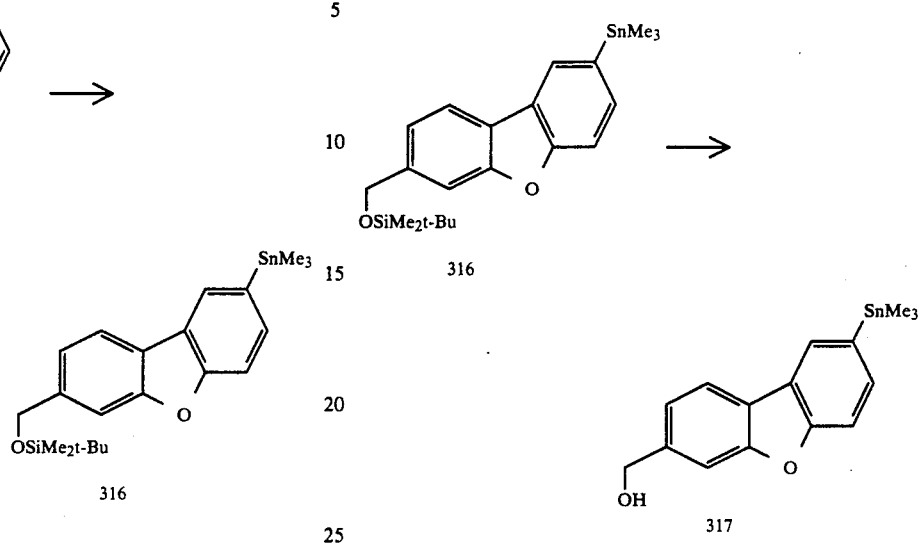

3-(Trimethylstannyl)-7-(hydroxymethyl)dibenzofuran (317)

To a solution of the dibenzofuran 316 (339 mg, 0.71 mmol) in anhydrous THF (7 mL) at 0° C. under a nitrogen atmosphere was added dropwise a 1M solution of tetrabutylammonium fluoride in THF (0.92 mL, 0.92 mmol). The reaction solution was stirred for 30 min., then saturated ammonium chloride was added. The mixture was then extracted with EtOAc and the organic solution was washed with brine. The organic solution was then dried with magnesium sulfate and then filtered and concentrated under vacuum. Flash chromatography of the residue (silica gel, 25% EtOAc in hexanes) provided 182 mg of 317 (70% yield) as a white solid.

$^1$H-NMR (300 MHz, CDCl$_3$): δ0.35 (s, 9H), 1.75 (apparent t, J=5.0 Hz, 1H), 4.85 (d, J=9 Hz, 2H), 7.34 (d, J=7.8 Hz, 1H), 7.52–7.60 (m, 3H), 7.84 (d, J=7.8 Hz, 1H), 8.05 ppm (s, 1H).

EXAMPLE 318

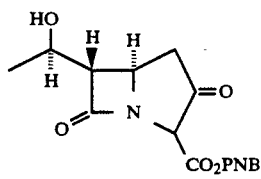

A i) Tf$_2$O/DIPA
ii) TMSOTf/TEA iii) Pd$_2$(DBA)$_3$·CHCl$_3$/ZnCl$_2$
1-methyl-2-pyrrolidinone

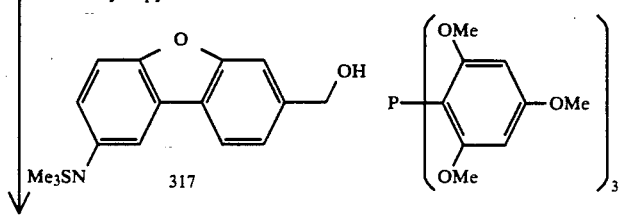

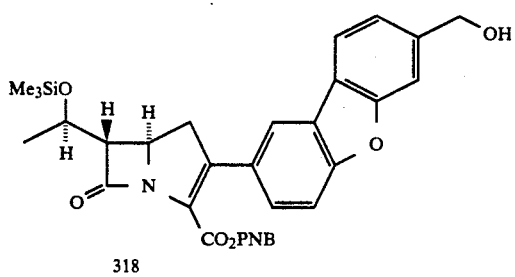

318 p-Nitrobenzyl-(5R,6S)-2-(7-hydroxymethyl)-3-dibenzofuranyl)-6-[1R-(trimethylsilyloxy)ethyl]carbapen-2-em-3-carboxylate (318)

Using the procedure described in Example 308, but substituting the stannane 317 for the stannane 307 provided the title compound in 70% yield.

$^1$H-NMR (300 MHz, CDCl$_3$): δ0.15 (s, 9H), 1.30 (d, J=6.3 Hz, 3H), 1.97 (dd, J$_1$=J$_2$=3.0 Hz, 1H), 3.27 (dd, J=6.4, 2.9 Hz, 1H), 3.31 (complex m, 2H), 4.26 (complex m, 2H), 4.83 (d, J=5.6 Hz, 2H), 5.21 (AB$_q$, J$_{AB}$=13.6 Hz, Δν$_{AB}$=54.3 Hz, 2H), 7.28 (d, J=8.5 Hz, 3H), 7.40 (dd, J=8.6, 1.8 Hz, 1H), 7.49 (d, J=8.4 Hz, 1H), 7.56 (s, 1H), 7.69 (d, J=8.0 Hz, 1H), 7.82 (d, J=1.6 Hz, 1H), 7.91 ppm (d, J=8.7 Hz, 2H);

IR (CHCl$_3$): 3600, 1770, 1720, 1600, 1520 cm$^{-1}$;

UV (CH$_3$CN): λ$_{max}$ 290 nm (ε 10,500), λ$_{max}$ 253 nm (ε 11,300).

EXAMPLE 319

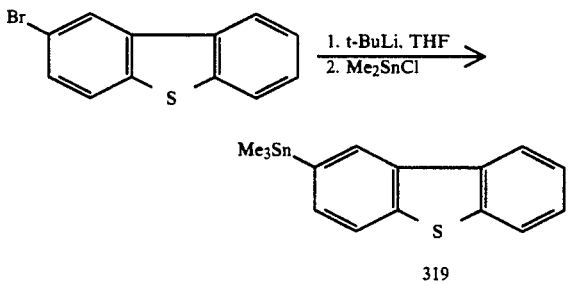

319

3-(Trimethylstannyl)-dibenzothiophene (319)

Using the procedure described in Example 316, but substituting 3-bromodibenzothiophene for the bromodibenzofuran 10 of Example 316, provided the title compound in 82% yield.

$^1$H-NMR (300 MHz, CDCl$_3$): δ0.37 (s, 9H), 7.41–7.48 (complex m, 2H), 7.54 (d, J=8.6 Hz, 1H), 7.82–7.86 (complex m, 2H), 8.18–8.22 (m, 1H), 8.27 ppm (s, 1H).

EXAMPLE 320

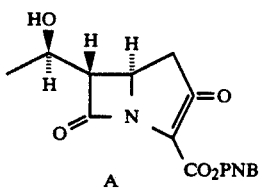

A i) Tf$_2$O/DIPA
ii) TMSOTf/TEA
iii) Pd$_2$(DBA)$_3$CHCl$_3$/ZnCl$_2$
1-methyl-2-pyrrolidinone

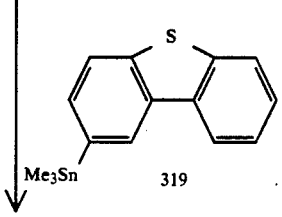

319

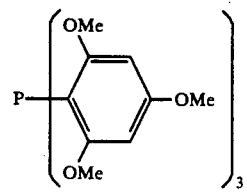

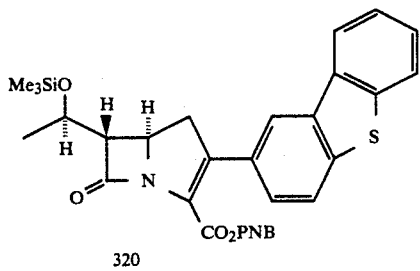

320 p-Nitrobenzyl-(5R,6S)-2-(3-dibenzothienyl)-6-[1R-(trimethylsilyloxy)ethyl]carbapen-2-em-3-carboxylate (320)

Using the procedure described in Example 308 but substituting the dibenzothienylstannane 319 for the stannane 307 in Example 308 provided the title compound in 70% yield.

$^1$H-NMR (300 MHz, CDCl$_3$): δ0.15 (s, 9H), 1.31 (d, J=6.2 Hz, 3H), 3.26–3.45 (complex m, 3H), 4.22–4.35 (complex m, 2H), 5.22 (AB$_q$, J$_{AB}$=13.3 Hz, Δν$_{AB}$=51.6 Hz, 2H), 7.28 (d, J=8.7 Hz, 2H), 7.37–7.47 (complex m, 3H), 7.58–7.80 (m, 2H), 7.83–7.97 (complex m, 3H), 8.06 pm (d, J=1.6 Hz, 1H);

IR (CHCl$_3$): 1770, 1720, 1600, 1520 cm$^{-1}$;

UV (CH$_3$CN): λ$_{max}$ 240 nm (ε 14,800).

EXAMPLE 321

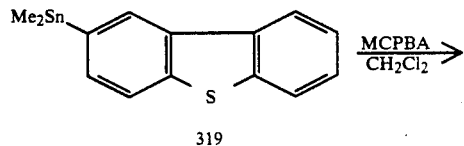

319

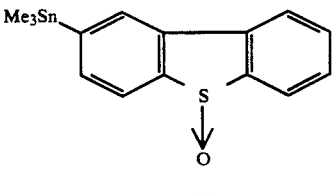

321

3-(Trimethylstannyl)-9-oxodibenzothiophene (321)

To a stirred solution of the dibenzothienylstannane 314 (255 mg, 0.73 mmol) in methyl chloride (7.3 mL) at −78° C. under a nitrogen atmosphere was added m-chloroperbenzoic acid (151 mg, 0.88 mmol). The reaction mixture was allowed to warm to 0° C. and was stirred at that temperature for 3 hours. The reaction was then quenched with 5% aqueous sodium sulfite. The mixture was then extracted with ether and the organic solution was washed with water and then with saturated aqueous sodium bicarbonate. The organic solution was dried with magnesium sulfate, filtered and concentrated under vacuum. Flash chromatography of the residue (silica gel, 30% EtOAc in hexanes) provided 186 mg of the 9-oxodibenzothienylstannane 321 (70% yield).

$^1$H-NMR (300 MHz, CDCl$_3$): δ0.36 (s, 9H), 7.44–7.48 (m, 1H), 7.54–7.61 (complex m, 2H), 7.83 (d, J=7.7 Hz, 1H), 7.88–7.97 ppm (complex m, 3H).

EXAMPLE 322

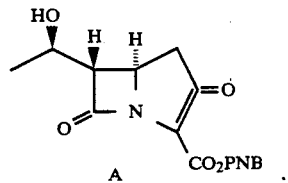

A i) Tf$_2$O/DIPA
ii) TMSOTf/TEA iii) Pd$_2$(DBA)$_3$·CHCl$_3$/ZnCl$_2$
1-methyl-2-pyrrolidinone

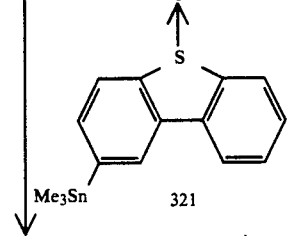

321

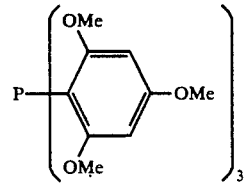

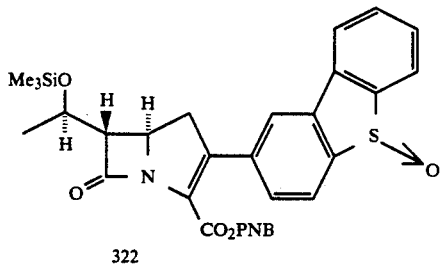

p-Nitrobenzyl-(5R,6S)-2-(9-oxo-3-dibenzothienyl)-6-[1R-(trimethylsilyloxy)ethyl]-carbapen-2-em-3-carboxylate (322)

Using the procedure described in Example 308 but substituting the 9-oxodibenzothienylstannane 321 for the stannane 307 in Example 308 provided the title compound in 75% yield.

$^1$H-NMR (300 MHz, CDCl$_3$): δ (diastereomers) 0.14 (s, 9H), 1.28 (d, J=6.2 Hz, 3H), 3.18-3.41 (complex m, 3H), 4.23-4.36 (complex m, 2H), 5.23-5.38 (m, 2H), 7.38-7.65 (complex m, 5H), 7.72 (s, 1H), 7.92-7.98 (m, 3H), 8.06 ppm (dd, J=8.8, 2.2 Hz, 2H);

IR (CHCl$_3$): 1778, 1720, 1600, 1520 cm$^{-1}$;

UV (CH$_3$CN): λ$_{max}$ 250 nm (290+325 shoulder), (ε27,400).

EXAMPLE 323

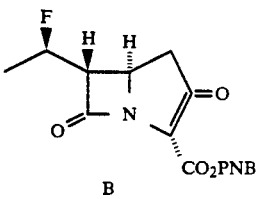
B i) Tf$_2$O/DIPA/ THF/−78° C.   ii) Pd$_2$(DBA)$_3$.CHCl$_3$/ZnCl$_2$

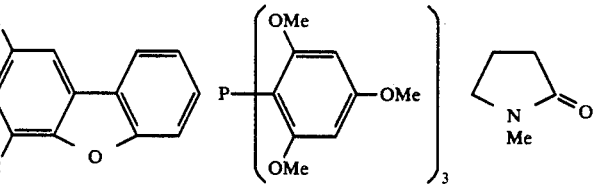
307

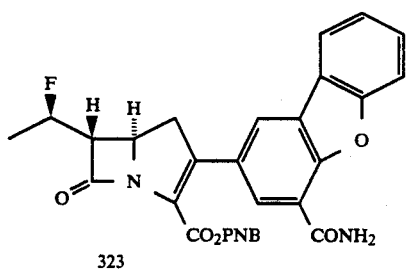
323 p-Nitrobenzyl-(5R,6R)-2-(1-carbamoyl-3-dibenzofuranyl)-6-[1R-fluoroethyl]-carbapen-2-em-3-carboxylate (323)

To a stirred solution of B (71 mg; 0.203 mmol) in anhydrous THF (1 mL) cooled to −78° C. under nitrogen was added diisopropylamine (31 μL; 0.233 mmol; 1.1 equiv.). After 10 minutes trifluoromethanesulfonic anydride (38 μL; 0.233 mmol; 1.1 equiv.) was added to the yellow solution. Twenty-five minutes had elapsed before anhydrous 1-methyl-2-pyrrolidinone (1 mL) was added, followed immediately by Pd$_2$(DBA)$_3$.CHCl$_3$ (4.2 mg; 2 mol %), tris(2,4,6-trimethoxyphenyl)phosphine (8.6 mg, 8 mol %) and stannane 307 (76 mg; 0.233 mmol; 1.1 equiv.) in one portion all as solids. Zinc chloride in diethyl ether (135 μL; 0.233 mmol; 1.1 equiv.) was added last. The −78° C. bath was removed and the reaction mixture quickly raised to ambient temperature using a lukewarm water bath during which time an intense wine-red color developed. The reaction was then stirred for 11 minutes after which time the contents of the flask were poured into Et$_2$O and washed with water and brine, dried over MgSO$_4$, filtered and the solvent removed in vacuo. Purification by flash chromatography (50-70% EtOAc/hexanes) provided 89 mg (80%) of compound 323.

$^1$H-NMR (300 MHz, CDCl$_3$): δ1.53 (dd, J=24.0, 6.2 Hz, 3H), 3.32-3.52 (complex m, 3H), 4.39 (dt, J=9.5, 2.6 Hz, 1H), 4.92-5.17 (complex m, 2H), 5.29 (d, J=13.3 Hz, 1H), 6.15-6.25 (broad s, 1H), 7.28-7.42 (complex m, 3H), 7.47-7.64 (complex m, 3H), 7.82 (d, J=7.1 Hz, 1H), 7.95 (d, J=8.7 Hz, 2H), 8.06 (d, J=1.7 Hz, 1H), 8.18 (d, J=1.8 Hz, 1H).

IR (CHCl$_3$): 3500, 3400, 3000, 1780, 1675, 1590, 1520 cm$^{-1}$.

UV (CH$_3$CN): λ=250 (ε=2000), λ=290 (ε=1700).

EXAMPLE 324

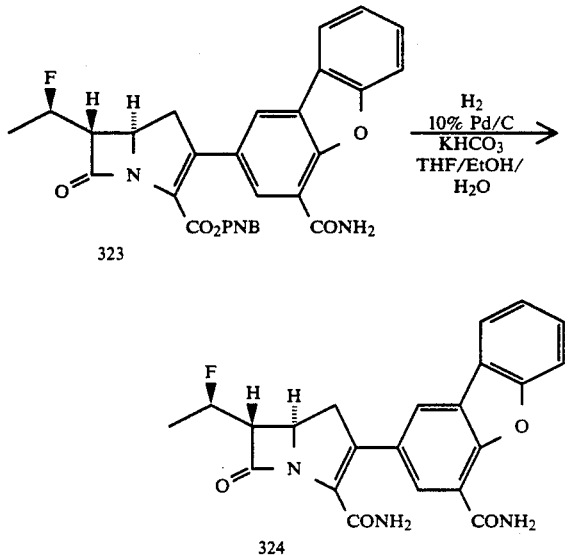

Potassium (5R,6R)-2-(1-carbamoyl-3-dibenzofuranyl)-6-(1R-fluoroethyl)-carbapen-2-em-3-carboxylate (324)

To a solution of 323 (88 mg; 0.162 mmol) in THF/EtOH/H$_2$O (1.3:1.3:1.0) was added potassium bicarbonate (18 mg; 0.178 mmol; 1.1 equiv.). The mixture was placed in a sonicator for several minutes to dissolve the salt. To this stirred solution was then added 10% Pd/C (10 weight %; 8.8 mg). A balloon filled with H$_2$ was attached to the reaction vessel and the vessel was evacuated and purged with H$_2$ ten times before being allowed to stir under a H$_2$ atmosphere at ambient temperature for one hour. The reaction solution was then filtered through a pad of celite to remove the catalyst, taking care to wash the pad well with HPLC grade water. The THF and EtOH were then removed in vacuo and the remaining water frozen to −78° C. and lyophilized at 0° C. Purification of the crude solid via reverse phase prep-plate chromatography using 4:1 H$_2$O/CH$_3$CN as an eluent provided 46 mg (64%) of 324 as a white solid. Compound 324 is also listed in Table III, where it is designated Example 124.

$^1$H-NMR (300 MHz, D$_2$O/CD$_3$CN, 2:1): δ1.85 (dd, J=24.9, 6.3 Hz, 3H), 3.56 (dd, J=16.8, 9.7 Hz, 1H), 3.93 (dd, J=16.7, 8.7 Hz, 1H), 4.04–4.07 (m, ½H), 4.13–4.18 (m, ½H), 4.71–4.83 (m, 1H), 5.40–5.48 (m, ½H), 5.58–5.65 (m, ½H), 7.86 (t, J=7.7 Hz, 1H), 7.99 (t, J=7.2 Hz, 1H), 8.10 (d, J=8.3 Hz, 1H), 8.38 (d, J=1.7 Hz, 1H), 8.50 (d, J=7.7 Hz, 1H), 8.65 (d, J=1.7 Hz, 1H).

IR (KBr): 1760, 1670, 1600 cm$^{-1}$.

UV (H$_2$O): λ$_{max}$ 245 (ε=17,000), λ$_{max}$ 295 (ε=14,000).

TABLE IV

Employing the procedures described herein, additional compounds of the present invention were prepared. These are described in Table IV which additionally includes characterizing data.

TABLE IV

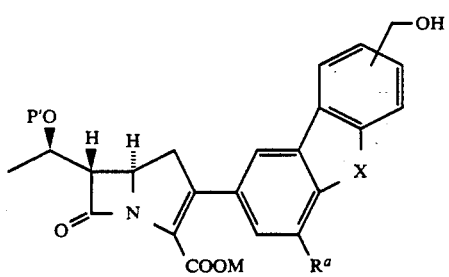

| Exp. No. | M | R' | R | X | R$^a$ | R$^b$ | λ$_{max}^{H_2O}$ (nm) |
|---|---|---|---|---|---|---|---|
| 325 | K | OH | H | O | CONHCH$_2$CH$_2$OH | H | 295, 247 |
| 326 | K | OH | H | O | CONHOCH$_3$ | H | 294 |
| 327 | K | OH | H | O | H | 7-CON(CH$_3$)$_2$ | 296 |
| 328 | K | OH | H | O | H | 7-COCH$_3$ | 310 |
| 329 | K | OH | H | S | H | 7-CO$_2$CH$_3$ | 301, 282, 246 |
| 330 | K | OH | H | SO | H | 7-CO$_2$CH$_3$ | 304, 256 |
| 331 | K | OH | H | SO | H | 7-COCH$_3$ | 309, 260 |
| 332 | K | F | H | O | H | 7-CH$_2$OH | 289 |

What is claimed is:

1. A compound of the formula:

wherein:

R$^a$ is selected from the group consisting of H, Cl, Br, I, SCH$_3$, CN, CONH$_2$, CHO, SOCH$_3$, SO$_2$CH$_3$, CO$_2$M, CH$_2$OP', and OP';

P' is a removable protecting group for hydroxy; and

M is a removable carboxy protecting group; and

X is O or S(O)$_{0-2}$.

2. A compound of claim 1 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

3. A compound of claim 1 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl, and allyloxycarbonyl.

* * * * *